US007303873B2

(12) United States Patent
Miki et al.

(10) Patent No.: US 7,303,873 B2
(45) Date of Patent: *Dec. 4, 2007

(54) CRYPTIC REGULATORY ELEMENTS OBTAINED FROM PLANTS

(75) Inventors: Brian Miki, Ottawa (CA); Thérèse Ouellet, Nepean (CA); Jiro Hattori, Ottawa (CA); Elizabeth Foster, Nepean (CA); Hélène Labbé, Ottawa (CA); Teresa Martin-Heller, Gloucester (CA); Lining Tian, London (CA); Daniel Charles William Brown, Ilderton (CA); Peijun Zhang, Ottawa (CA); Keqiang Wu, Nepean (CA)

(73) Assignee: Her Majesty the Queen in Right of Canada as Represented by the Minister of Agriculture and Agri-Food, Ottawa, Ontario (CA)

( * ) Notice: Subject to any disclaimer, the term of this patent is extended or adjusted under 35 U.S.C. 154(b) by 127 days.

This patent is subject to a terminal disclaimer.

(21) Appl. No.: 10/437,261

(22) Filed: May 13, 2003

(65) Prior Publication Data

US 2004/0073022 A1 Apr. 15, 2004

Related U.S. Application Data

(63) Continuation of application No. 09/747,368, filed on Dec. 22, 2000, now abandoned, which is a continuation of application No. PCT/CA99/00578, filed on Jun. 22, 1999, which is a continuation of application No. 09/457,123, filed on Dec. 7, 1999, now abandoned, which is a continuation-in-part of application No. 09/174,999, filed on Oct. 19, 1998, now abandoned, which is a continuation of application No. 08/593,121, filed on Feb. 1, 1996, now Pat. No. 5,824,872.

(30) Foreign Application Priority Data

| May 9, 1995 | (CA) | ................................. 2149000 |
| Sep. 9, 1998 | (CA) | ................................. 2246892 |

(51) Int. Cl.
| C12Q 1/68 | (2006.01) |
| C12N 15/63 | (2006.01) |
| C12N 15/82 | (2006.01) |
| C07H 21/02 | (2006.01) |
| C12N 5/04 | (2006.01) |

(52) U.S. Cl. .................... 435/6; 435/320.1; 435/468; 536/23.1

(58) Field of Classification Search ..................... None
See application file for complete search history.

(56) References Cited

U.S. PATENT DOCUMENTS 5,164,316 A 11/1992 McPherson et al. ......... 435/419
5,196,525 A 3/1993 McPherson et al. ......... 536/24.1
5,322,938 A 6/1994 McPherson et al. ......... 536/24.1
5,424,200 A 6/1995 McPherson et al. ......... 435/70.1
5,491,288 A 2/1996 Chaubet et al. ............. 800/300
5,824,872 A 10/1998 Miki et al. .................. 800/278

FOREIGN PATENT DOCUMENTS

| CA | 028268WO A1 | 8/1997 |
| WO | WO 97/28268 | * 8/1997 |

OTHER PUBLICATIONS

Tuominen et al, Altered Growth and Wood Charateristics in Transgenic Hybrid Aspen Expressing Agrobacterium tumefaciens T-DNA Indoleacetic Acid-Biosynthetic Genes, Plant Physiol. 109:1179-1189, 1995.*
Ebinuma et al. Selection of marker-free transgenic plants using the isopentenyl transferase gene. PNAS 94:2117-2121. 1997.*
Cornejo et al., "Activity of a maize ubiquitin promoter in transgenic rice," Plant Molecular Biology 23: 567-581, (1993).
Odell et al., "Identification of DNA sequences required for activity of the cauliflower mosaic virus 35S promoter," Nature 313: 810-812, (1985).
Zhang et al., "Analysis of Rice Act1 5' Region Activity in Transgenic Rice Plants," The Plant Cell, 3: 1155-1165 (1991).
Xu et al., "Rice Triosephosphate Isomerase Gene 5' Sequence Directs β-Glucuronidase Activity in Transgenic Tobacco but Requires an Intron for Expression in Rice," Plant Physiol. 106: 459-467, (1994).
Mandel et al., "Definition of constitutive gene expression in plants: the translation initiation factor 4A gene as a model," Plant Molecular Biology 29: 995-1004 (1995).

(Continued)

Primary Examiner—Nancy Vogel
Assistant Examiner—Michele K. Joike
(74) Attorney, Agent, or Firm—Heslin Rothenberg Farley & Mesiti P.C.

(57) ABSTRACT

T-DNA tagging with a promoterless β-glucuronidase (GUS) gene generated transgenic *Nicotiana tabacum* plants that expressed GUS activity either only in developing seed coats, or constitutively. Cloning and deletion analysis of the GUS fusion revealed that the promoter responsible for seed coat specificity was located in the plant DNA proximal to the GUS gene. Analysis of the region demonstrated that the seed coat-specificity of GUS expression in this transgenic plant resulted from T-DNA insertion next to a cryptic promoter. This promoter is useful in controlling the expression of genes to the developing seed coat in plant seeds. Similarly, cloning and characterization of the cryptic constitutive promoter revealed the occurrence of several cryptic regulatory regions. These regions include promoter, negative regulatory elements, transcriptional enhancers, core promoter regions, and translational enhancers and other regulatory elements.

20 Claims, 32 Drawing Sheets

OTHER PUBLICATIONS

Duncker et al., "Introns boost transgene expression in Drosophila melanogaster," Mol Gen Genet 254: 291-296 (1997).

Forsythe et al., "Characterization of the Acidic Domain of the IE1 Regulatory Protein from Orgyia pseudotsugata Multicapsid Nucleopolyhedrovirus," Virology 252: 65-81 (1998).

Helliwell et al., "The sequence surrounding the translation initiation codon of the pea plastocyanin gene increases translational efficiency of a reporter gene," Plant Molecular Biology 29: 621-626, (1995).

Hattori et al., "The Isolation of High-Molecular-Weight DNA from Plants," Analytical Biochemistry 165: 70-74, (1987).

Melton et al., "Efficient in vitro synthesis of biologically active RNA and RNA hybridization probes from plasmids containing a bacteriophage SP6 promoter," Nucleic Acids Research 12(18): 7035-7056 (1984).

Walden et al., "T-DNA as a gene tag," The Plant Journal 1(3): 281-288 (1991).

Tomashevskaya et al., "Effects of sequence elements in the potato virus X RNA 5' non-translated αβ-leader on its translation enhancing activity," Journal of General Virology 74: 2717-2724 (1993).

Theilmann et al., "Molecular Analysis of the trans-Activating IE-2 Gene of Orgyia pseudotsugata Multicapsid Nuclear Polyhedrosis Virus," Virology 187: 84-96 (1992).

Gheysen et al., "Cloning and sequence analysis of truncated T-DNA inserts from Nicotiana tabacum," Gene 94: 155-163 (1990).

Campbell, "Lipofection Reagents Prepared by a Simple Ethanol Injection Technique," BioTechniques 18(6): 1027-1032.

Holtorf et al., "Comparison of different constitutive and inducible promoters for the overexpression of transgenes in *Arabidopsis thaliana*," Plant Molecular Biology 29:637-646 (1995).

Sanford et al., "Optimizing the Biolistic Process for Different Biological Applications," Methods in Enzymology 217:483-509, (1993).

Gallie et al., "Identification of the motifs within the tobacco mosaic virus 5'-leader responsible for enhancing translation," Nucleic Acids Research 20(17): 4631-4638. (1992).

Datla et al., "Improved high-level constitutive foreign gene expression in plants using an AMV RNA4 untranslated leader sequence," Plant Science 94: 139-149 (1993).

Datla et al., "Modified binary plant transformation vectors with the wild-type gene encoding NPTII," Gene 211: 383-384 (1992).

Jefferson, "Assaying Chimeric Genes in Plants: The GUS Gene Fusion System," Plant Molecular Biology Reporter 5(4): 387-405 (1987).

Irniger et al., "The yeast actin intron contains a cryptic promoter that can be switched on by preventing transcriptional interference," Nucleic Acids Research 20(18): 4733-4739 (1992).

Gottlob-McHugh et al., "Normal Growth of Transgenic Tobacco Plants in the Absence of Cytosolic Pyruvate Kinase," Plant Physiol 100: 820-825 (1992).

Gasser et al., "Cohabitation of Scaffold Binding Regions with Upstream/Enhancer Elements of Three Developmentally Regulated Genes of D. melanogaster," Cell. vol. 46: 521-530 (1986).

Fourel et al., "Expression of the Woodchuck N-*myc2* Retroposon in Brain and in Liver Tumors Is Driven by a Cryptic N-*myc* Promoter," Molecular and Cellular Biology 12(12): 5336-5344 (1992).

Fobert et al., "Detection of gene regulatory signals in plants revealed by T-DNA mediated fusions," Plant Molecular Biology 17: 837-851 (1991).

Fickett, "Recognition of protein coding regions in DNA sequences," Nucleic Acids Research 10(17): 5303-5318 (1982).

Chen et al., "A DNA sequence element that confers seed-specific enhancement to a constitutive promoter," The EMBO Journal 7(2): 297-302 (1988).

Bevan, "Binary *Agrobacterium* vectors for plant transformation," Nucleic Acids Research 12(22): 8711-8721 (1984).

Baszczynski et al., "Isolation and nucleotide sequence of a genomic clone encoding a new *Brassica napus* napin gene," Plant Molecular Biology 14: 633-635 (1990).

Al-Shawi et al., "The Herpes Simplex Virus Type 1 Thymidine Kinase Is Expressed in the Testes of Transgenic Mice under the Control of a Cryptic Promoter," Molecular and Cellular Biology 11(8): 4207-4216 (1991).

Breyne et al., "Characterization of a Plant Scaffold Attchment Region in a DNA Fragment That Normalizes Transgene Expression in Tobacco," The Plant Cell 4: 463-471 (1992).

Yamamoto et al., "5'-Leader of a Photosystem I Gene in *Nicotiana sylvestris*, psaDb, Contains a Translational Enhancer," The Journal of Biological Chemistry 270(21): 12466-12470 (1995).

Newman, "DST Sequences, Highly Conserved among Plant SAUR Genes, Target Reporter Transcripts for Rapid Decay in Tobacco," The Plant Cell 5: 701-714 (1993).

Dickey et al., "Light Regulation of Fed-1 mRNA Requires an Element in the 5' Untranslated Region and Correlates with Differential Polyribosome Association," The Plant Cell 10: 475-484 (1998).

Curie et al., "A Strong Inhibitor of Gene Expression in the 5' Untranslated Region of the Pollen-Specific LAT59 Gene of Tomato," The Plant Cell 9: 2025-2036 (1997).

Bolle et al., "Segments encoding 5'-untranslated leaders of genes for thylakoid proteins contain cis-elements essential for transcription," The Plant Journal 6(4) 513-523 (1994).

Jobling et al., "Enhanced translation of chimaeric messenger RNAs containing a plant viral untranslated leader sequence," Nature 325: 622-625 (1987).

Mandel et al.,. "Definition of constitutive gene expression in plants: the translation initiation factor 4A gene as a model," Plant Molecular Biology 29: 995-1004 (1995).

Yanofsky et al., "The protein encoded by the Arabidopsis homeotic gene agamous resembles transcription factors," Nature 346: 35-39 (1990).

Lijsebettens et al., "Insertional mutagenesis in Arabidopsis thaliana," Plant Science 80: 27-37 (1991).

Takahashi et al., "Activation and Suppression of a Cryptic Promoter in the Intron of the Human Melanoma-associated ME491 Antigen Gene," Jpn. J. Cancer Res. 82: 1239-1244 (1991).

Sanders et al., "Comparison of cauliflower mosaic virus 35S and nopaline synthase promoters in transgenic plants," Nucleic Acids Research 15(4): 1543-1558 (1987).

Feldmann, "T-DNA insertion mutagenesis in Arabidopsis: mutational spectrum," The Plant Journal 1(1): 71-82 (1991).

Rutledge et al., "Molecular characterization and genetic origin of the *Brassica napus* acetohydroxyacid synthase multigene family," Mol Gen Genet 229: 31-40 (1991).

Okamuro et al., "Tobacco single-copy DNA is highly homologous to sequences present in the genomes of its diploid progenitors," Mol Gen Genet 198: 290-298 (1985).

Lindsey et al., "Tagging genomic sequences that direct transgene expression by activation of a promoter trap in plants," Transgenic Research 2: 33-47 (1993).

Kosugi et al., "An Improved Assay For β-Glucuronidase In Transformed Cells: Methanol Almost Completely Suppresses A Putative Endogenous β-Glucuronidase Activity," Plant Sciences 70: 133-140 (1990).

Koncz et al., "T-DNA insertional mutagenesis in *Arabidopsis*," Plant Molecular Biology 20: 963-976 (1992).

Koltunow et al., "Different Termporal and Spatial Gene Expression Patterns Occur during Another Development," The Plant Cell 2: 1201-1224 (1990).

Kertbundit et al., "In vivo random β-glucuronidase gene fusions in *Arabidopsis thaliana*," Proc. Natl. Acad. Sci USA 88: 5212-5216 (1991).

Joshi, "An inspection of the domain between putative TATA box and translation start site in 79 plant genes," Nucleic Acids Research 15(16): 6643-6653 (1987).

Agatep et al., "2 Hybrid System TRAFO Protocol," http://www.umanitoba.ca/faculties/medicine/biochem/gietz/2HS.html, pp. 1-6 (1998).

Ouellet et al., "Members of the acetohydroxyacid synthase multigene family of *Brassica napus* have divergent patterns expression," The Plant Journal 2(3): 321-330 (1992).

Leahy et al., "Effects of Ethanol Concentration and Incubation Period at 65 C on CAT Activity in Mammalian Cell Extracts," BioTechniques 19: 894-898 (1995).

* cited by examiner

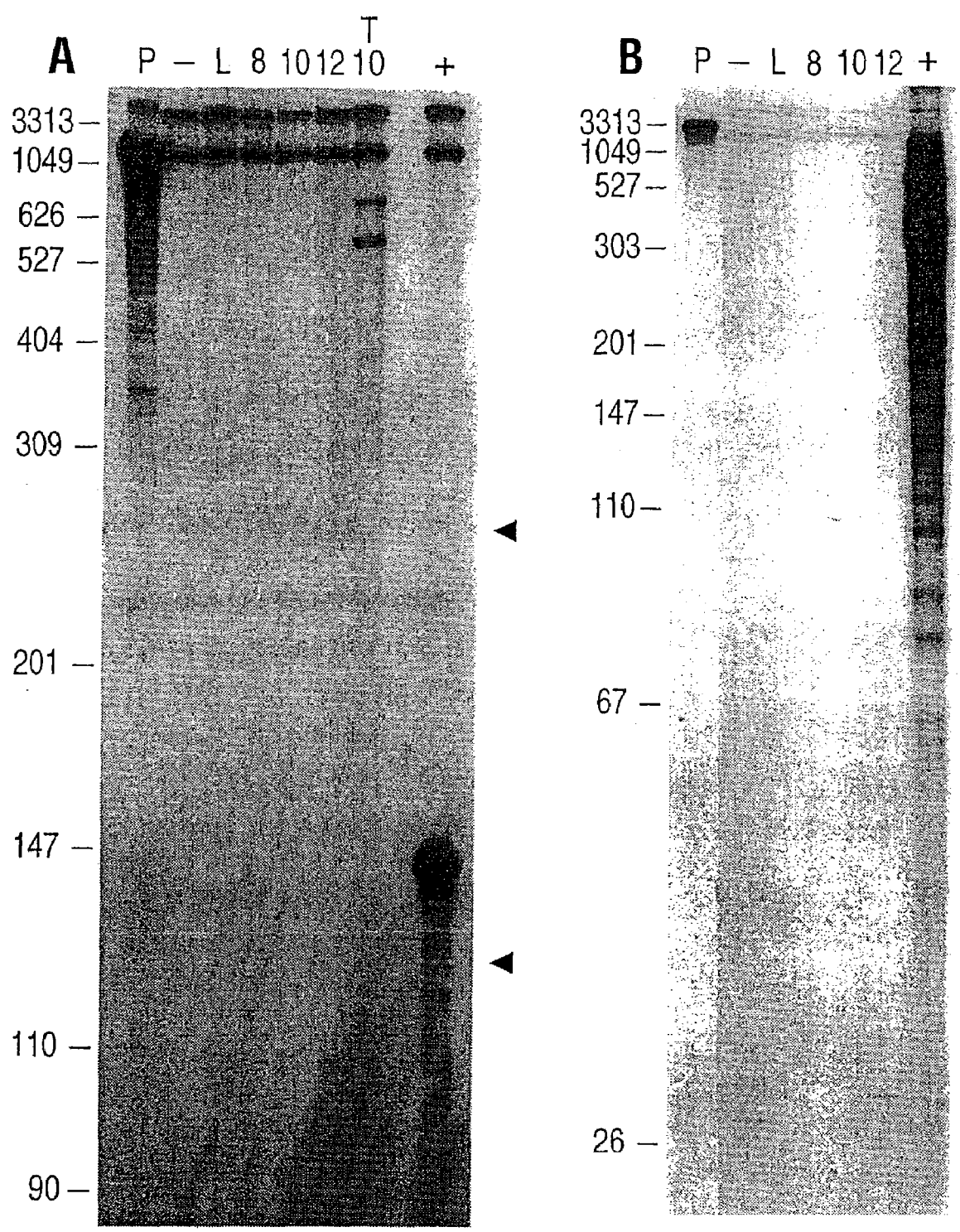
FIGURE 5A  FIGURE 5B

```
                                          1   2
      Xbal                                ┌──┌────────────→
  1   TCTAGACTTGTCTTTTCTTTACATAATCCTCTTCTTCTTTTTTTTGTTAGTTTCTTCTGT 61   TTTATCCAAAAAACGAATTATTGATTAAGAAATACACCAGACAAGTTTTTTACTTCTTTT
      1   2
      ┌──┌───────→
121   TCTTTTTTTTTTGTGGTAAAAAATTACACCTGGACAAGTTTATCACGAAAATGAAAATT
                                                       8
                                                       ┌────────→
181   GCTATTTAAGGGATGTAGTTCCGGACTATTTGGAAGATAAGTGTTAACAAAATAAATAAA
                            6
                          ┌─3─────→                    7
                                                       ┌──4
241   TAAAAAGTTTATACAGTTAGATCTCTCTATAACAGTCATCCTTATTTATAACAATACTTT
      7
      ┌────→                                4
      4                                     ┌─3───────────→
301   ACTATAACCGTCAAATTTATTTTGAAACAAAATTTTCATGTTATGTTACTATAACAGTAT
                                                   6
                                          ←────────┐
361   TTTATTATAGCAACCAAAAAATATCGAAACAGATACGATTGTTATAGAGCGATTTGATTG
                                          SnaB1
421   TATCATTATCCACATATTTTCGTAAGCCCAATTACTCCTCCTACGTACGATGAAAGTAAA

481   CCAATTTAAAGTTGCAAAAATCCAATAGATTTCAATACTTCTTCAACTGGCGTTATGTTA

541   GGTAATGACTCCTTTTTAACTTTTCATCTTTAATTTGAAGTTTCTTTCATTAAAAGAAAG
      5—Xbal—→                                   5—Xbal—→
601   TTTCTAGAAGAGAAGTGTTTTAACACTTCTAGCTCTACTATTATCTGTGTTTCTAGAAGA
                                                              8
                                                          ←────┐
661   AAAATAGAAAATGTGTCCACCTCAAAAACAACTAAAGGTGG GCAAATCTC CACCTATTTA
              1              7
          ←───┐  ←───────────┐
721   TTTTATTTTGGATTAATTAAGATATAGTAAAGATCAG TTATAAACG GAGTTTTGAGTTGA 781   TACAG TGAATTTTAAG ATGTGTACCGATTTAACTTTATTTACATTTATGTTTCGCACATA
      TATA                       ↓
841   TAAGAAGTCCGATTTGGAAATACTAGATTTTGTCAATCAGGCAATTCATGTGGTTGAAGA

901   ATTTAAGTTATATACAATGATGATATAAAGAATTTTTATACTATTAGTGCAAATTAATCG

957   ATTACTAAAAATTATTATTCTATTAATTTATGCTATC|GTGCCTCCCCAACCCGTCGACC
                                          |ATATCAAATTTAGTATTCCTTT
                                          *
1005  GCGGTACCCGGTGGTCAGTCCCTT ATG TTA CGT CCT GTA GAA ACC CCA ACC
                                M   L   R   P   V   E   T   P   T
```

FIGURE 6

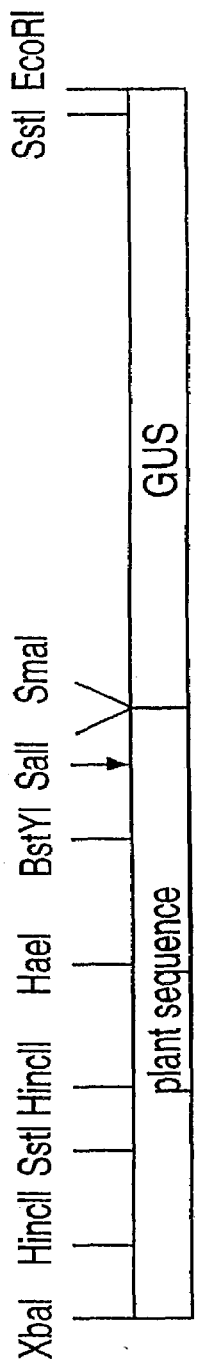
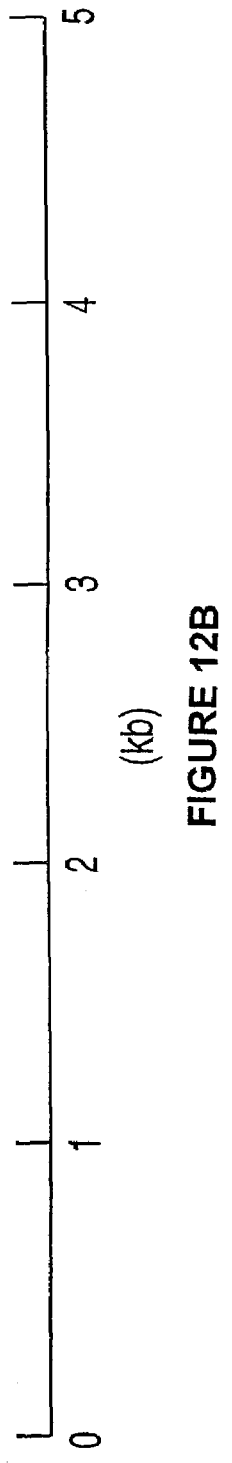
FIGURE 12B
FIGURE 12A

| Constructs | | GUS ACTIVITY* (NO. OF BLUE UNITS/LEAF ±SE) |
|---|---|---|
| -62-[ ]-GUS | -62-GUS | 4.67±0.33 |
| -62-[TATA]-GUS | TA30-GUS | 40.33±5.17 |
| -20-[▨]-GUS | TA35S-GUS | 28.67±2.91 |
| GCC-[-62 ]-GUS | GCC-62-GUS | IN PROGRESS |
| [-197 Dra1][-62 ]-GUS | DRA1-GUS(-197-GUS) | 201.33±41.43 |
| [Dra1][Dra1][ ]-GUS | DRA2-GUS | 259.00±69.94 |
| [-394 Bst1][-197 Dra1][-62 ]-GUS | BST1-GUS(-394-GUS) | 180.33±32.23 |
| [Bst1][Dra1][Bst1][Dra1][ ]-GUS | BST2-GUS | 331.00±47.09 |
| [▨▨▨▨▨▨-46]-GUS | PB1221(35S-GUS) | 269.00±34.36 |
| [-46 ▨]-GUS | -46-35S | 0.33±0.33 |
| [Dra1][▨]-GUS | DRA1-35S | 53.00±20.01 |
| [Bst1][Dra1][▨]-GUS | BST1-35S | 45.67±9.74 |
| [Bst1][Dra1][Bst1][Dra1][▨]-GUS | BST2-35S | 143.33±15.30 | t-CUP [ ]    35S [▨]

FIGURE 13D

FIGURE 13G(i)
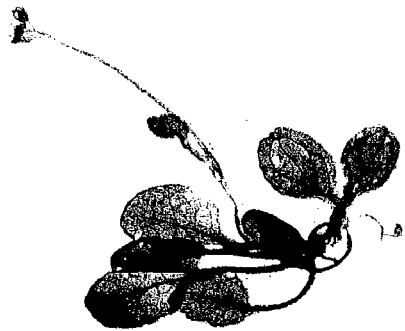
FIGURE 13G(ii)
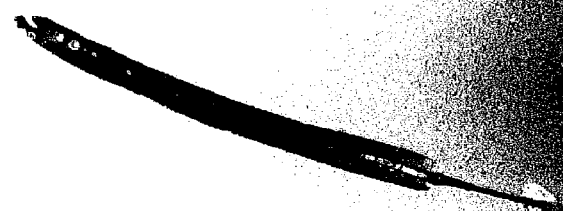
FIGURE 13G(iii)
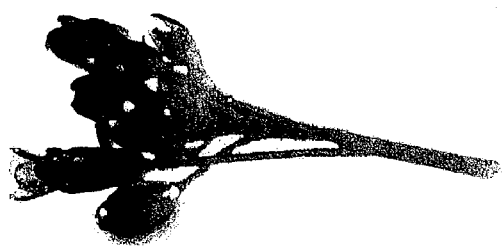

SEQUENCE LISTING

<160> NUMBER OF SEQ ID NOS: 7

<210> SEQ ID NO 1
<211> LENGTH: 1070
<212> TYPE: DNA
<213> ORGANISM: Nicotiana tabacum

<400> SEQUENCE: 1

```
tctagacttg tcttttcttt acataatcct cttcttcttt tttttgttag tttcttctgt      60
tttatccaaa aaacgaatta ttgattaaga aatacaccag acaagttttt tacttctttt     120
tcttttttt tttgtggtaa aaaattacac ctggacaagt ttatcacgaa aatgaaaatt      180
gctatttaag ggatgtagtt ccggactatt tggaagataa gtgttaacaa aataaataaa     240
taaaagttt atacagttag atctctctat aacagtcatc cttatttata acaatacttt      300
actataaccg tcaaatttat tttgaaacaa aattttcatg ttatgttact ataacagtat     360
tttattatag caaccaaaaa atatcgaaac agatacgatt gttatagagc gatttgattg     420
tatcattatc cacatatttt cgtaagccca attactcctc ctacgtacga tgaaagtaaa     480
ccaatttaaa gttgcaaaaa tccaatagat ttcaatactt cttcaactgg cgttatgtta     540
ggtaatgact ccttttaac ttttcatctt taatttgaag tttctttcat taaaagaaag      600
tttctagaag agaagtgttt taacacttct agctctacta ttatctgtgt ttctagaaga     660
aaaatagaaa atgtgtccac ctcaaaaaca actaaaggtg ggcaaatctc cacctattta     720
ttttattttg gattaattaa gatatagtaa agatcagtta taaacggagt tttgagttga     780
```

```
tacagtgaat tttaagatgt gtaccgattt aactttattt acatttatgt ttcgcacata      840
taagaagtcc gatttggaaa tactagattt tgtcaatcag gcaattcatg tggttgaaga      900
atttaagtta tatacaatga tgatataaag aatttttata ctattagtgc aaattaatcg      960
attactaaaa attattattc tattaattta tgctatcgtg cctccccaac ccgtcgaccg     1020
cggtacccgg tggtcagtcc cttatgttac gtcctgtaga aaccccaacc                1070

<210> SEQ ID NO 2
<211> LENGTH: 2224
<212> TYPE: DNA
<213> ORGANISM: Nicotiana tabacum

<400> SEQUENCE: 2
tctagactta cagaaagtct ctaacacgtg agggaatgat ccctttcctt acctccctgt       60
agagatattg gcttttcaac aactagtaca taaatatgcg actttgaccg tgtatcccca      120 gtcaaaggg aacttcaccc tcctagttct ttatttccaa catacatggg gagtaatgct       180
aaatttacat agaagaataa taaaatgaac tgtaactaat gatgtactgt tccaaagaga      240
tgaggacgtc aacatattta ttccttcagc cctttttcaga ataataccat aagtagaaga    300
aatggcacat aaaatgaagt cctcggcaag tcaaatgtaa atctgaaccc acccagctaa     360
cccagtgaac tcaactttcc tggatagatc agcactcctt catgacattg catgccttct     420 cttttaaagag ccgcttgatc tctgaaaacc aaatgaatct ccacagagag atttcgagct    480
ccatgagacg cctttggtt cttgatttac taaacctata aaatgaaag gaagtaggac       540 aactgcattt tgccgcttaa gatgcttcgg cgctttgtga attttaagtc atgagaaagt     600
acaatgttgg aatctcacat tagaacaatg tatttgtaat aacctaggaa agcaaagcta     660
gaagggaggt gcagctaaat cttcttctac cttgttatcc ttgcatttct tgaggaggag    720
gaactgtcct cgcaggtgca aaatctgcag tcgcccaaaa ggatattcag aagtatatta    780
caacatgttt aatggttaac caagtgaaag atcaaaatag tcattagaac aaaatgcgtg    840
ctcagagcgt atctactagt tcatcaaccc agtacacatc tctgaatttc atctcttgcc    900
gttgaactaa gtcaattggt caaagacgca taacatgaga gacactcata aaacggctga    960
ataacatgca gaagacgtca tgcgccttag gtctcattat gcatgagatt attagttata   1020
tgctccttca gtttgactag aaatgaaaaa tcagttaagc ctgtaacgaa atgataacct   1080
gcttcaagaa gattagacta ttttcataa aatatgcagt gccgtgaaat agatacttaa     1140
tcttaggcag gaaaatcttt ctattgggcc ataataagaa ctaccaatta gaaggaggt    1200 agaaagctcc gatactgtta tgaaggccat tctaagtgct gatgtgaatt tcccaataca   1260
aaatgacaac aaaaacaaaa gcctcaatcc taagctagtt ggggtcgcta tataaatcct    1320
cgacatccat ttaactccac ttggactcct ttctttccaa tatttttaata ttgttagatt   1380 aatcatatta ttgcttagct ttctactggc acttaaccta ctgcaaccct cctcttctgg    1440
gattccaaca caaacaacta agaggaattt gaaaaaaga aagcaaatgt gagaagagac     1500
aaaatgtaca atgatacctc ttcttgcagc aaaggaggca ggttctctgc tgagacaagg   1560 ttctctatt cctgcaagac cttcgtatct tttattcgag accatgtatg tggaggtaac    1620
gccagcaata gtgctgtcag cacatcgttg cttgcagggg atcttctgca agcatctcta   1680
tttcctgaag gtctaaccctc gaagatttaa gatttaatta cgtttataat tacaaaattg    1740
attctagtat ctttaattta atgcttatac attattaatt aatttagtac tttcaatttg   1800
ttttcagaaa ttatttttact attttttata aaataaaagg gagaaaatgg ctatttaaat  1860
```

```
actagcctat tttatttcaa ttttagctta aaatcagccc caattagccc caatttcaaa    1920
ttcaaatggt ccagcccaat tcctaaataa cccaccccta acccgcccgg tttccccttt    1980
tgatccaggc cgttgatcat tttgatcaac gcccagaatt tccccttttc cttttttaat    2040
tcccaaacac ccctaactct atcccatttc tcaccaaccg ccacatatga atcctcttat    2100
ctctcaaact ctctcgaacc ttcccctaac cctagcagcc tctcatcatc ctcacctcaa    2160
aacccaccgg aatacatggc ttctcaagcc gtggaaacct tatactcacc tcccttttgct   2220 ctta                                                                  2224
```

```
<210> SEQ ID NO 3
<211> LENGTH: 188
<212> TYPE: DNA
<213> ORGANISM: Artificial Sequence
<220> FEATURE:
<223> OTHER INFORMATION: Description of Artificial Sequence: NdeI-SmaI
      fragment of T1275

<400> SEQUENCE: 3
catatgaatc ctcttatctc tcaaactctc tcgaaccttc ccctaaccct agcagcctct    60
catcatcctc acctcaaaac ccaccggaat acatggcttc tcaagccgtg gaaaccttat   120
actcacctcc ctttgctctt acagtactcg gccgtcgacc gcggtacccg ggtggtcagt   180
cccttatg                                                            188
```

```
<210> SEQ ID NO 4
<211> LENGTH: 129
<212> TYPE: DNA
<213> ORGANISM: Artificial Sequence
<220> FEATURE:
<223> OTHER INFORMATION: Description of Artificial Sequence: delta N,
      with Kozak Sequence

<400> SEQUENCE: 4
agatctatcc tcttatctct caaactctct cgaaccttcc cctaaccctcta gcagcctctc    60 atcatcctca cctcaaaacc caccggccac catggcctct agaggacccc gggtggtcag   120
tcccttatg                                                            129
```

```
<210> SEQ ID NO 5
<211> LENGTH: 119
<212> TYPE: DNA
<213> ORGANISM: Artificial Sequence
<220> FEATURE:
<223> OTHER INFORMATION: Description of Artificial Sequence: delta N,
      without Kozak
      sequence

<400> SEQUENCE: 5
agatctatcc tcttatctct caaactctct cgaaccttcc cctaaccctca gcagcctctc    60 atcatcctca cctcaaaacc caccggtcta gaggatcccc gggtggtcag tcccttatg    119
```

```
<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence:
      transcriptional start site compiled from available dicot plant
      genes

<400> SEQUENCE: 6
```

```
wyaammhaaw                                                                  10

<210> SEQ ID NO 7
<211> LENGTH: 9
<212> TYPE: DNA
<213> ORGANISM: Artificial Sequence
<220> FEATURE:
<223> OTHER INFORMATION: Description of Artificial Sequence: TATA-box
      consensus complied from available dicot plant genes

<400> SEQUENCE: 7 ctatawawa                                                                    9
```

CRYPTIC REGULATORY ELEMENTS OBTAINED FROM PLANTS

This application is a continuation of U.S. Ser. No. 09/747,368 filed on Dec. 22, 2000 now abandoned, which is a continuation of PCT/CA99/00578 filed Jun. 22, 1999, which claims priority of U.S. Ser. No. 09/102,312 filed Jun. 22, 1998 and Canadian Ser. No. 2,246,892 filed Sep. 9, 1998. This application is also a continuation of U.S. Ser. No. 09/457,123 filed Dec. 7, 1999 which is a continuation-in-part of Ser. No. 09/174,999 filed Oct. 19, 1998 now abandoned which is a continuation of Ser. No. 08/593,121 filed Feb. 1, 1996, now issued as U.S. Pat. No. 5,824,872.

FIELD OF INVENTION

This invention relates to cryptic regulatory elements within plants.

BACKGROUND AND PRIOR ART

Bacteria from the genus *Agrobacterium* have the ability to transfer specific segments of DNA (T-DNA) to plant cells, where they stably integrate into the nuclear chromosomes. Analyses of plants harbouring the T-DNA have revealed that this genetic element may be integrated at numerous locations, and can occasionally be found within genes. One strategy which may be exploited to identify integration events within genes is to transform plant cells with specially designed T-DNA vectors which contain a reporter gene, devoid of cis-acting transcriptional and translational expression signals (i.e. promoterless), located at the end of the T-DNA. Upon integration, the initiation codon of the promoterless gene (reporter gene) will be juxtaposed to plant sequences. The consequence of T-DNA insertion adjacent to, and downstream of, gene promoter elements may be the activation of reporter gene expression. The resulting hybrid genes, referred to as T-DNA-mediated gene fusions, consist of unselected plant promoters residing at their natural location within the chromosome, and the coding sequence of a marker gene located on the inserted T-DNA (Fobert et al., 1991, Plant Mol. Biol. 17, 837-851).

It has generally been assumed that activation of promoterless or enhancerless marker genes result from T-DNA insertions within or immediately adjacent to genes. The recent isolation of several T-DNA insertional mutants (Koncz et al., 1992, *Plant Mol. Biol.* 20, 963-976; reviewed in Feldmann, 1991, *Plant J.* 1, 71-82; Van Lijsebettens et al., 1991, *Plant Sci.* 80, 27-37; Walden et al., 1991, *Plant J.* 1: 281-288; Yanofsky et al., 1990, *Nature* 346, 35-39), shows that this is the case for at least some insertions. However, other possibilities exist. One of these is that integration of the T-DNA activates silent regulatory sequences that are not associated with genes. Lindsey et al. (1993, *Transgenic Res.* 2, 33-47) referred to such sequences as "pseudo-promoters" and suggested that they may be responsible for activating marker genes in some transgenic lines.

Inactive regulatory sequences that are buried in the genome but with the capability of being functional when positioned adjacent to genes have been described in a variety of organisms, where they have been called "cryptic promoters" (Al-Shawi et al., 1991, *Mol. Cell. Biol.* 11, 4207-4216; Fourel et al., 1992, *Mol. Cell. Biol.* 12, 5336-5344; Irniger et al., 1992, *Nucleic Acids Res.* 20, 4733-4739; Takahashi et al., 1991, *Jpn J. Cancer Res.* 82, 1239-1244). Cryptic promoters can be found in the introns of genes, such as those encoding for yeast actin (Irniger et al., 1992, *Nucleic Acids Res.* 20, 4733-4739), and a mammalian melanoma-associated antigen (Takahashi et al., 1991, *Jpn J. Cancer Res.* 82, 1239-1244). It has been suggested that the cryptic promoter of the yeast actin gene may be a relict of a promoter that was at one time active but lost function once the coding region was assimilated into the exon-intron structure of the present-day gene (Irniger et al., 1992, *Nucleic Acids Res.* 20, 4733-4739). A cryptic promoter has also been found in an untranslated region of the second exon of the woodchuck N-myc proto-oncogene (Fourel et al., 1992, *Mol. Cell. Biol.* 12, 5336-5344). This cryptic promoter is responsible for activation of a N-myc2, a functional processed gene which arose from retropositon of N-myc transcript (Fourel et al., 1992, *Mol. Cell. Biol.* 12, 5336-5344). These types of regulatory sequences have not yet been isolated from plants.

Other regulatory elements are located within the 5' and 3' untranslated regions (UTR) of genes. These regulatory elements can modulate gene expression in plants through a number of mechanisms including translation, transcription and RNA stability. For example, some regulatory elements are known to enhance the translational efficiency of mRNA, resulting in an increased accumulation of recombinant protein by many folds. Some of those regulatory elements contain translational enhancer sequences or structures, such as the Omega sequence of the 5' leader of the tobacco mosaic virus (Gallie and Walbot, 1992, Nucleic Acid res. 20, 4631-4638), the 5' alpha-beta leader of the potato virus X (Tomashevskaya et al, 1993, J. Gen. Virol. 74, 2717-2724), and the 5' leader of the photosystem I gene psaDb of *Nicotiana sylvestris* (Yamamoto et al., 1995, J. Biol. Chem 270, 12466-12470). Other 5' regulatory elements affect gene expression by quantitative enhancement of transcription, as with the UTR of the thylakoid protein genes PsaF, PetH and PetE from pea (Bolle et al., 199, Plant J. 6, 513-523), or by repression of transcription, as for the 5' UTR of the pollen-specific LAT59 gene from tomato (Curie and McCormick, 1997, Plant Cell 9, 2025-2036). Some 3' regulatory regions contain sequences that act as mRNA instability determinants, such as the DST element in the Small Auxin-Up RNA (SAUR) genes of soybean and *Arabidopisis* (Newman et al., 1993, Plant Cell 5, 701-714). Other translational enhancers are also well documented in the literature (e.g. Helliwell and Gray 1995, Plant Mol. Bio. vol 29, pp. 621-626; Dickey L. F. al. 1998, Plant Cell vol 10, 475-484; Dunker B. P. et al. 1997 Mol. Gen. Genet. vol 254, pp. 291-296). However, there have been no reports of these types of cryptic regulatory elements, nor have any cryptic regulatory elements of this kind been isolated from plants.

The present invention discloses transgenic plants generated by tagging with a promoterless GUS (-glucuronidase) T-DNA vector and the isolation and characterization of cryptic regulatory elements identified using this protocol. Cloning and characterization of these insertion sites uncovered unique cryptic regulatory elements not conserved among related species. In one of the plants of interest, GUS expression was spatially and developmentally regulated with in seed tissue. The isolated regulatory element specific to this tissue has not been previously isolated or characterized in any manner. In another plant, a novel constitutive regulatory element was identified that is expressed in tissues throughout the plant and across a broad range of plant species. Furthermore, novel non-translated 5' sequences have been identified that function as post transcriptional regulatory elements.

SUMMARY OF INVENTION

This invention relates to cryptic regulatory elements within plants.

Several transgenic tobacco plants, including T218 and T1275, were identified using the method of this invention that contain novel regulatory elements. These regulatory elements were found not to be active in the native plant.

Plant T218 contains a 4.65 kb EcoRI fragment containing the 2.15 kb promoterless GUS-nos gene and 2.5 kb of 5' flanking DNA. Deletion of the region approximately between 2.5 and 1.0 kb of the 5' flanking region did not alter GUS expression, as compared to the entire 4.65 kb GUS fusion. A further deletion to 0.5 kb of the 5' flanking site resulted in complete loss of GUS activity. Thus the region between 1.0 and 0.5 of the 5' flanking region of the tobacco DNA contains the elements essential to gene activation. This region is contained within a XbaI-SnaBI restriction site fragment of the flanking tobacco DNA. Expression of a gene operatively associated with the regulatory region was only observed in seed tissues, more specifically seed-coat tissue.

A second transgenic tobacco plant, T1275, contained a 4.38 kb EcoRI/XbaI fragment containing the 2.15 kb promoterless GUS-nos gene and 2.23 kb of 5' flanking tobacco DNA (2225 bp). Expression of the cloned fragment in transgenic tobacco, *N. tabacum* c.v. Petit Havana, SRI and transgenic *B. napus* c.v. Westar was observed in leaf, stem, root, developing seed and flower. By transient expression analysis, GUS activity was also observed in leaf tissue of soybean, alfalfa, *Arabidopsis*, tobacco, *B. napus*, pea and suspension cultured cells of oat, corn, wheat and barley. The transcription start site for the GUS gene in transgenic tobacco was located in the plant DNA upstream of the insertion site. A set of deletions within the plant DNA revealed the presence of a core promoter element located within a 62 bp region from the transcriptional start site, the occurrence of at least one negative regulatory element located within an XbaI-SspI fragment, a transcriptional enhancer located within the BstYI-DraI fragment, and at least one post transcriptional regulatory element located within a NdeI-SmaI fragment.

This invention therefore provides for isolated nucleic acids that comprise cryptic regulatory elements within plants. This invention is also directed to cryptic regulatory elements that comprise at least one of: a promoter, a core promoter element, a negative regulatory element, a transcriptional enhancer, a translational enhancer and a post transcriptional regulatory element.

Furthermore, this invention relates to a cryptic regulatory element comprising a nucleic acid that is substantially homologous to the nucleotide sequence of SEQ ID NO:1. This invention also relates to a nucleic acid comprising at least 19 contiguous nucleotides of nucleotides 1 to 993 of SEQ ID NO:1, or, comprising a nucleotide sequence consisting of at least 19 contiguous nucleotides of nucleotides 1 to 467 of SEQ ID NO:1. This invention also relates to a vector comprising the nucleic acids as defined above.

This invention is also directed to a cryptic regulatory element comprising a nucleic acid fragment bounded by EcoRI-SmaI restriction sites defined by the restriction map of FIG. 2(B). Furthermore, this invention relates to a cryptic regulatory element comprising an XbaI-SmaI fragment, of the restriction map of FIG. 2(B) of about 2 kb. Also considered within the scope of the present invention is a cryptic regulatory element comprising an XbaI and SnaBI fragment as defined by the restriction map of FIG. 2(B), wherein the fragment is of about 500 bp. This invention also is directed to a cryptic regulatory element comprising an XbaI and SnaBI fragment, as defined by the restriction map of FIG. 2(B), wherein the fragment is of about 1.5 kb, or a cryptic regulatory element comprising a HindIII and SnaBI fragment, defined by the restriction map of FIG. 2(B), wherein the fragment is of about 1.9 kb. Furthermore, this invention also embraces a cryptic regulatory element comprising an EcoRI and SnaBI fragment defined by the restriction map of FIG. 2, wherein the fragment is of about 2 kb.

This invention also embraces a regulatory element characterized in that it is substantially homologous with the sequence defined by SEQ ID NO:2. This invention is also directed to a cryptic regulatory element that comprises at least an 18 bp contiguous sequence of SEQ ID NO:2. Furthermore, this regulatory element functions in diverse plant species when introduced on a cloning vector. This invention also relates to a chimeric gene construct comprising a DNA of interest for which constitutive expression is desired, and a constitutive regulatory element, comprising at least an 18 bp contiguous sequence of SEQ ID NO:2.

This invention also embraces a cryptic regulatory element comprising an XbaI-SmaI fragment (comprising nucleotides 1-2224 of SEQ ID NO:2), an XbaI-NdeI fragment (comprising nucleotides 1-1086 of SEQ ID NO:2), an SphI-SmaI fragment (comprising nucleotides 415-2224 of SEQ ID NO:2), a PstI-SmaI fragment (comprising nucleotides 750-2224 of SEQ ID NO:2), an SspI-SmaI fragment (comprising nucleotides 1370-2224 of SEQ ID NO:2), a BstYI-SmaI fragment (comprising nucleotides 1660-2224 of SEQ ID NO:2), a DraI-SmaI fragment (comprising nucleotides 1875-2224 of SEQ ID NO:2), a NdeI-SmaI fragment (comprising nucleotides 2084-2224 of SEQ ID NO:2), a XbaI-BstYI fragment (comprising nucleotides 1-1660 of SEQ ID NO:2), a BstYI-DraI fragment (comprising nucleotides 1660-1875 of SEQ ID NO:2), a 1 to Sma1 fragment (comprising nucleotides 2055-2224 of SEQ ID NO:2), Dra1-Nde1 fragment (comprising nucleotides 1875-2084 of SEQ ID NO:2) or a Dra1 to -62 fragment (comprising nucleotides 1875-1992 of SEQ ID NO:2) as defined in FIG. 13(C).

This invention is also also directed to a cryptic regulatory element comprising nucleotides 1-141 of SEQ ID NO:3, nucleotides 1-188 of SEQ ID NO:3, nucleotides 1-97 of SEQ ID NO:4, nucleotides 1-129 of SEQ ID NO:4, nucleotides 1-119 of SEQ ID NO:5, or nucleotides 1-86 of SEQ ID NO:5.

This invention also pertains to a transgenic host organism containing a cryptic regulatory element as defined above operatively linked to a gene encoding a protein. The host organism may be selected from the group consisting of a plant, a tree, an insect, a fungi, a bacteria, a yeast and a non-human animal.

This invention also includes a plant cell which has been transformed with a chimeric gene construct, or a cloning vector comprising a cryptic plant regulatory element. Furthermore, this invention embraces transgenic plants containing chimeric gene constructs, or cloning vectors comprising cryptic plant regulatory elements.

This invention further relates to any transgenic plant containing a cryptic regulatory element, having a DNA sequence substantially homologous to SEQ ID NO:1, or SEQ ID NO:2 and operatively linked to a DNA region that is transcribed into RNA.

Also included in the present invention is a method of conferring expression of a gene in a host organism, comprising operatively linking an exogenous DNA of interest, for which expression is desired with a cryptic regulatory element as defined above, to produce a chimeric gene construct, and introducing the chimeric gene construct into the host organism capable of expressing the chimeric gene construct. This invention also embraces a method of modulating expression of a gene in a plant, comprising operatively linking an exogenous DNA of interest, for which expression is desired with a promoter of interest and the cryptic regulatory element as defined above and introducing the chimeric construct into the host organism. Furthermore, the method of conferring or modulating gene expression may include operatively linking an exogenous DNA of interest, for which expression is desired with a promoter of interest and at least one fragment of the cryptic regulatory element as defined above to produce a chimeric gene construct, and introducing the chimeric gene construct into the host organism capable of expressing the chimeric gene construct. The host organism may be selected from the group consisting of a plant, a tree, an insect, a fungi, a bacteria, a yeast and a non-human animal.

This invention also relates to the above method wherein the plant-derived cryptic regulatory element is a seed-coat specific or constitutive regulatory element. Furthermore, this invention embraces the above method wherein the seed-coat specific regulatory element comprises a nucleic acid that is substantially homologous with the sequence of SEQ ID NO:1, or constitutive regulatory element comprises a nucleic acid that is substantially homologous with the sequence of SEQ ID NO:2. This invention also relates to the above method wherein the nucleic acid comprises at least a 19 bp contiguous sequence of SEQ ID NO:1, or the nucleic acid comprises at least an 18 bp contiguous sequence of SEQ ID NO:2.

According to the present invention there is also provided a seed coat-specific cryptic regulatory element contained within a DNA sequence, or analogue thereof, as shown in SEQ ID NO:1. Furthermore, there is provided a constitutive regulatory element contained within a DNA sequence, fragment or an analogue thereof, as shown in SEQ ID NO:2.

This invention also relates to a vector containing a seed coat-specific cryptic regulatory element, which is contained within a DNA sequence, or analogue thereof, as shown in SEQ ID NO:1 and a gene encoding a protein. This invention also relates to a cloning vector containing a constitutive cryptic regulatory element, which is contained within a DNA sequence, fragment, or an analogue thereof, as shown in SEQ ID NO:2 and a gene encoding a protein.

This invention also includes a plant cell which has been transformed with a vector as described above, and to a transgenic plant containing a cloning vector as described above, operatively linked to a gene encoding a protein.

BRIEF DESCRIPTION OF THE DRAWINGS

FIG. 2 shows the cloning of the GUS fusion in plant T218 (pT218) and construction of transformation vectors. Plant DNA is indicated by the solid line and the promoterless GUS-nos gene is indicated by the open box. The transcriptional start site and presumptive TATA box are located by the closed and open arrow heads respectively.

FIG. 5 shows the mapping of the T218 GUS fusion termini and expression of the region surrounding the insertion site in untransformed plants. FIG. 5(A) shows the mapping of the GUS mRNA termini in plant T218. The antisense RNA probe from subclone #4 (FIG. 2) was used for hybridization with total RNA of tissues from untransformed plants (10 μg) and from plant T218 (30 μg). Arrowheads indicate the anticipated position of protected fragments if transcripts were initiated at the same sites as the T218 GUS fusion. FIG. 5(B) shows the results of an RNase protection assay using the antisense (relative to the orientation of the GUS coding region) RNA probe from subclone e (see FIG. 7) against 30 μg total RNA of tissues from untransformed plants. The abbreviations used are as follows: P, untreated RNA probe; -, control assay using the probe and tRNA only; L, leaves from untransformed plants; 8, 10, 12, seeds from untransformed plants at 8, 10, and 12 dpa, respectively; T10, seeds of plant T218 at 10 dpa; +, control hybridization against unlabelled in vitro-synthesized sense RNA from subclone c (panel a) or subclone e (panel b). The two hybridizing bands near the top of the gel are end-labelled DNA fragment of 3313 and 1049 bp, included in all assays to monitor losses during processing. Molecular weight markers are in number of bases.

FIG. 6 provides the nucleotide sequence of pT218 (top line) (SEQ ID NO:1) and pIS-1 (bottom line). Sequence identity is indicated by dashed lines. The T-DNA insertion site is indicated by a vertical line after bp 993. This site on pT218 is immediately followed by a 12 bp filler DNA, which is followed by the T-DNA. The first nine amino acids of the GUS gene and the GUS initiation codon (*) are shown. The major and minor transcriptional start site is indicated by a large and small arrow, respectively. The presumptive TATA box is identified and is in boldface. Additional putative TATA and CAAT boxes are marked with boxes. The location of direct (1-5) and indirect (6-8) repeats are indicated by arrows.

Figure 2A:
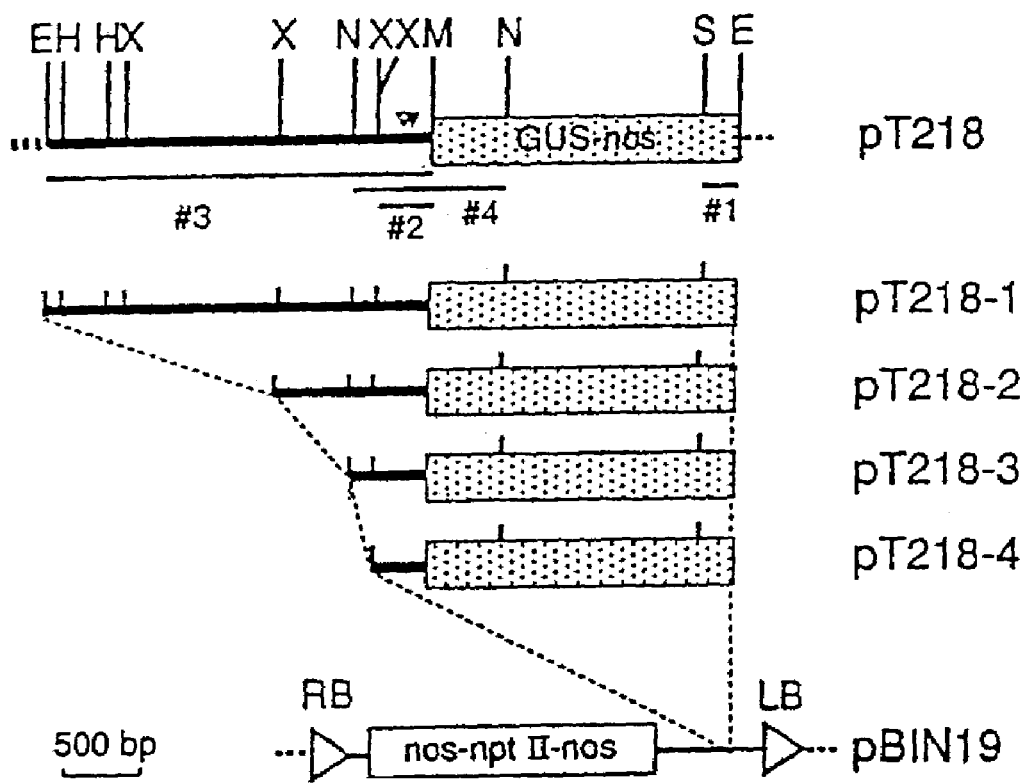
FIG. 2(A) shows DNA probes # 1, 2, 3, and RNA probe #4 (all listed under the pT218 restriction map). The EcoRI fragment in pT218 was subcloned in the pBIN19 polylinker to create pT218-1. Fragments truncated at the XbaI, SnaBI and XbaI sites were also subcloned to create pT218-2, pT218-3 and pT218-4.
Figure 2B:
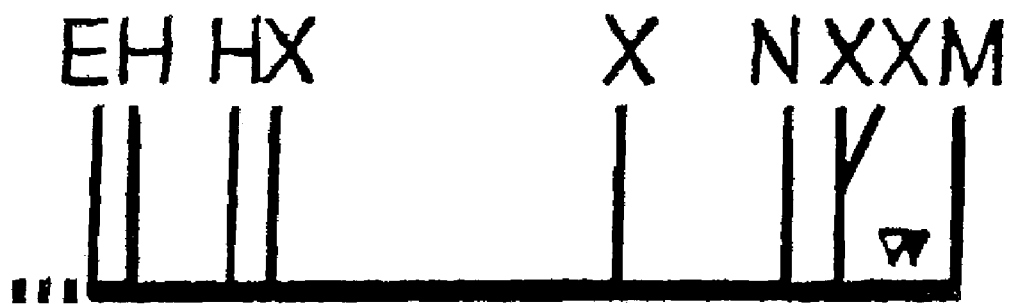
FIG. 2(B) shows the restriction map of the plant DNA upstream from the GUS insertion site. Abbreviations for the endonuclease restriction sites are as follows: EcoRI (E), HindIII (H), XbaI (X), SnaBI (N), SmaI (M), SstI(S).
Figure 8:
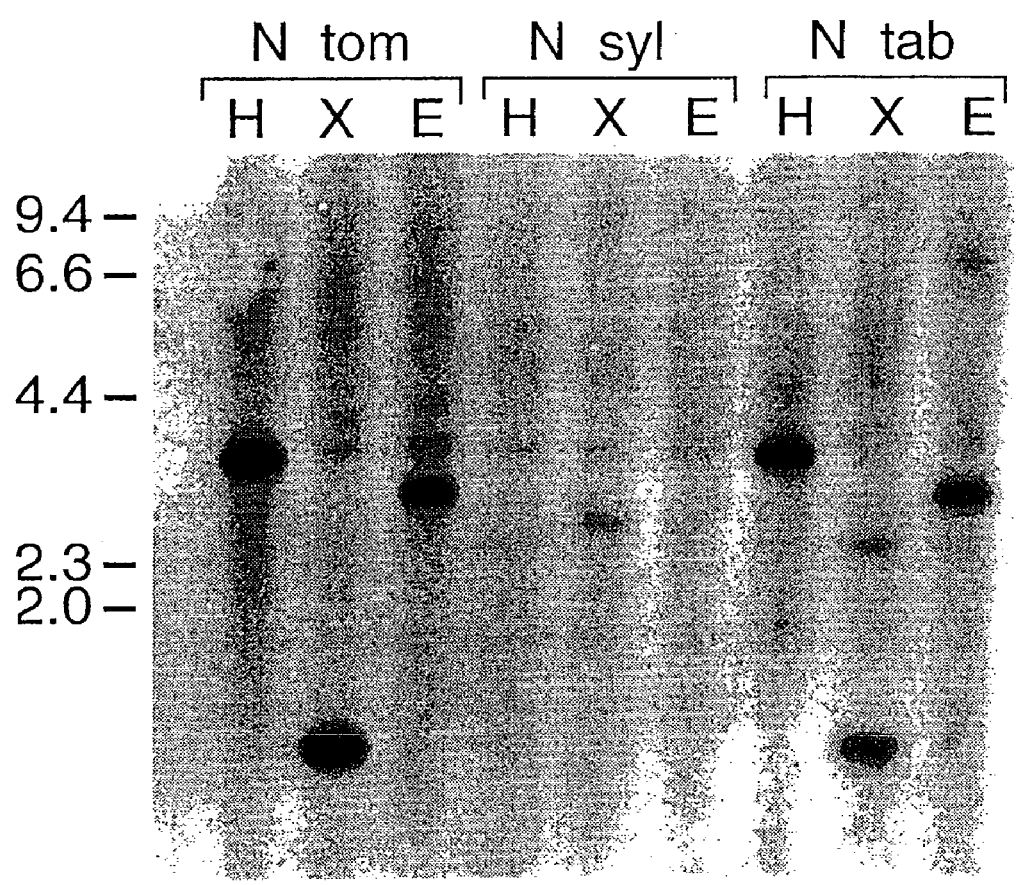

FIG. 8 shows the Southern blot analyses of the insertion site in *Nicotiana* species. DNA from *N. tomentosiformis* (N tom), *N. sylvestris* (N syl), and *N. tabacum* (N tab) were digested with HindIII (H), XbaI (X) and EcoRI (E) and hybridized using probe #2 (FIG. 2). Lambda HindIII markers (kb) are indicated.

Figure 9:
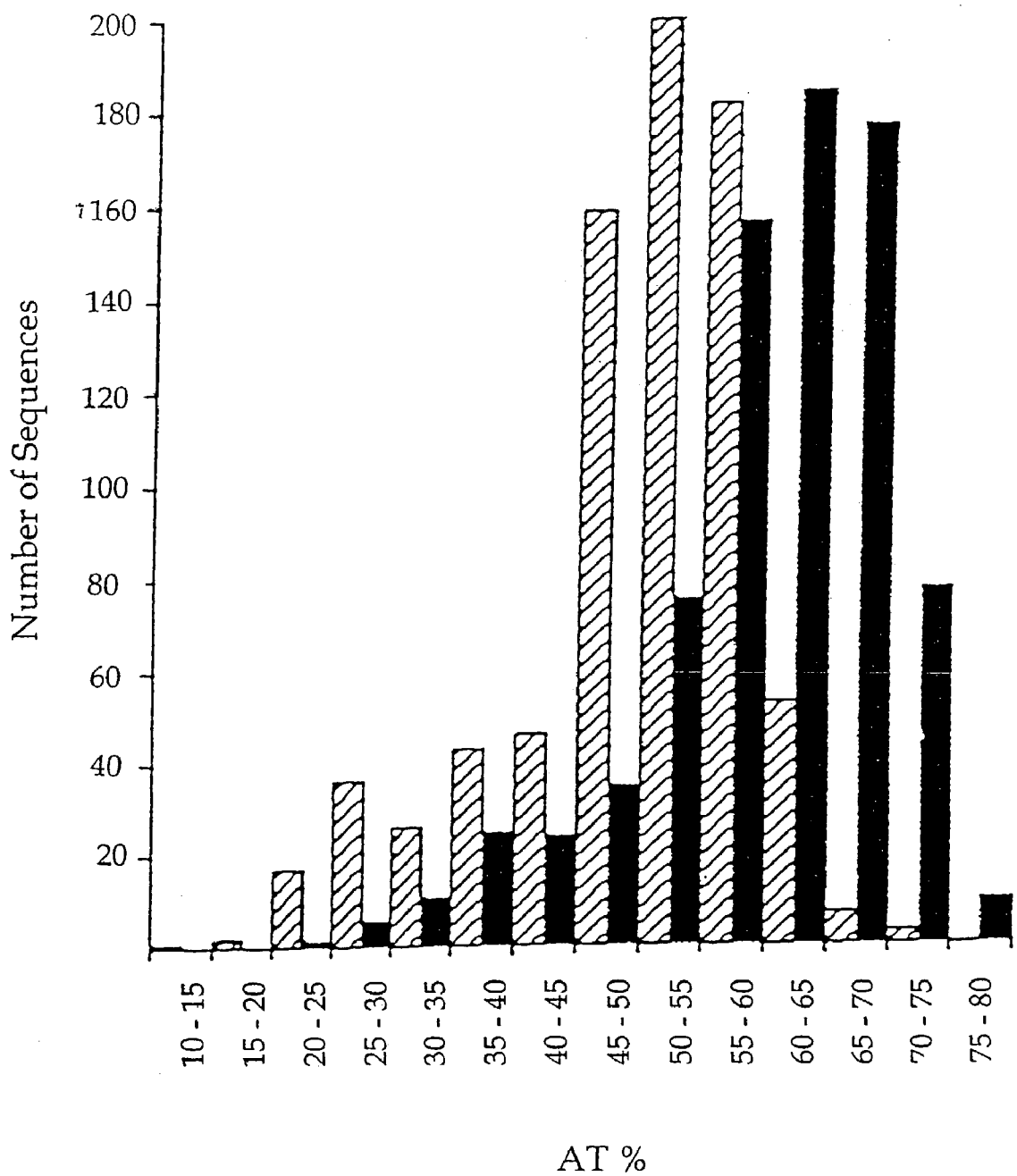

FIG. 9 shows the AT content of 5' non-coding regions of plant genes. A program was written in PASCAL to scan GenBank release 75.0 and to calculate the AT contents of the 5' non-coding (solid bars) and the coding regions (hatched bars) of all plant genes identified as "Magnoliophyta" (flowering plants). The region −200 to −1 and +1 to +200 were compared. Shorter sequences were also accepted if they were at least 190 bp long. The horizontal axis shows the ratio of the AT content (%). The vertical axis shows the number of the sequences having the specified AT content ratios.

Figure 10A:
Figure 10B:
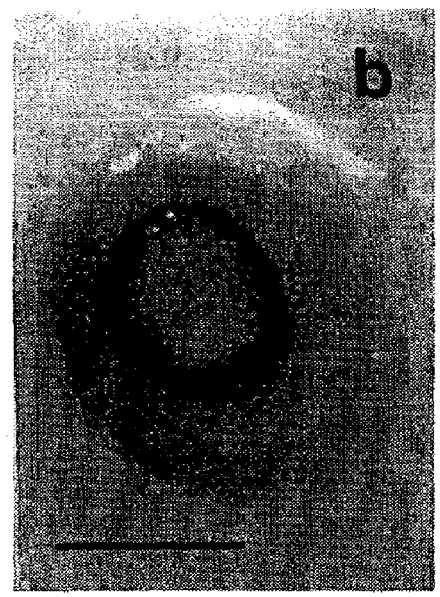
Figure 10C:
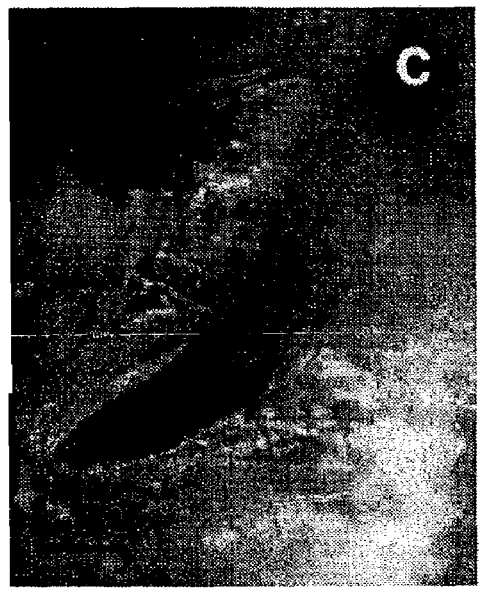
Figure 10D:
Figure 10E:
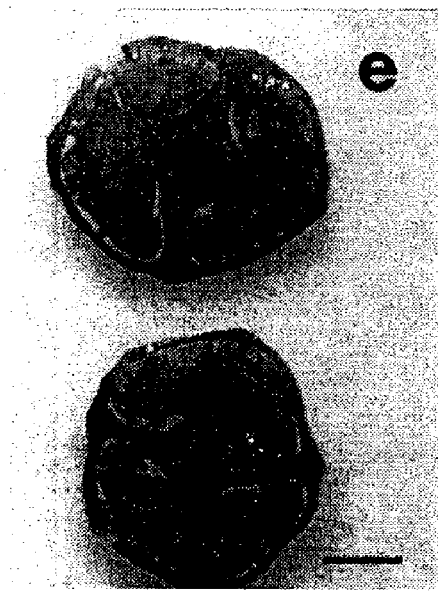
Figure 10F:
Figure 10:
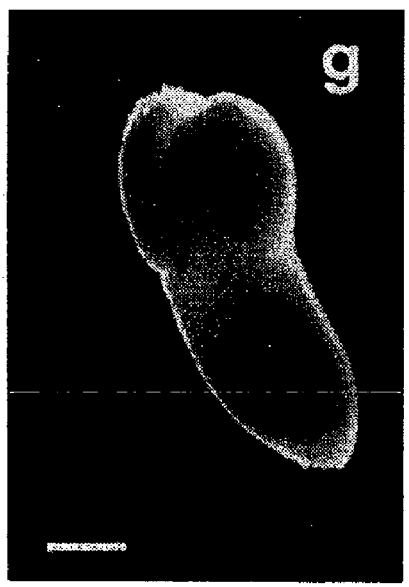
Figure 10H:
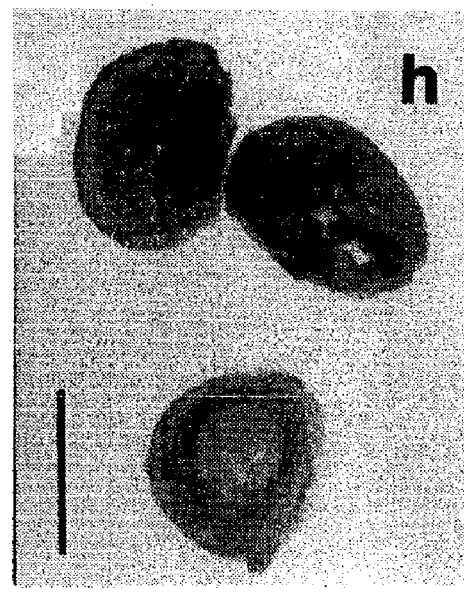

FIG. 10 shows the constitutive expression of GUS in all tissues of plant T1275, including leaf segments (a), stem cross-sections (b), roots (c), flower cross-sections (d), ovary cross-sections (e), immature embryos (f), mature embryos (g), and seed cross-sections (h).

Figure 11:
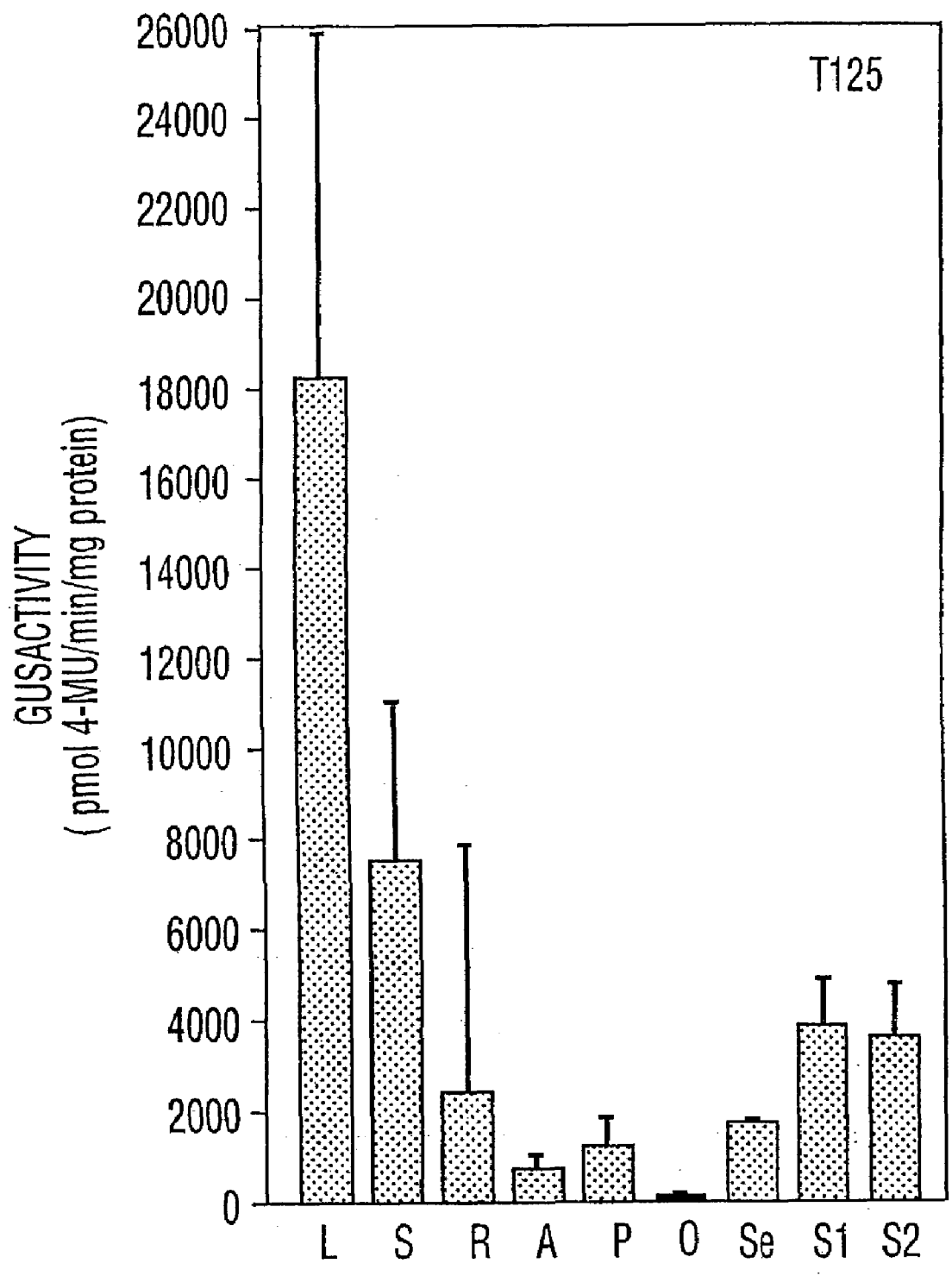

FIG. 11 shows GUS specific activity within a variety of tissues throughout the plant T1275, including leaf (L), stem (S), root (R), anther (A), petal (P), ovary (O), sepal (Se), seeds 10 days post anthesis (S1), and seeds, 20 days post anthesis (S2).

FIG. 12 shows the restriction map of the cryptic regulatory element of pT1275. FIG. 12(A) shows the plant DNA fused with GUS. FIG. 12(B) shows the restriction map of the plant DNA. The arrow indicates the GUS mRNA start site within the cryptic regulatory region.

FIG. 13 shows deletion constructs of the T1275 regulatory element. FIG. 13(A) shows the 5' endpoints of each construct as indicated by the restriction endonuclease site, relative to the full length T1275 regulatory element, the arrow indicates the transcriptional start site. Plant DNA is indicated by the solid line, the promoterless GUS-nos gene is indicated by the open box and the shaded box indicates the region coding for the amino terminal peptide fused to GUS. The XbaI fragment in pT1275 was subcloned to create pT1275-GUS-nos. Deletion constructs truncated at the SphI, PstI, SspI, BstYI, and DraI sites were also subcloned to create −1639-GUS-nos, −1304-GUS-nos, −684-GUS-nos, −394-GUS-nos, and −197-GUS-nos, respectively. FIG. 13(B) shows further deletion constructs of −62-GUS-nos, −12-GUS-nos, −62(-tsr)GUS-nos and +30-GUS-nos, relative to −197-GUS-nos (see FIG. 13(A)). FIG. 13(C) shows the restriction map of the plant DNA of pT1275 upstream from the GUS insertion site. FIG. 13(D) shows modified constructs of the T1275 regulatory elements. T1275 is indicated by the open box, the CaMV35S promoter element is indicated by the black box. The activity of these constructs is also indicated. GUS activity was determined in tobacco leaves following transient expression using microparticle bombardment. TA30-GUS: a TATATAA element was inserted into the −30 position of −62-GUS; TA35S-GUS: the −62 to −20 fragment of −62-GUS was substituted with the −46 to −20 fragment of the 35S promoter; GCC-62-GUS: a GCC box was fused with −62-GUS; DRA2-GUS: the −197 to −62 fragment was repeated; BST2-GUS: the −394 to −62 fragment was repeated; −46-35S: 35S minimal promoter; DRAI-35: the −197 to −62 fragment of T1275 was fused with −46-35S; BSTI-35S: the −394 to −62 fragment of T1275 was fused with −46-35S; BST2-35S: two copies of the −394 to −62 fragment of T1275 were fused with −46-35S. FIG. 13(E) shows constructs of the −197 to −62 fragment fused with the 35S minimal promoter. −46-35S: 35S minimal promoter; DRAI-35S: the −197 to −62 fragment of T1275 was fused with −46-35S; DRA1R-35S: the −197 to −62 fragment of T1275 was fused with −46-35S in a reversed orientation; DRA2-35S: two copies of the −197 to −62 fragment of T1275 were fused with −46-35S. FIG. 13(F) shows GUS specific activity of transgenic *Arabidopsis* plants. Leaf tissues from *Arabidopsis* plants transformed with −47-35S, DRA1-35S, DRA1R-35S and DRA2-35S constructs were used for GUS assay. FIG. 13(G) shows the constitutive expression of GUS in *Arabidopsis* plants transformed with DRA1-35S. From left to right: flower, silque and seedling.

Figure 14A:
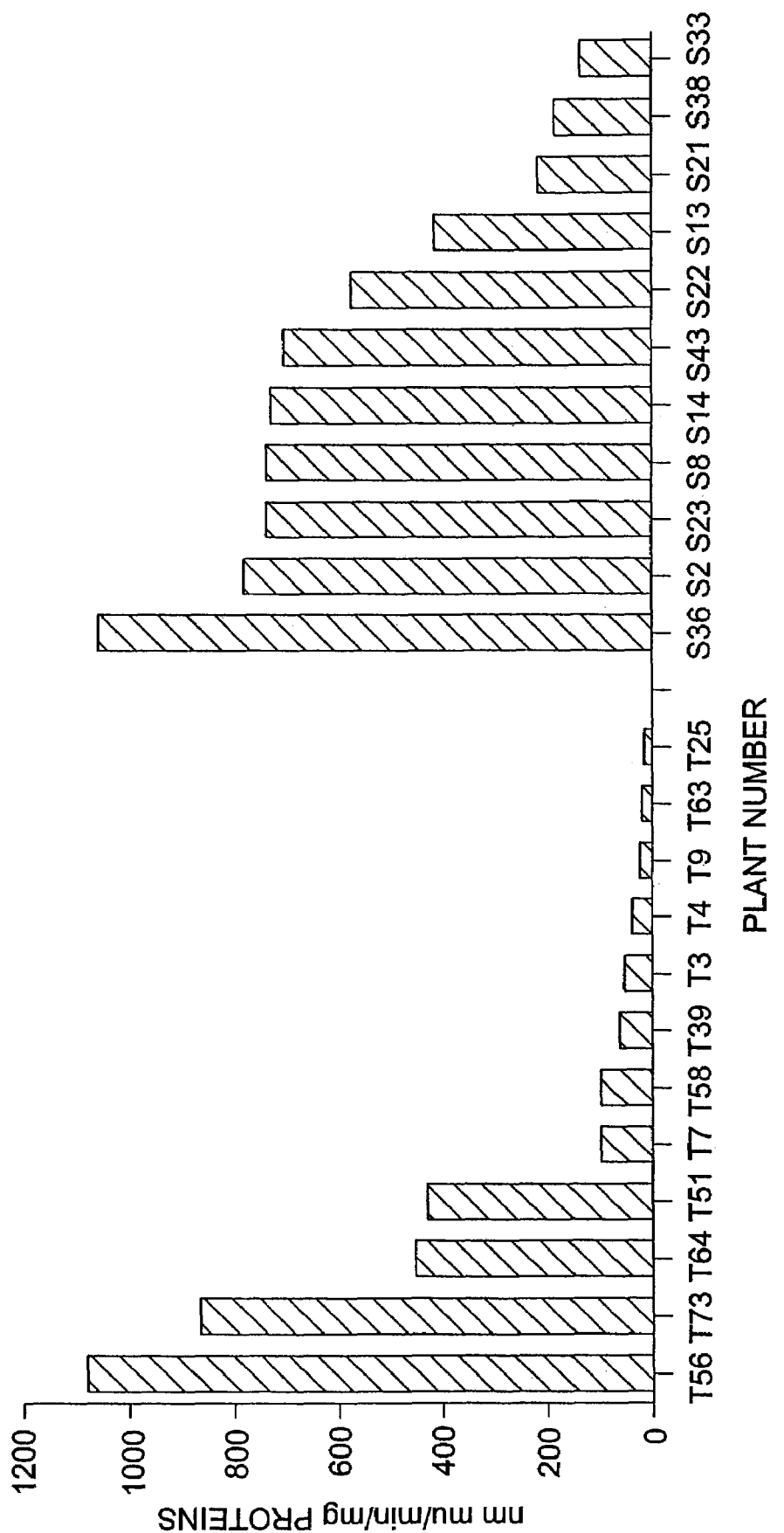
Figure 14B:
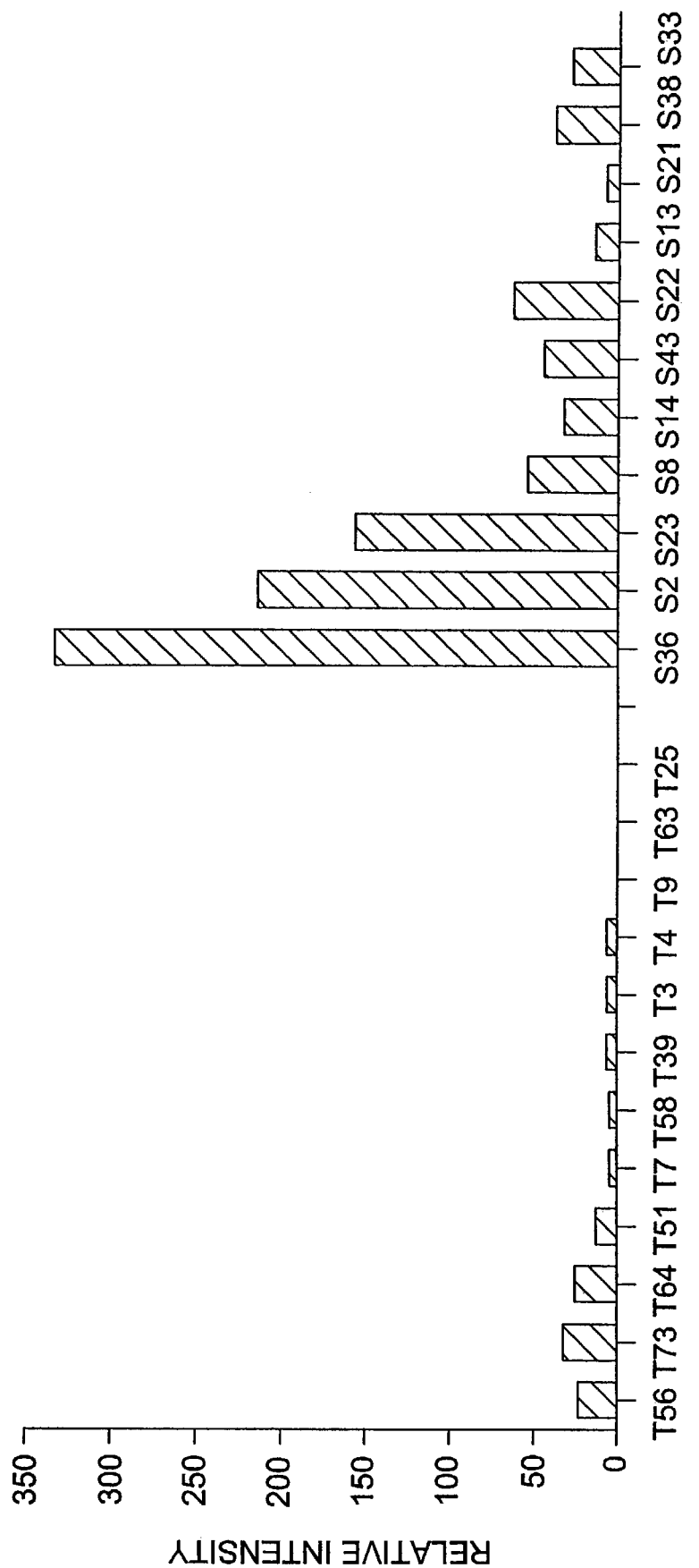
Figure 14C:
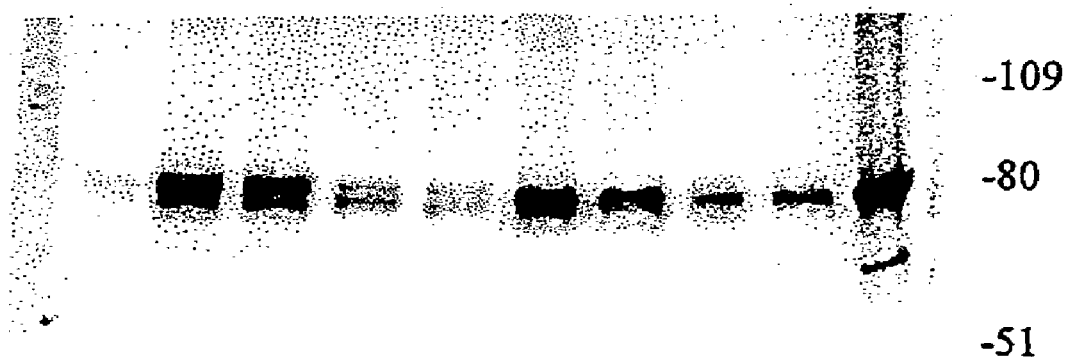

FIG. 14 shows the GUS specific activity, mRNA, and protein levels in leaves of individual, regenerated, greenhouse-grown transgenic plants containing T1275-GUS-nos (T plants), or 35S-GUS-nos (S plants). FIG. 14 (A) shows the levels of GUS expression in leaves from randomly selected plants containing either T1275-GUS-nos (left-hand side) or 35S-GUS-nos (right-hand side). FIG. 14(B) shows the level of accumulated GUS mRNA measured by RNase protection assay and densitometry of autoradiograms in leaves from the same randomly selected plants containing either T1275-GUS-nos (left-hand side) or 35S-GUS-nos (right-hand side). FIG. 14(C) shows a Western blot of GUS fusion protein obtained from T1275-GUS-nos and 35S-GUS-nos plants. Leaf extracts were equally loaded onto gels and GUS was detected using anti-GUS antibodies. The molecular weight markers are indicated on the right-hand side of the gel; untransformed control (SR1) and GUS produced in *E. coli* (Ec).

Figure 15:
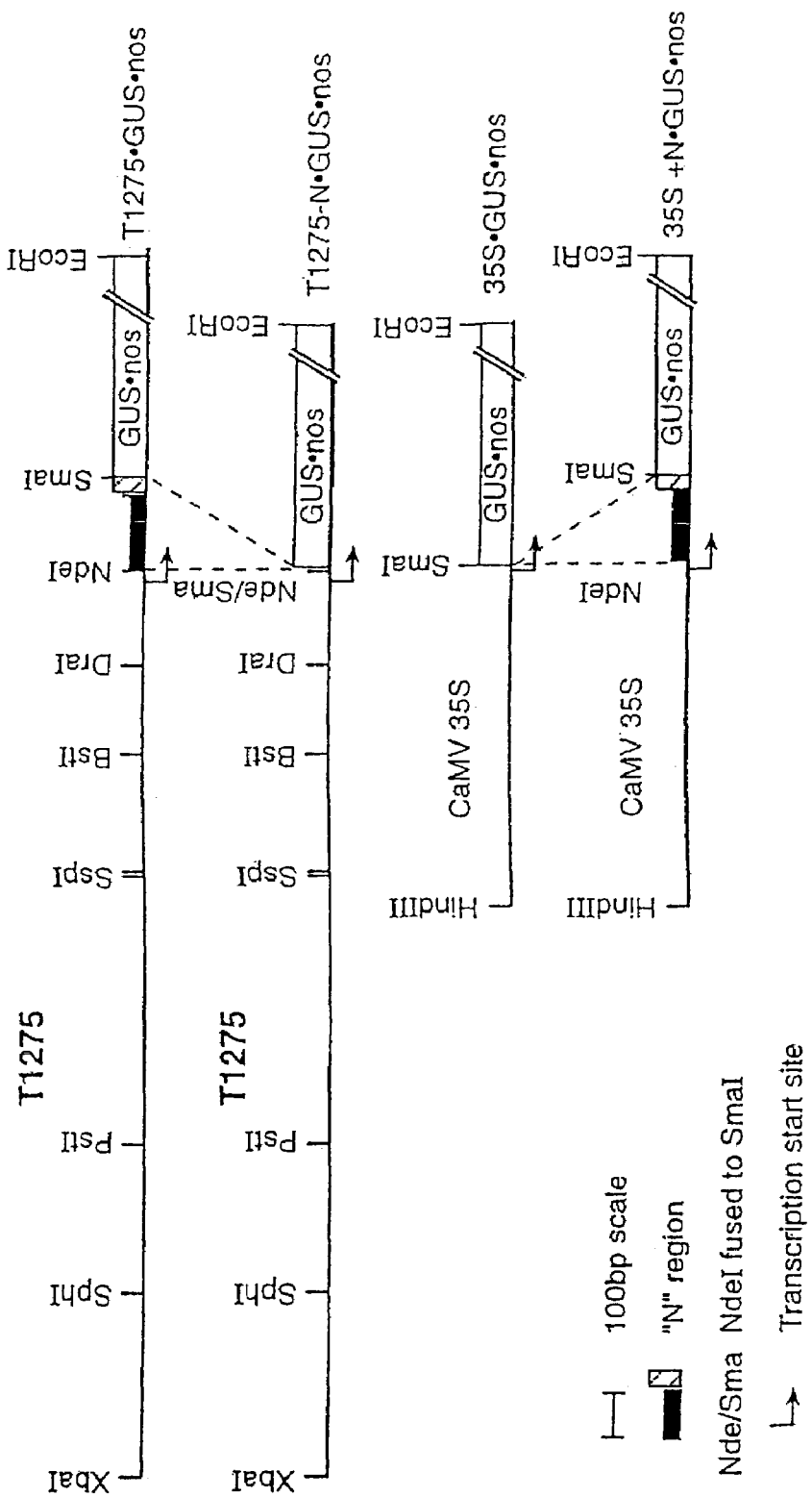

FIG. 15 shows deletion and insertion constructs of the 5' untranslated leader region of T1275 regulatory element and construction of transformation vectors. The constructs are presented relative to T1275-GUS-nos or 35S-GUS-nos. The arrow indicates the transcriptional start site. Plant DNA is indicated by the solid line labeled T1275, the 35S regulatory region by the solid line labelled CaMV35S, the NdeI-SmaI region by a filled in box, the shaded box coding for the amino terminal peptide, and the promoterless GUS-nos gene is indicated by an open box. The deletion construct removing the NdeI-SmaI fragment of T1275-GUS-nos is identified as T1275−N-GUS-nos. The NdeI-SmaI fragment from T1275-GUS-nos was also introduced into 35S-GUS-nos to produce 35S+N-Gus-nos.

Figure 16A:
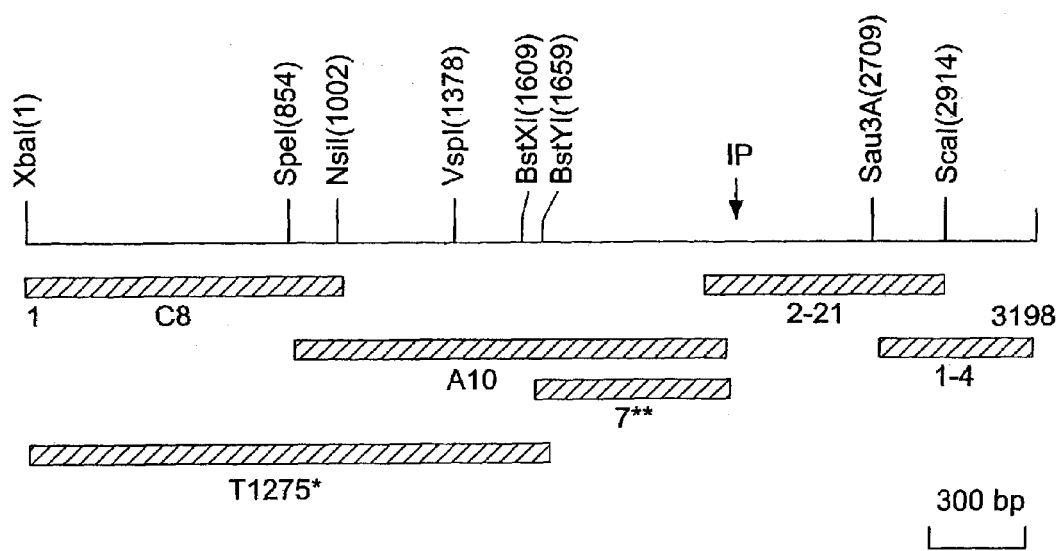
Figure 16B:
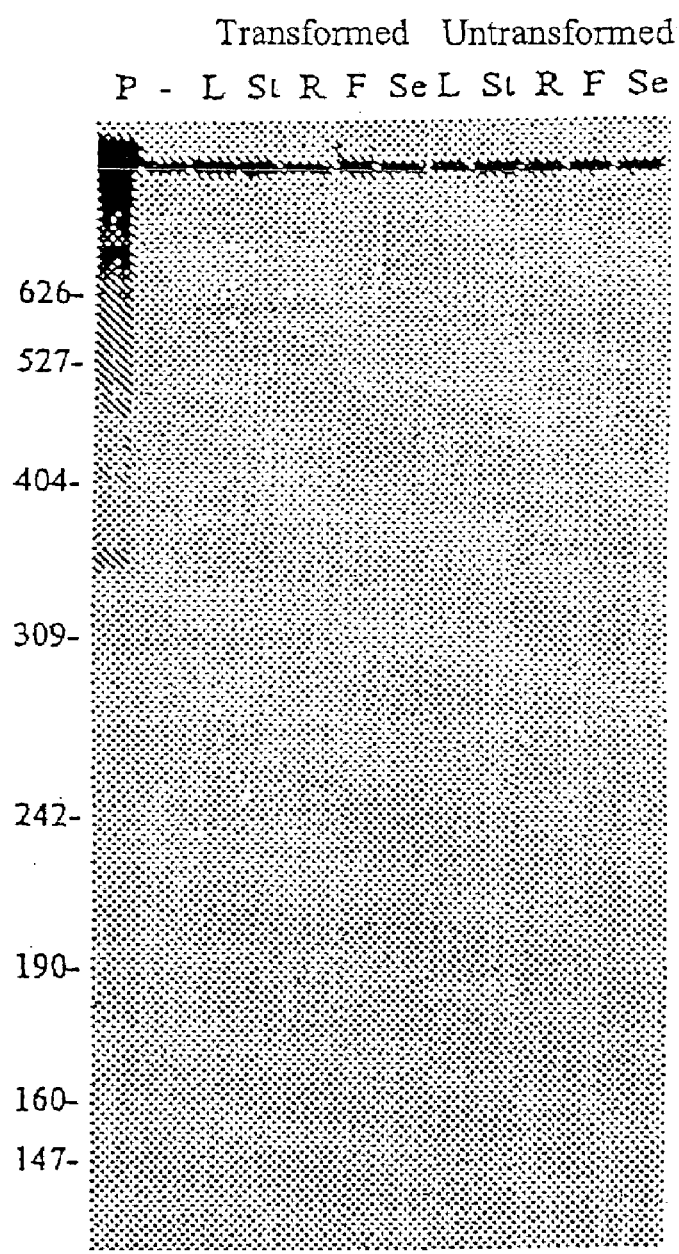

FIG. 16 shows the region surrounding the insertion site in untransformed plants, positions of various probes used for RNase protection assays, and results of the RNase protection assay. FIG. 16(A) shows a restriction map of the insertion site and various probes used for the assay (IP: insertion point of GUS in transformed plants; *: that T1275 probe ended at the BstYI site, not the IP; **: probe 7 included 600 bp of the T1275 plant sequence and 400 bp of the GUS gene). FIG. 16(B) shows results of an RNase protection assay of RNA isolated from leaf (L), stem (St), root (R), flower bud (F) and developing seed (Se) tissues of tobacco transformed with T1275-GUS-nos (10 μg RNA) and untransformed tobacco (30 μg RNA). Undigested probe (P), tRNA negative control (−) lanes and markers are indicated. RNase protection assays shown used a probe to detect sense transcripts between about −446 and +596 of T1275-GUS-nos or between about −446 to +169 of untransformed tobacco. The protected fragment in transformed plants is about 596 bp (upper arrowhead) and, if present, accumulated transcripts initiated at this site in untransformed plants are predicted to protect a fragment of about 169 bp (lower arrowhead). Upper band in RNA-containing lanes was added to samples to indicate loss of sample during assay.

Figure 17A:
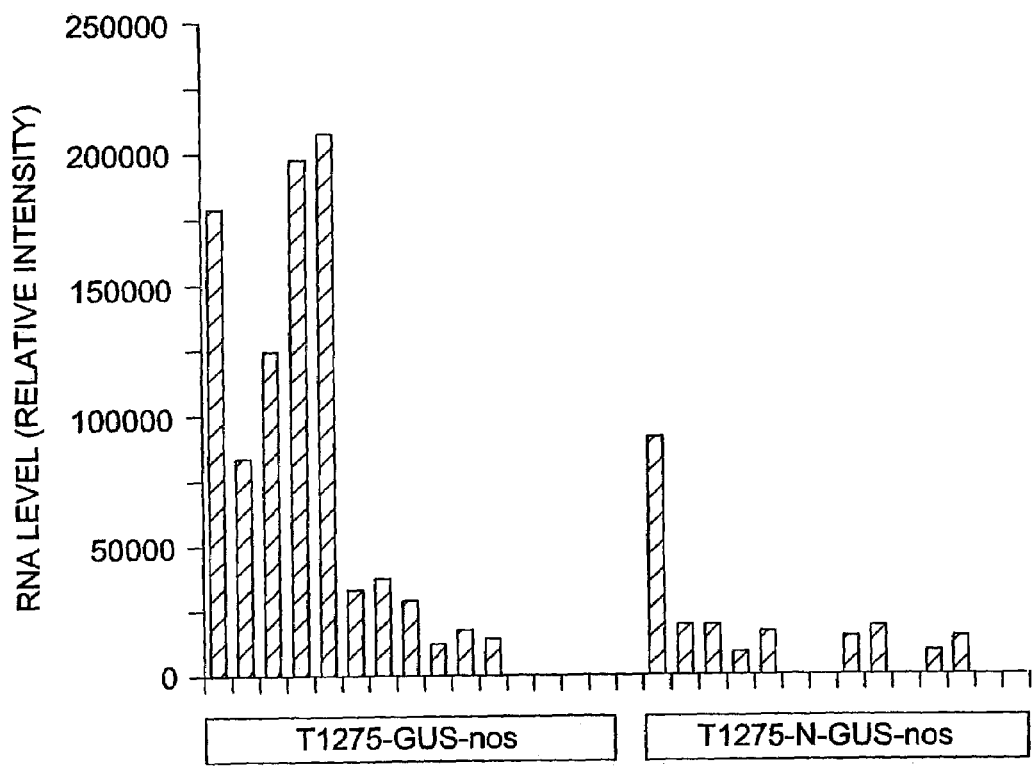
Figure 17B:
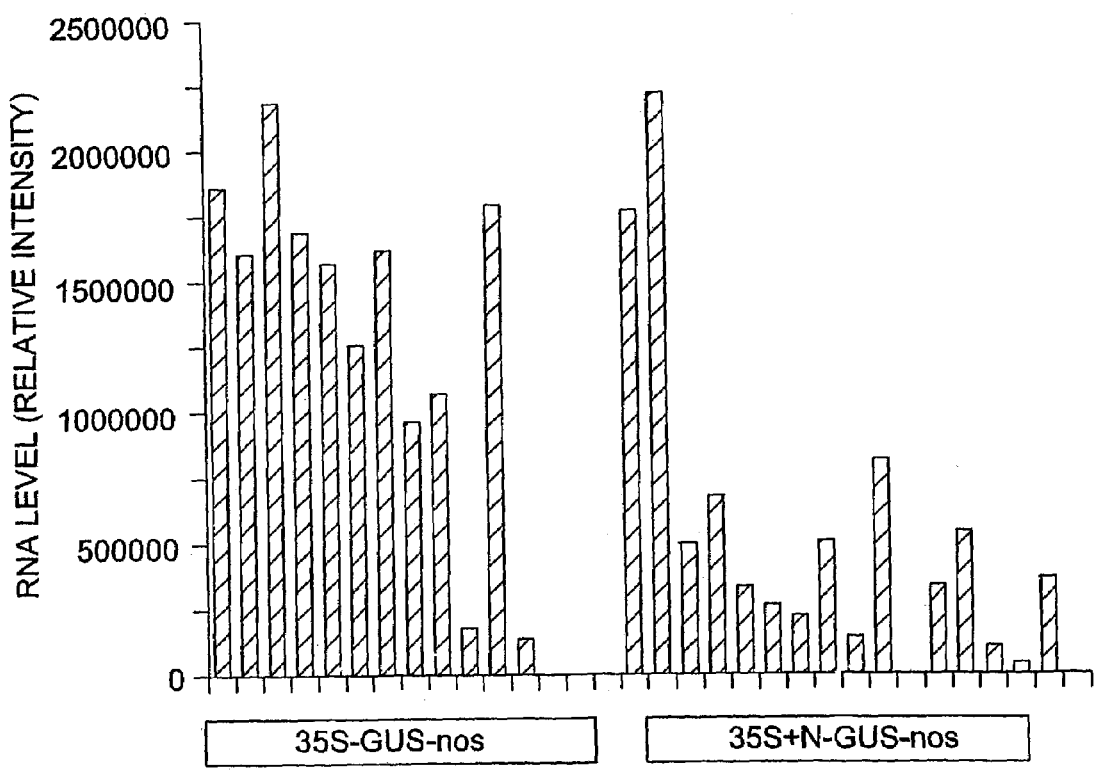
Figure 17C:
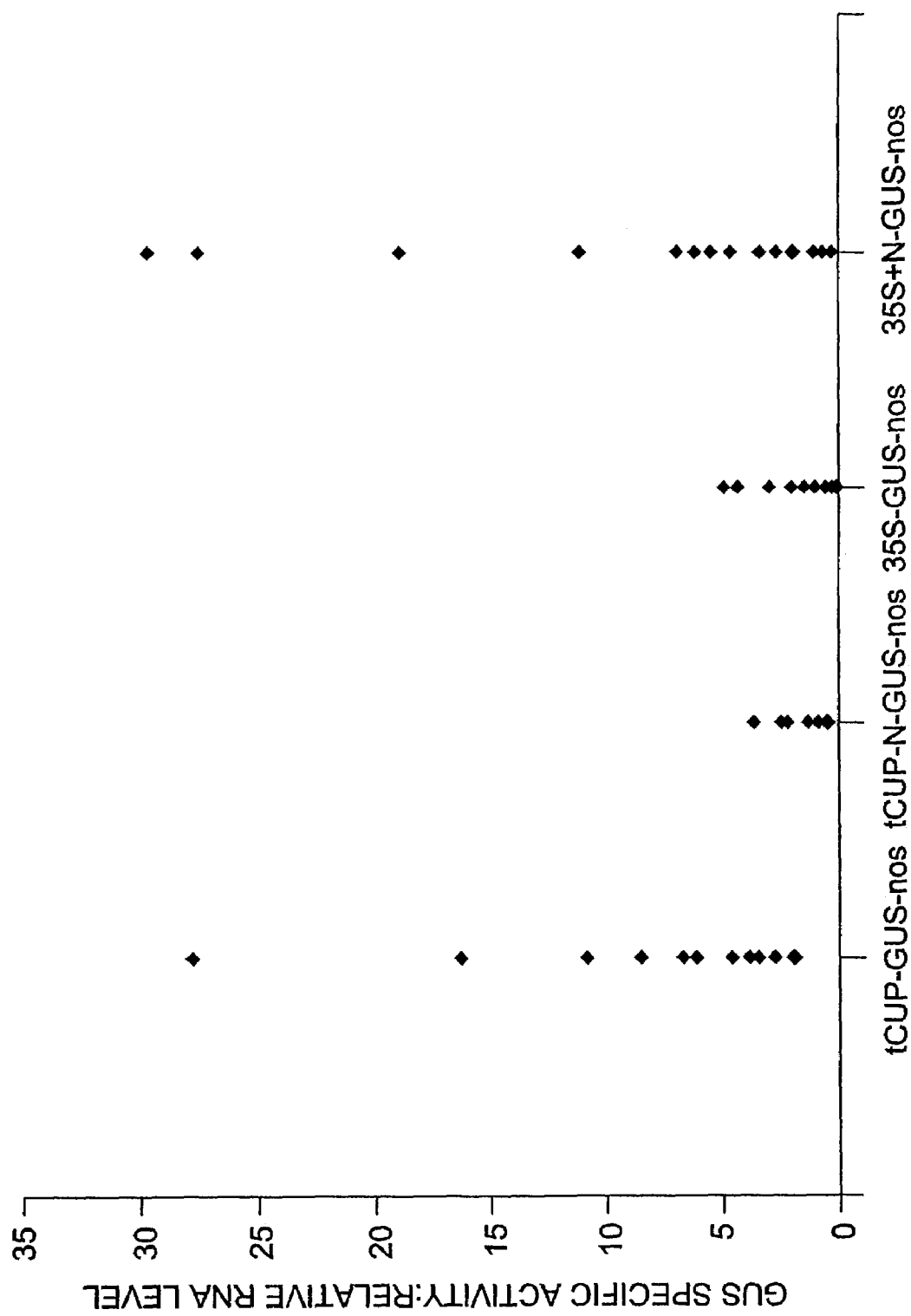

FIG. 17 shows the levels of mRNA, as well as the ratio between GUS specific activity and mRNA levels in leaves of individual, regenerated, greenhouse-grown transgenic plants containing T1275-GUS-nos, or 35S-GUS-nos constructs, with or without the NdeI-SmaI fragment (see FIG. 15). FIG. 17(A) shows the level of accumulated GUS mRNA measured by RNase protection assay and densitometry of autoradiograms in leaves from the same randomly selected plants containing either T1275-GUS-nos, T1275–N-GUS-nos. FIG. 17(B) shows the level of accumulated GUS mRNA measured by RNase protection for 35S-GUS-nos or 35S+N-GUS-nos. FIG. 17(C) shows the ratio between GUS specific activity and mRNA levels in leaves of individual, regenerated, greenhouse-grown transgenic plants containing T1275-GUS-nos, T1275–N-GUS-nos, 35S-GUS-nos, or 35S+N-GUS-nos constructs.

Figure 18:
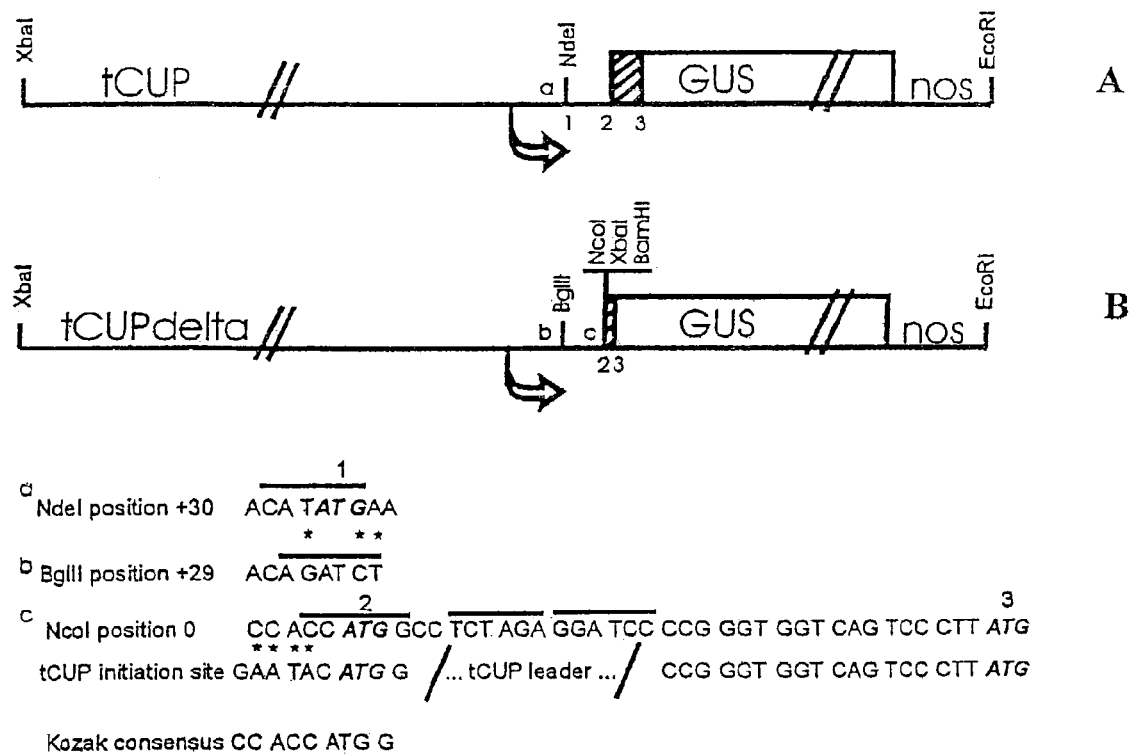

FIG. 18 shows the maps of T1275-GUS-nos and T1275 (N)-GUS-nos. FIG. 18(A) shows T1275-GUS-nos (also referred to as tCUP-GUS-nos). FIG. 18(B) shows T1275 (N)-GUS-nos (also referred to as tCUPdelta-GUS-nos). "ΔN", (also referred to as "dN" or "deltaN") was created by changing the NdeI site "a" in the leader sequence of T1275-GUS-nos (FIG. 18(A)) to a BglII site "b" (see FIG. 18(B)) to eliminate the upstream ATG at nucleotides 2087-2089 or SEQ ID NO:2. A Kozak consensus sequence "c" was constructed at the initiator MET codon and a NcoI site was added. The transcriptional start site, determined for T1275, is indicated by the arrow.

Figure 19:
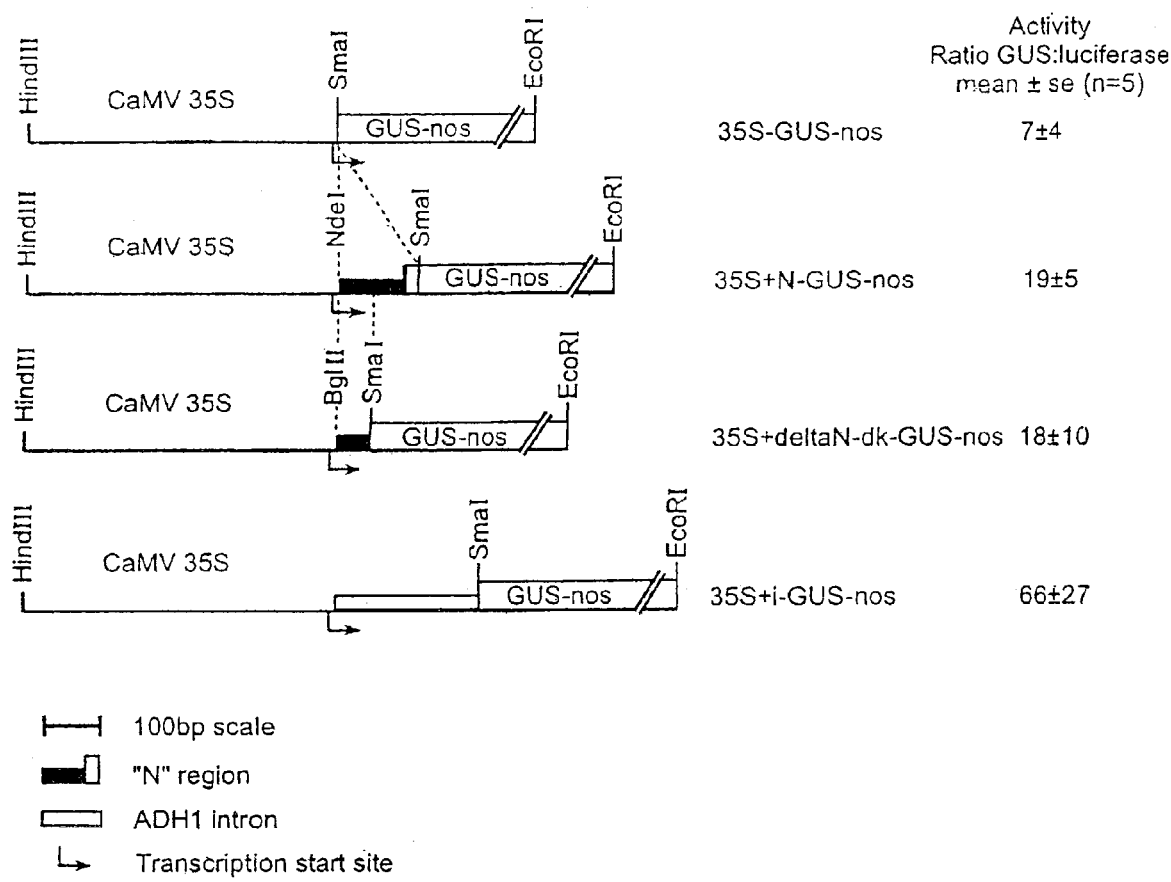

FIG. 19 shows constructs used for the transient expression via particle bombardment of corn callus. Maps for 35S-GUS-nos, 35S (+N)-GUS-nos, 35S (N)-GUS-nos and 35S (+i)-GUS-nos are presented indicating the "N" region, ADH1 intron, and the arrow indicates the transcriptional start site. Note that 35S(N)-GUS-nos is referred to as 35S+deltaN-dK-GUS-nos. Also shown are the associated activities of the constructs in the callus expressed as a ratio of GUS to luciferase (control) activity.

Figure 20:
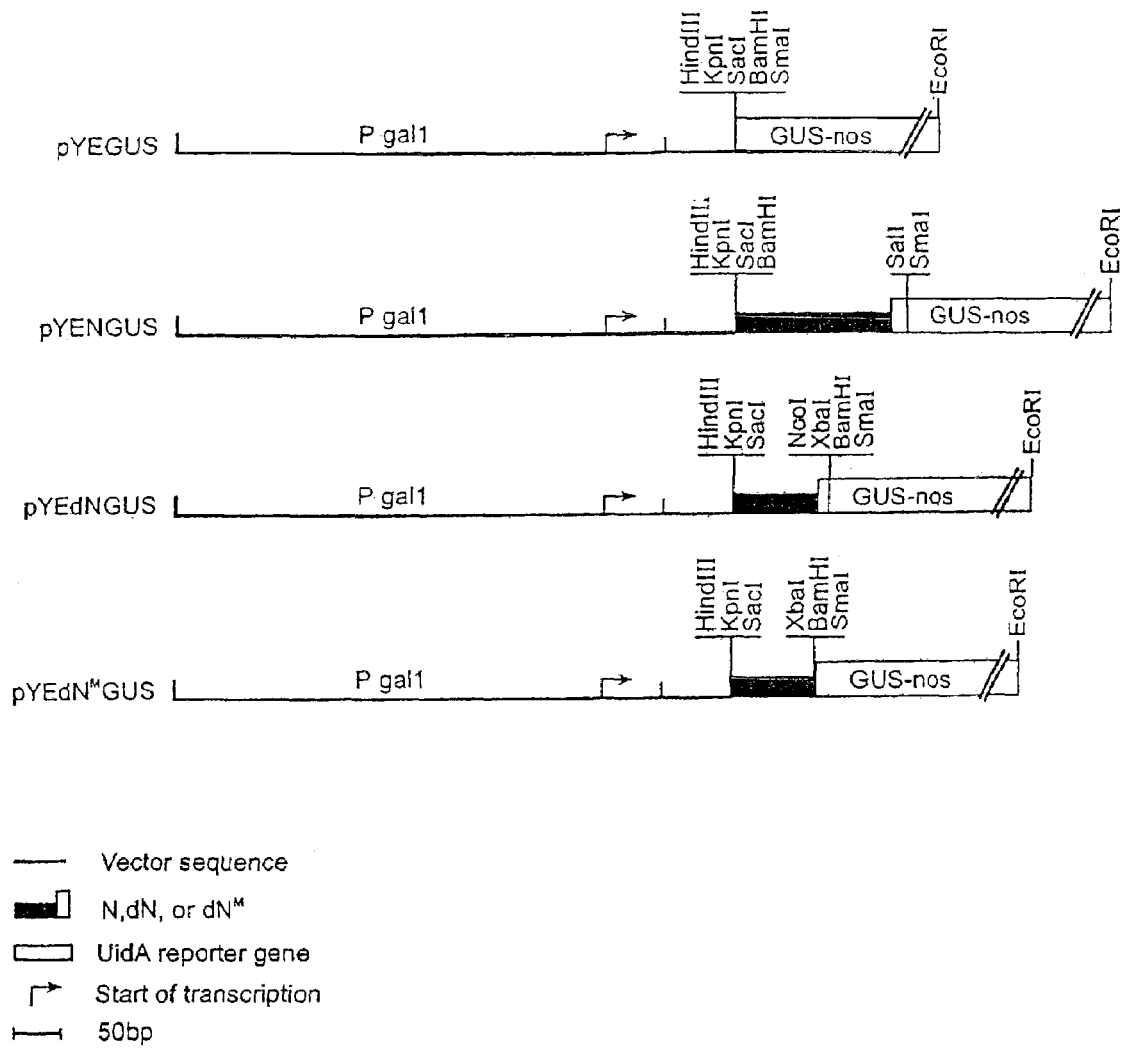

FIG. 20 shows maps of the constructs used for transient expression in yeast. Shown are pYES-GUS-nos (also referred to as pYEGUS); pYES(+N)-GUS-nos (also referred to as pYENGUS); pYES(N)-GUS-nos (also referred to as pYEdNGUS) and pYES($N^M$)-GUS-nos (also referred to as pYEdN$^M$GUS), which lacks the Kozak consensus sequence.

DETAILED DESCRIPTION OF THE PREFERRED EMBODIMENTS

This invention relates to cryptic regulatory elements identified in plants. More specifically, this invention relates to cryptic promoters, negative regulatory elements, transcriptional enhancer elements and other post transcriptional regulatory elements identified in plants.

T-DNA tagging with a promoterless β-glucuronidase (GUS) gene generated several transgenic *Nicotiana tabacum* plants that expressed GUS activity. Examples, which are not to be considered limiting in any manner, of transgenic plants displaying expression of the promoterless reporter gene, include a plant that expressed GUS only in developing seed coats, T218, and another plant that expressed GUS in all organs, T1275 (see co-pending patent applications U.S. Ser. No. 08/593,121 and PCT/CA97/00064, both of which are incorporated by reference).

Cloning and deletion analysis of the GUS fusions in both of these plants revealed that the regulatory regions were located in the plant DNA proximal to the GUS gene:

In T218, a cryptic regulatory region was identified between an EcoRI-SmaI fragment, and further deletion analyses localized a cryptic regulatory element to an approximately 0.5 kb region between a XbaI and a SnaBI restriction endonuclease site of the 5' flanking tobacco DNA (see FIG. 2). This region spans from nucleotide 1 to nucleotide 467 of SEQ ID NO:1.

In T1275, a regulatory region was identified within an XbaI-SmaI fragment, which comprises several cryptic regulatory elements which were localized to several regions throughout the upstream region and include a minimal promoter region between DraI and NdeI sites (see FIG. 13), negative regulatory elements between XbaI and BstYI, a transcriptional enhancer between BstYI and DraI, and between DraI-(62) (nucleotides 1875 to 1992 of SEQ ID NO:2), and a translational enhancer regulatory element between the NdeI-SmaI sites (also referred to as "N", see below; SEQ ID NO:3). Also included are regulatory elements "ΔN" (also referred to as dN, or deltaN), an element derived from N, that comprises a Kozack sequence (FIG. 18, SEQ ID NO:4), and $N^M$, that lacks a Kozack sequence (SEQ ID NO:5).

However, it is to be understood that other portions of the isolated disclosed regulatory elements within T218 and T1275 may also exhibit activities in directing organ specificity, tissue specificity, or a combination thereof, or temporal activity, or developmental activity, or a combination thereof, or other regulatory attributes including, negative regulatory elements, enhancer sequences, or post transcriptional regulatory elements, including sequences that affect stability of the transcription or initiation complexes or stability of the transcript.

Thus, the present invention includes cryptic regulatory elements obtained from plants that are capable of conferring, or enhancing expression upon gene of interest linked in operative association therewith. Furthermore, the present invention includes cryptic regulatory elements obtained from plants capable of mediating the translational efficiency of a transcript produced from a gene of interest linked in operative association therewith. It is to be understood that the cryptic regulatory elements of the present invention may also be used in combination with other regulatory elements, either cryptic or otherwise, such as promoters, enhancers, or fragments thereof, and the like.

The term cryptic regulatory element refers to regulatory elements that are inactive in the control of expression at their native location. These inactive regulatory sequences are buried in the genome including intergenic regions or regions of genes that are not involved in the regulation of adjacent sequences but are capable of being functional when positioned adjacent to a gene.

By "regulatory element" or "regulatory region", it is meant a portion of nucleic acid typically, but not always, upstream of a gene, and may be comprised of either DNA or RNA, or both DNA and RNA. The regulatory elements of the present invention includes those which are capable of mediating organ specificity, or controlling developmental or temporal gene activation. Furthermore, "regulatory element" includes promoter elements, core promoter elements, elements that are inducible in response to an external stimulus, elements that are activated constitutively, or elements that decrease or increase promoter activity such as negative regulatory elements or transcriptional enhancers, respectively. It is also to be understood that enhancer elements may be repeated thereby further increasing the enhancing effect of an enhancer element on a regulatory region. "Regulatory elements" as used herein, also includes elements that are active following transcription initiation or transcription, for example, regulatory elements that modulate gene expression such as translational and transcriptional enhancers, translational and transcriptional repressors, and mRNA stability or instability determinants. In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as listed above) that modify gene expression. It is to be understood that nucleotide sequences, located within introns, or 3' of the coding region sequence may also contribute to the regulation of expression of a coding region of interest. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or fragments thereof, of the present invention may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or both enhancing or repressing transcriptional activity of the heterologous regulatory element and modulating post-transcriptional events. For example, one or more regulatory elements, or fragments thereof, of the present invention may be operatively associated with constitutive, inducible, or tissue specific promoters or fragment thereof, to modulate the activity of such promoters within plant, insect, fungi, bacterial, yeast, or animal cells.

An example of a cryptic regulatory element of the present invention, which is not to be considered limiting in any manner, is an organ-specific, and temporally-specific element obtained from plant T218. Such an element is a seed-specific regulatory element. More preferably, the element is a seed-coat specific regulatory element as described herein, or an analogue thereof, or a nucleic acid fragment localized between EcoRI-SmaI sites, as defined in restriction map of FIG. 2(B) or a fragment thereof. The seed coat-specific regulatory element may also be defined by a nucleic acid comprising substantial homology (similarity) with the nucleotide sequence comprising nucleotides 1-467, or 1-993, of SEQ ID NO:1. For example, which is not to be considered limiting in any manner, the nucleic acid may exhibit 80% similarity to the nucleotide sequence comprising nucleotides 1-467, or 1-993, of SEQ ID NO:1. Furthermore, the seed-coat specific nucleotide sequence may be defined as comprising at least a 19 bp fragment of nucleotides 1-467, or 1-993 as defined within SEQ ID NO:1.

Another example of a cryptic regulatory element of an aspect of the present invention includes, but is not limited to, a constitutive regulatory element obtained from the plant T1275, as described herein and analogues or fragments thereof, or a nucleic acid fragment localized between XbaI-SmaI, as identified by the restriction map of FIG. 12(B) or a fragment thereof. Furthermore, the constitutive regulatory element may be defined as a nucleic acid fragment localized between XbaI-SmaI as identified by the restriction map of FIG. 13(A) or (C) or a fragment thereof. The constitutive cryptic regulatory element may also be defined by a nucleotide sequence comprising at least an 18 bp fragment of the regulatory region defined in SEQ ID NO:2, or by a nucleic acid comprising from about 80% similarity to the nucleotide sequence of SEQ ID NO:2.

A further regulatory element of the present invention includes an enhancer element within the −394 to −62 fragment of T1275 (nucleotides 1660 to 1992 of SEQ ID NO:2). This fragment may also be duplicated and fused to a regulatory region, for example a core promoter, producing an increase in the activity of the regulatory region (see FIG. 13(D)).

Another cryptic regulatory element of the present invention includes, but is not limited to, a post-transcriptional or translational enhancer regulatory element localized between NdeI-SmaI (see FIG. 15, nucleotides 1-188 of SEQ ID NO:3). The post-transcriptional or translational enhancer regulatory element may also comprise the nucleotide sequence as defined by nucleotides 1-141 of SEQ ID NO:3 (nucleotides 2084-2224 of SEQ ID NO:2) or an analog thereof, or the element may comprise 80% similarity to the nucleotide sequence of nucleotides 1-141 of SEQ ID NO:3 (nucleotides 2086-2224 of SEQ ID NO:2).

A shortened fragment of the NdeI-SmaI fragment, referred to as ΔN, dN or deltaN is also characterized within the present invention. ΔN was prepared by mutagenesis replacing the out of frame ATG (located at nucleotides 2087-2089, SEQ ID NO:1) within the NdeI-SmaI fragment (see FIG. 18). ΔN constructs with (SEQ ID NO:4) or without (SEQ ID NO:5) a Kozak consensus sequence was also characterized (Tables 10, and 12) and found to exhibit enhancer activity. Therefore, other cryptic regulatory elements of the present invention include, but are not limited to, post-transcriptional or translational enhancers regulatory elements localized at nucleotides 1-97 of SEQ ID NO:4 and nucleotides 1-86 of SEQ DI NO: 4 or 5. These post-transcriptional or translational enhancer regulatory elements may comprise the nucleotide sequence as defined by nucleotides 1-86 of SEQ ID NO:4 or 5 (nucleotides 2170-2224 of SEQ ID NO:2) or an analog thereof, or the element may comprise 80% similarity to the nucleotide sequence of nucleotides 1-86 of SEQ ID NO:4 or 5 (nucleotides 2170-2224 of SEQ ID NO:2). Furthermore, these regulatory elements may comprise the nucleotide sequence as defined by nucleotides 1-97 of SEQ ID NO:4 and comprising a Kozack sequence or an analog thereof, or the element may comprise 80% similarity to the nucleotide sequence of nucleotides 1-97 of SEQ ID NO:4.

Figure 13A:
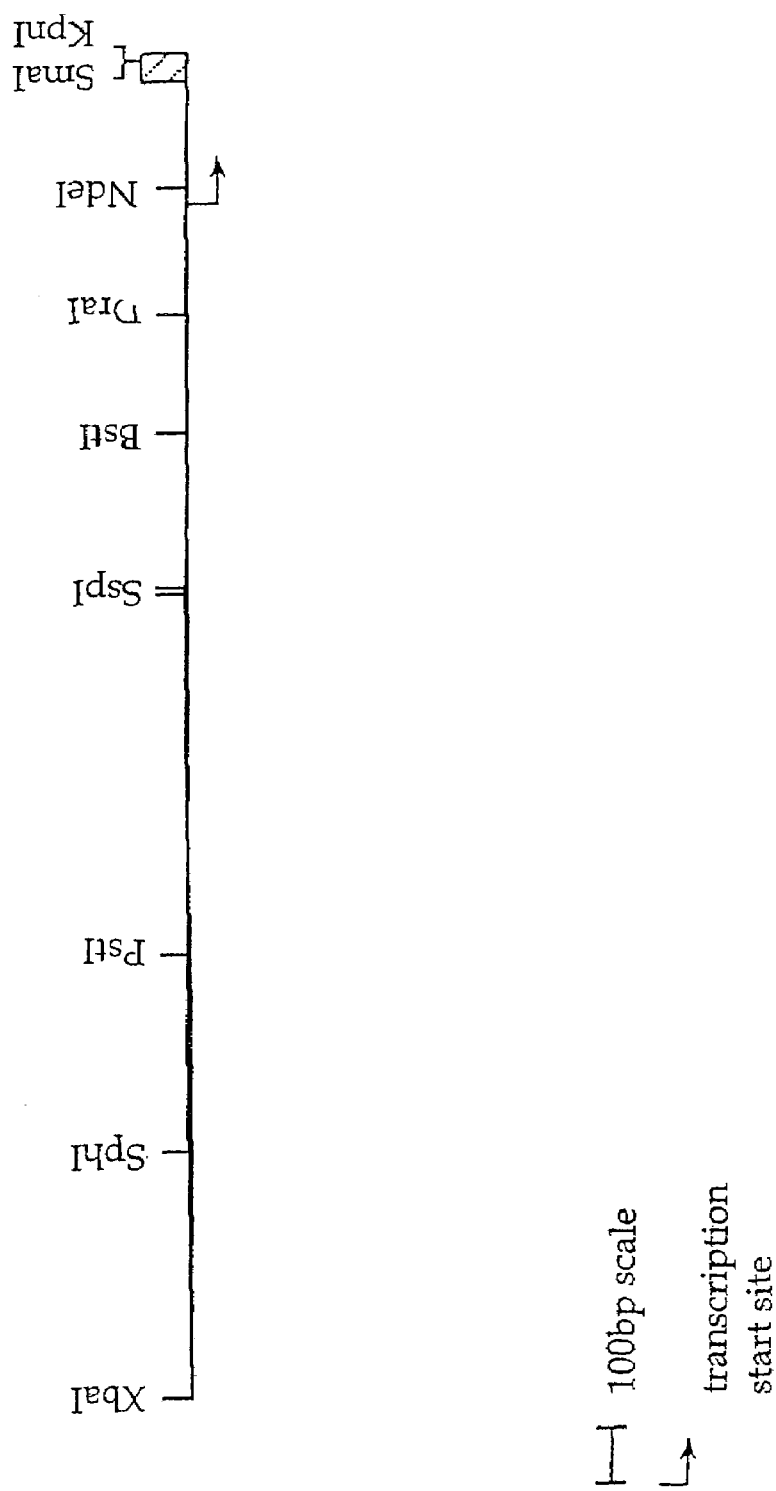
Figure 13B:
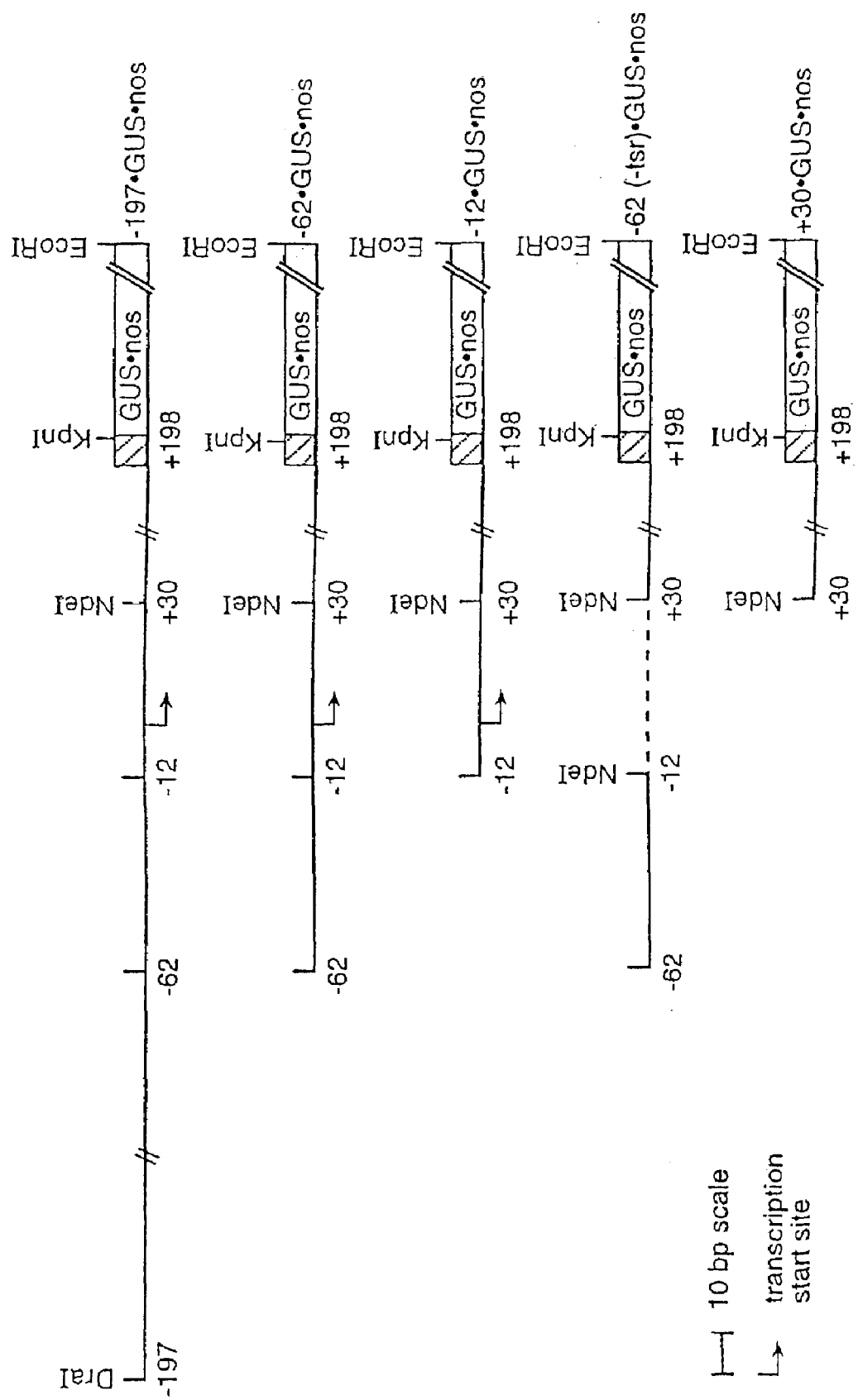
Figure 13C:
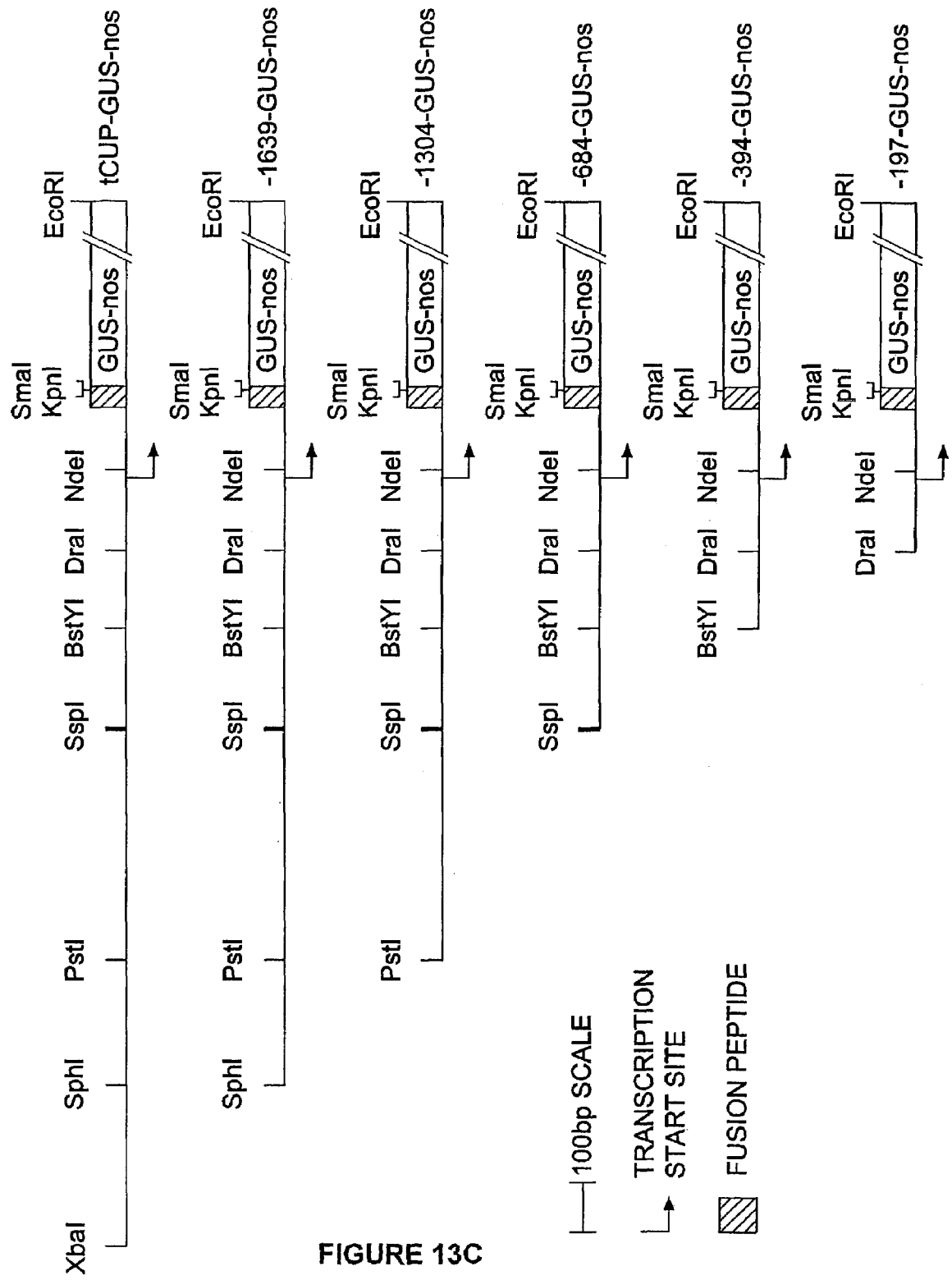
Figure 13E:
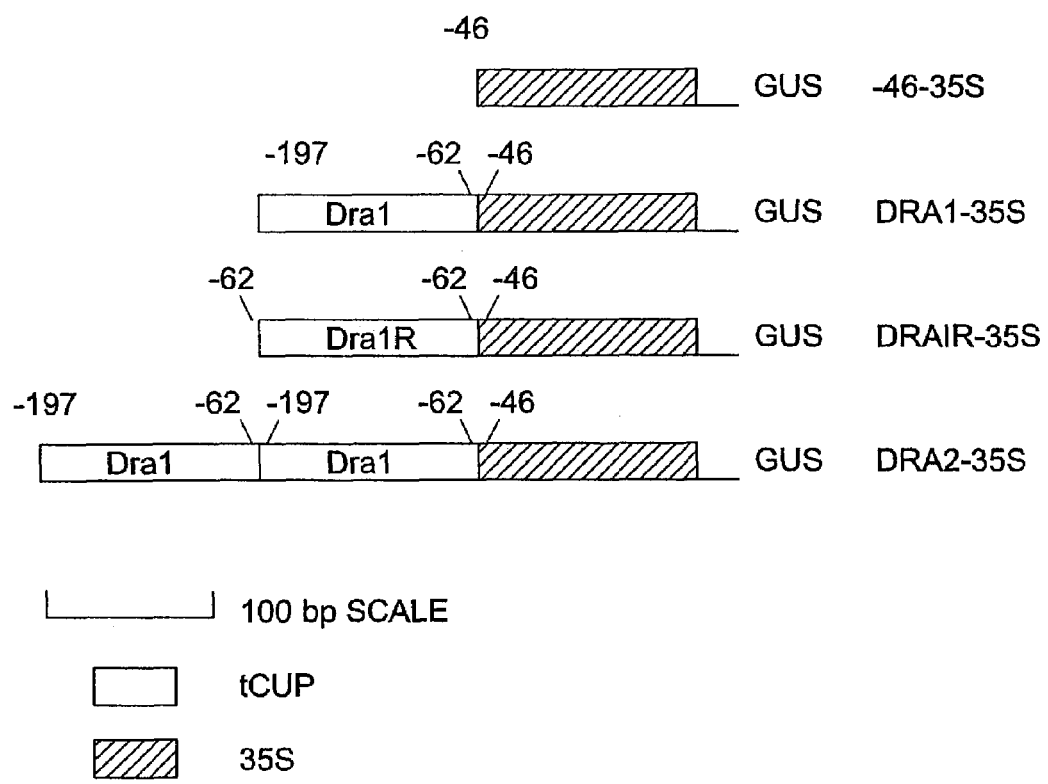
Figure 13F:
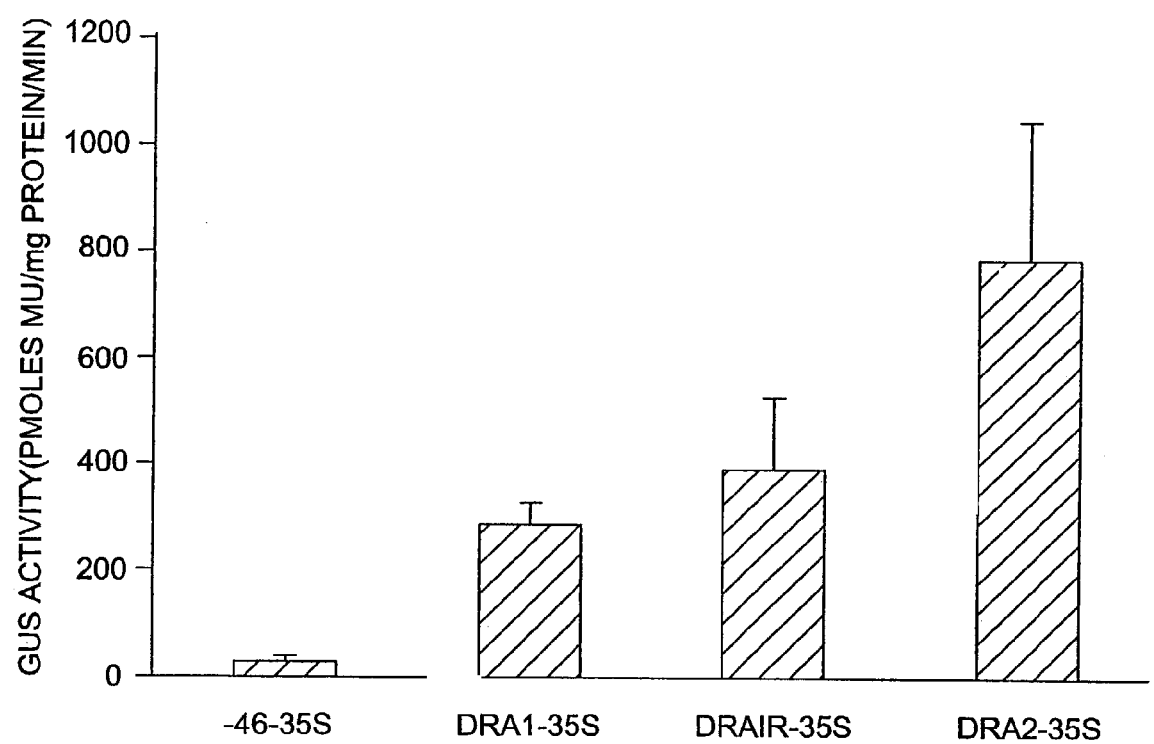

Furthermore, other regulatory elements of the present invention include negative regulatory elements (for example located within an XbaI-BstYI fragment as defined by FIG. 13(C); nucleotides 1-1660 of SEQ ID NO:2), a transcriptional enhancer localized within the BstYI-DraI fragment of FIG. 13(C) (nucleotides 1660-1875 of SEQ ID NO:2), a core promoter element located within the DraI-NdeI fragment of FIG. 13(C) (nucleotides 1875-2084 of SEQ ID NO:2), a transcriptional enhancer within the Dra1 to −62 fragment (nucleotides 1875-1992 of SEQ ID NO:2; FIGS. 13(D) to (G)), or a regulatory element or post-transcriptional element downstream of the transcriptional start site, for example but not limited to the NdeI-SmaI fragment (nucleotides 1-188 of SEQ ID NO3) and derivatives and fragments thereof (for example nucleotides 1-141 of SEQ ID NO:3), including N (nucleotides 1-129 or 1-97 of SEQ ID NO:4, $N^M$ (nucleotides 1-119 or 1-86 SEQ ID NO:5), and nucleotides 1-86 of SEQ ID NO:4 or 5 (nucleotides 2084 to 2170 of SEQ ID NO:2).

An "analogue" of the above identified cryptic regulatory elements includes any substitution, deletion, or additions to the sequence of a regulatory element provided that said analogue maintains at least one regulatory property associated with the activity of the regulatory element. Such properties include directing organ specificity, tissue specificity, or a combination thereof, or temporal activity, or developmental activity, or a combination thereof, or other regulatory attributes including, negative regulatory elements, enhancer sequences, or sequences that affect stability of the transcription or translation complexes or stability of the transcript.

There are several types of regulatory elements, including those that are developmentally regulated, inducible and constitutive. A regulatory element that is developmentally regulated, or controls the differential expression of a gene under its control, is activated within certain organs or tissues of an organ at specific times during the development of that organ or tissue. However, some regulatory elements that are developmentally regulated may preferentially be active within certain organs or tissues at specific developmental stages, they may also be active in a developmentally regulated manner, or at a basal level in other organs or tissues within the plant as well.

An inducible regulatory element is one that is capable of directly or indirectly activating transcription of one or more DNA sequences or genes in response to an inducer. In the absence of an inducer the DNA sequences or genes will not be transcribed. Typically the protein factor, that binds specifically to an inducible regulatory element to activate transcription, is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

A constitutive regulatory element directs the expression of a gene throughout the various parts of a plant and continuously throughout plant development. Examples of known constitutive regulatory elements include promoters associated with the CaMV 35S transcript. (Odell et al., 1985, Nature, 313: 810-812), the rice actin 1 (Zhang et al, 1991, Plant Cell, 3: 1155-1165) and triosephosphate isomerase 1 (Xu et al, 1994, Plant Physiol. 106: 459-467) genes, the maize ubiquitin 1 gene (Cornejo et al, 1993, Plant Mol. Biol. 29: 637-646),the Arabidopsis ubiquitin 1 and 6 genes (Holtorf et al, 1995, Plant Mol. Biol. 29: 637-646), and the tobacco translational initiation factor 4A gene (Mandel et al, 1995 Plant Mol. Biol. 29: 995-1004).

The term "constitutive" as used herein does not necessarily indicate that a gene under control of the constitutive regulatory element is expressed at the same level in all cell types, but that the gene is expressed in a wide range of cell types even though variation in abundance is often observed.

The present invention is further directed to a chimeric gene construct containing a DNA of interest operatively linked to a regulatory element of the present invention. Any exogenous gene can be used and manipulated according to the present invention to result in the expression of said exogenous gene.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3• end of the mRNA precursor. Polyadenylation signals are commonly recognized by the presence of homology to the canonical form 5'AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1, 5-bisphosphate carboxylase (ssRUBISCO) gene. The 3' untranslated region from the structural gene of the present construct can therefore be used to construct chimeric genes for expression in plants.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

Also considered part of this invention are transgenic plants containing the chimeric gene construct comprising a regulatory element of the present invention. However, it is to be understood that the regulatory elements of the present invention may also be combined with gene of interest for expression within a range of host organisms. Such organisms include, but are not limited to:

plants, both monocots and dicots, for example, corn, wheat, barley, oat, tobacco, Brassica, soybean, pea, alfalfa, potato, ginseng, Arabidopsis;

trees, for example peach, spruce;

yeast, fungi, insects, animal and bacteria cells.

Methods for the transformation and regeneration of these organisms are established in the art and known to one of skill in the art.

By "gene of interest" it is meant any gene that is to be expressed within a host organism. Such a gene of interest may include, but is not limited to, a gene that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-α, interferon-β, interferon-γ, blood clotting factors, for example, Factor VIII, Factor IX, or tPA or combinations thereof. A gene of interest may also encode an industrial enzyme, protein supplement, nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis etc.

Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebrve, D B Layzell (eds), Addison Wesly, Langmans Ltd. London, pp. 561-579 (1997). The present invention further includes a suitable vector comprising the chimeric gene construct.

The DNA sequences of the present invention thus include the DNA sequences of SEQ ID NO: 1, 2, 3, 4 and 5, the regulatory regions and fragments thereof, as well as analogues of, or nucleic acid sequences comprising about 80% similarity with the nucleic acids as defined in SEQ ID NO's: 1 to 5. Analogues (as defined above), include those DNA sequences which hybridize under stringent hybridization conditions (see Maniatis et al., in Molecular Cloning (A Laboratory Manual), Cold Spring Harbor Laboratory, 1982, p. 387-389) to any one of the DNA sequence of SEQ ID NO: 1, 2, 3, 4, or 5, provided that said sequences maintain at least one regulatory property of the activity of the regulatory element as defined herein.

An example of one such stringent hybridization conditions may be hybridization in 4×SSC at 65° C., followed by washing in 0.1×SSC at 65° C. for an hour. Alternatively an exemplary stringent hybridization condition could be in 50% formamide, 4×SSC at 42° C. Analogues also include those DNA sequences which hybridize to any one of the sequences of SEQ ID NO:1 to 5 under relaxed hybridization conditions, provided that said sequences maintain at least one regulatory property of the activity of the regulatory element.

Examples of such non-hybridization conditions includes hybridization in 4×SSC at 50° C. or with 30-40% formamide at 42° C.

There are several lines of evidence that suggest that the seed coat-specific expression of GUS activity in the plant T218 is regulated by a cryptic regulatory element. The region surrounding the regulatory element and transcriptional start site for the GUS gene are not transcribed in untransformed plants. Transcription was only observed in plant T218 when T-DNA was inserted in cis. DNA sequence analysis did not uncover a long open reading frame within the 3.3 kb region cloned. Moreover, the region is very AT rich and predicted to be noncoding (data not shown) by the Fickett algorithm (Fickett, 1982, *Nucleic Acids Res.* 10, 5303-5318) as implemented in DNASIS 7.0 (Hitachi). Southern blots revealed that the insertion site is within the *N. tomentosiformis* genome and is not conserved among related species as would be expected for a region with an important gene.

Furthermore, Northern analysis demonstrate that the transcript, associated with the regulatory region and corresponding to the native plant sequence, does not accumulate in developing seeds or leaves of untransformed plants. This indicates that in native plants, the regulatory region as defined as pT218, is silent.

Similarly, results indicate that the constitutive expression of GUS activity in the plant T1275 is regulated by a cryptic regulatory element. RNase protection assays performed on the region spanning the regulatory element and downstream region did not reveal a transcript for the sense strand (see FIG. 16, Table 2). RNase protection assays were performed using RNA from organs of untransformed tobacco and probes that spanned the T1275 sequence from about −2055 bp to +1200 bp relative to the transcriptional start site. In all tissues tested (leaf, stem, root, flower bud, petal, ovary and developing seed) protected fragments were not detected, in the sense orientation relative to the GUS coding region, with all probes (FIG. 16; see also PCT CA97/00064, which is incorporated by reference). Furthermore, GenBank searches revealed no significant sequence similarity with the T1275 sequence. An amino acid identity of about 66% with two open reading frames on the antisense strand of the genomic sequence of T1275 (between about −1418 and −1308, nucleotides 636-746 of SEQ ID NO:2; and between about −541 and −395, nucleotides 1513-1659 of SEQ ID NO:2 relative to the transcriptional start) and an open reading frame of a partial *Arabidopsis* expressed sequence (GenBank Accession No. W43439) was identified. The sequence which lies downstream of sequences at the T-DNA insertion point in untransformed tobacco shows no significant similarity in GenBank searches. These data suggest that this region is silent in untransformed plants and that the insertion of the T-DNA activated a cryptic promoter.

Southern analysis indicates that the 2.2 kb regulatory region of T1275 does not hybridize with DNA isolated from soybean, potato, sunflower, *Arabidopsis, B. napus, B. oleracea*, corn, wheat or black spruce. However, transient assays indicate that this regulatory region can direct expression of the GUS coding region in all plant species tested including canola, tobacco, *Brassica, Arabidopsis*, soybean, alfalfa, pea, ginseng, potato, corn, wheat, barley, white spruce and peach (Table 3), indicating that this regulatory element is useful for directing gene expression in both dicot and monocot plants as well as trees. Furthermore, regulatory elements were also found to modulate gene expression in a diverse range of species including yeast, bacteria and insect cells.

The transcriptional start site was delimited by RNase protection assay to a single position about 220 bp upstream of the translational initiation codon of the GUS coding region in the T-DNA. The sequence around the transcriptional start site exhibits similarity with sequences favored at the transcriptional start site compiled from available dicot plant genes (T/A T/C $A_{+1}$ A C/A C/A A/C/T A A A/T). Sequence similarity is not detected about 30 bp upstream of the transcriptional start site with the TATA-box consensus compiled from available dicot plant genes (C T A T A A/T A T/A A).

Deletions in the upstream region indicate that negative regulatory elements and enhancer sequences exist within the full length regulatory region. For example, deletion of the 5' region to BstYI (−394 relative to the transcriptional start site; see FIG. 13(C)) resulted in a 3 to 8 fold increase in expression of the gene associated therewith (see Table 6), indicating the occurrence of at least one negative regulatory element within the XbaI-BstYI portion of the full length regulatory element. Other negative regulatory elements also exist within the XbaI-BstYI fragment as removal of an XbaI-PstI fragment also resulted in increased activity (−1403-GUS-nos; Table 6). An enhancer is also localized within the BstYI-DraI fragment as removal of this region results in a 4 fold loss in activity of the remaining regulatory region (−197-GUS-nos; Table 6).

5' deletions of the promoter (see FIGS. 13(B) and (C) and analysis by transient expression using biolistics showed that the promoter was active within a fragment 62 bp from the transcriptional start site indicating that the core promoter has a basal level of expression (see Table 5). Deletion of a fragment containing the transcriptional start site (see −62(-tsr)/GUS/nos in FIG. 13(C); Table 5) did not eliminate expression, however deletions to −12 bp and further (i.e. +30) did eliminate expression indicating that the region defined by −(62-12) bp (nucleotides 1992-2042 of SEQ ID NO:2) contained the core promoter. DNA sequence searches did not reveal conventional core promoter motifs found in plant genes such as the TATA box.

A number of the 5' promoter deletion clones (FIGS. 13(B) and (C)) were transferred into tobacco and *Arabidopsis* by *Agrobacterium*-mediated transformation using the vector pRD400. Analysis of GUS specific activity in leaves of transgenic plants (see Table 6) confirmed the transient expression data down to the −197 fragment (nucleotides 1875-2224 of SEQ ID NO:2). Histochemical analysis of tobacco organs sampled from the transgenic plants indicated GUS expression in leaf, seeds and flowers. Histochemical analysis of *Arabidopsis* organs revealed GUS activity in leaf, stem flowers and silques when the promoter was deleted to the −394 and −197 fragments (see FIGS. 13 (E) to (G)).

A comparison of GUS specific activities in the leaves of transgenic tobacco SRI transformed with the T1275-GUS-nos gene and the 35S-GUS-nos genes revealed a similar range of values (FIG. 14(A)). Furthermore, the GUS protein levels detected by Western blotting were similar between plants transformed with either gene when the GUS specific activities were similar (FIG. 14(C)). Analysis of GUS mRNA levels by RNase protection however revealed that the levels of mRNA were about 60 fold (mean of 13 measurements) lower in plants transformed with the T1275-GUS-nos gene (FIG. 14(B)) suggesting the existence of a post-transcriptional regulatory element in the mRNA leader sequence.

Expression of GUS, under the control of T1275 or a fragment thereof, or the modulation of GUS expression arising from T 1275 or a fragment thereof, has been observed in a range of species including corn, wheat, barley, oat, tobacco, *Brassica*, soybean, alfalfa, pea, potato, Ginseng, *Arabidopsis*, peach, spruce, yeast, fungi, insects and bacterial cells.

Further analysis confirmed the presence of a regulatory sequence within the NdeI-SmaI fragment of the mRNA leader sequence that had a significant impact on the level of GUS specific activity expressed in all organs tested. Deletion of the NdeI-SmaI fragment from the T1275-GUS-nos gene (FIG. 15) resulted in about a 46-fold reduction in the amount of GUS specific activity that could be detected in leaves of transgenic tobacco cv Delgold (see Table 7). Similar results were also observed in the transgenic tobacco cultivar SRI and transgenic alfalfa (Table 7). Addition of the same fragment to a 35S-GUS-nos gene construct (FIG. 15) increased the amount of GUS specific activity by about 5-fold in transgenic tobacco and a higher amount in transgenic alfalfa (see Table 7). Increased GUS activity was observed in organs of tobacco and alfalfa plants tranformed with constructs containing NdeI-SmaI fragment (Table 8 and 9).

A modulation of GUS activity was noted in a variey of species that were transformed with a regulatory element of the present invention. For example but not necessarily limited to, the NdeI-SmaI fragment of T1275 (also referred to as "N") and derivatives or analogues thereof, produced an increase in activity within a variety of organisms tested including a range of plants (Tables 3 and 10, and FIG. 19), white spruce (a conifer; Table 11) and yeast (Table 12).

A shortened fragment of the NdeI-SmaI fragment, (referred to as "ΔN", "dN", or "deltaN") was produced that lacks the out-of-frame upstream ATG at nucleotides 2087-2089 of SEQ ID NO:2 (see FIGS. 18(A) and (B)). Constructs comprising T1275(N)-GUS-nos yielded 5 fold greater levels of GUS activity in leaves of transgenic tobacco compared to plants expressing T1275-GUS-nos. Furthermore, in corn callus and yeast, ΔN significantly increased GUS expression driven by the 35 S promoter (FIG. 19 and Table 10)

The NdeI-SmaI regulatory elements situated downstream of the transcriptional start site functions both at a transcriptional, and post-transcriptional level. The levels of mRNA observed in transgenic plants transformed with T1275-GUS-nos are higher than the levels in plants transformed with T1275(−N)-GUS-nos. However, the opposite is true with plants tranformed with 35S-GUS-nos or 35S(+N)-GUS-nos, where higher levels of mRNA are detected in the absence of the NdeI-SmaI fragment (see FIGS. 17(A) and (B)). This indicates that this region functions by either modulating transcriptional rates, or the stability of the transcript, or both.

The NdeI-SmaI region also functions post-transcriptionally. The ratio of GUS specific activity to relative RNA level in individual transgenic tobacco plants that lack the NdeI-SmaI fragment is lower, and when averaged indicates an eight fold reduction in GUS activity per RNA, than in plants comprising this region (FIG. 17(C)). Similarly, an increase, by an average of six fold, in GUS specific activity is observed when the NdeI-SmaI region is added within the 35S untranslated region (FIG. 17(C)). The GUS specific activity:relative RNA levels are similar in constructs containing the NdeI-SmaI fragment (T1275-GUS-nos and 35S+N-GUS-nos). These results indicate that the NdeI-SmaI fragment modulates gene expression post-transcriptionally. Further experiments suggest that this region is a novel translational enhancer. Translation of transcripts in vitro demonstrate an increase in translational efficiency of RNA containing the NdeI to SmaI fragment (see Table 13). Furthermore, the levels of protein produced using mRNAs comprising the NdeI-SmaI fragment are greater than those produced using the known translational enhancer of Alfalfa Mosaic Virus RNA4. These results indicate that this region functions post-transcriptionally, as a translational enhancer.

As this is the first report of cryptic regulatory elements in plants, it is impossible to estimate the degree to which cryptic regulatory elements may contribute to the high frequencies of promoterless marker gene activation in plants. It is interesting to note that transcriptional GUS fusions in *Arabidopsis* occur at much greater frequencies (54%) than translational fusions (1.6%, Kertbundit et al., 1991, *Proc. Natl. Acad Sci.* USA 88, 5212-5216). The possibility that cryptic promoters may account for some fusions was recognized by Lindsey et al. (1993, *Transgenic Res.* 2, 33-47).

The regulatory elements of the present invention may be used to control the expression of a gene of interest within desired host expression system, for example, but not limited to:
  plants, both monocots and dicots, for example, corn, tobacco, *Brassica*, soybean, pea, alfalfa, potato, ginseng, wheat, oat, barley, *Arabidopsis*;
  trees, for example peach, spruce;
  yeast, fungi, insects, and bacteria.

Furthermore, the regulatory elements as described herein may be used in conjunction with other regulatory elements, such as tissue specific, inducible or constitutive promoters, enhancers, or fragments thereof, and the like. For example, the regulatory region or a fragment thereof as defined herein may be used to regulate gene expression of a gene of interest spatially and developmentally within developing seed coats, or within a heterologous expression system, for example yeast, insects, or fungi expression systems. Some examples of such uses, which are not to be considered limiting, include:
  1. Modification of storage reserves in seed coats, such as starch by the expression of yeast invertase to mobilize the starch or expression of the antisense transcript of ADP-glucose pyrophosphorylase to inhibit starch biosynthesis.
  2. Modification of seed color contributed by condensed tannins in the seed coats by expression of antisense transcripts of the phenylalanine ammonia lyase or chalcone synthase genes.
  3. Modification of fibre content in seed-derived meal by expression of antisense transcripts of the caffeic acid-o-methyl transferase or cinnamoyl alcohol dehydrogenase genes.
  4. Inhibition of seed coat maturation by expression of ribonuclease genes to allow for increased seed size, and to reduce the relative biomass of seed coats, and to aid in dehulling of seeds.
  5. Expression of genes in seed coats coding for insecticidal proteins such as -amylase inhibitor or protease inhibitor.
  6. Partitioning of seed metabolites such as glucosinolates into seed coats for nematode resistance.
  7. Nucleotide fragments of the regulatory region of at least 19 bp as a probe in order to identify analogous regions within other plants.
  8. Enhancing expression of a gene of interest within a host organisms of interest. Regulatory regions or fragments thereof, including enhancer fragments of the present invention, may be operatively associated with a heterologous nucleotide sequence including heterologous regulatory regions to increase the expression of a gene of interest within a host organism. A gene of interest may include, but is not limited to, a gene that encodes a pharmaceutically active protein, for example growth factors, growth regulators, antibodies, antigens, their derivatives useful for immunization or vaccination and the like. Such proteins include, but are not limited to, interleukins, insulin, G-CSF, GM-CSF, hPG-CSF, M-CSF or combinations thereof, interferons, for example, interferon-α, interferon-β, interferon-γ, blood clotting factors, for example, Factor VIII, Factor IX, or tPA or combinations thereof. A gene of interest may also encode an industrial enzyme, protein supplement, nutraceutical, or a value-added product for feed, food, or both feed and food use. Examples of such proteins include, but are not limited to proteases, oxidases, phytases chitinases, invertases, lipases, cellulases, xylanases, enzymes involved in oil metabolic and biosynthetic pathways etc.

Similarly, a constitutive regulatory element may also be used to drive the expression within all organs or tissues, or both of a plant of a gene of interest, and such uses are well established in the literature. For example, fragments of specific elements within the 35S CaMV promoter have been duplicated or combined with other promoter fragments to produce chimeric promoters with desired properties (e.g. U.S. Pat. Nos. 5,491,288, 5,424,200, 5,322,938, 5,196,525, 5,164,316). As indicated above, a constitutive regulatory element or a fragment thereof, as defined herein, may also be used along with other promoter, enhancer elements, or fragments thereof, translational enhancer elements or fragments thereof in order to control gene expression. Furthermore, oligonucleotides of 18 bps or longer are useful as probes or PCR primers in identifying or amplifying related DNA or RNA sequences in other tissues or organisms.

Thus this invention is directed to regulatory elements and gene combinations comprising these cryptic regulatory elements. Further this invention is directed to such regulatory elements and gene combinations in a cloning vector, wherein the gene is under the control of the regulatory element and is capable of being expressed in a plant cell transformed with the vector. This invention further relates to transformed plant cells and transgenic plants regenerated from such plant cells. The regulatory element, and regulatory element-gene combination of the present invention can be used to transform any plant cell for the production of any transgenic plant. The present invention is not limited to any plant species, or species other than plant.

While this invention is described in detail with particular reference to preferred embodiments thereof, said embodiments are offered to illustrate but not limit the invention.

EXAMPLES

Transfer of binary constructs to *Agrobacterium* and leaf disc transformation of *Nicotiana tabacum* SRI were performed as described by Fobert et al. (1991, *Plant Mol. Biol.* 17, 837-851). Plant tissue was maintained on 100 µg/ml kanamycin sulfate (Sigma) throughout in vitro culture.

Nine-hundred and forty transgenic plants were produced. Several hundred independent transformants were screened for GUS activity in developing seeds using the fluorogenic assay. One of these, T218, was chosen for detailed study because of its unique pattern of GUS expression. Furthermore, following the screening of transformants in a range of plant organs, T 1275 was selected which exhibited high level, constitutive expression of GUS.

Characterization of a Seed Coat-Specific GUS Fusion—T218

Fluorogenic and histological GUS assays were performed according to Jefferson (*Plant Mol. Biol. Rep.*, 1987, 5, 387-405), as modified by Fobert et al. (*Plant Mol. Biol.*, 1991, 17, 837-851). For initial screening, leaves were harvested from in vitro grown plantlets. Later flowers corresponding to developmental stages 4 and 5 of Koltunow et al. (*Plant Cell*, 1990, 2, 1201-1224) and beige seeds, approximately 12-16 dpa (Chen et al., 1988, *EMBO J*. 7, 297-302), were collected from plants grown in the greenhouse. For detailed, quantitative analysis of GUS activity, leaf, stem and root tissues were collected from kanamycin resistant FI progeny of the different transgenic lines grown in vitro. Floral tissues were harvested at developmental stages 8-10 (Koltunow et al., 1990, *Plant Cell* 2, 1201-1224) from the original transgenic plants. Flowers of these plants were also tagged and developing seeds were collected from capsules at 10 and 20 dpa. In all cases, tissue was weighed, immediately frozen in liquid nitrogen, and stored at −80 C.

Tissues analyzed by histological assay were at the same developmental stages as those listed above. Different hand-cut sections were analyzed for each organ. For each plant, histological assays were performed on at least two different occasions to ensure reproducibility. Except for floral organs, all tissues were assayed in phosphate buffer according to Jefferson (1987, *Plant Mol. Biol. Rep*. 5, 387-405), with 1 mM X-Gluc (Sigma) as substrate. Flowers were assayed in the same buffer containing 20% (v/v) methanol (Kosugi et al., 1990, *Plant Sci*. 70, 133-140).

Figure 1:
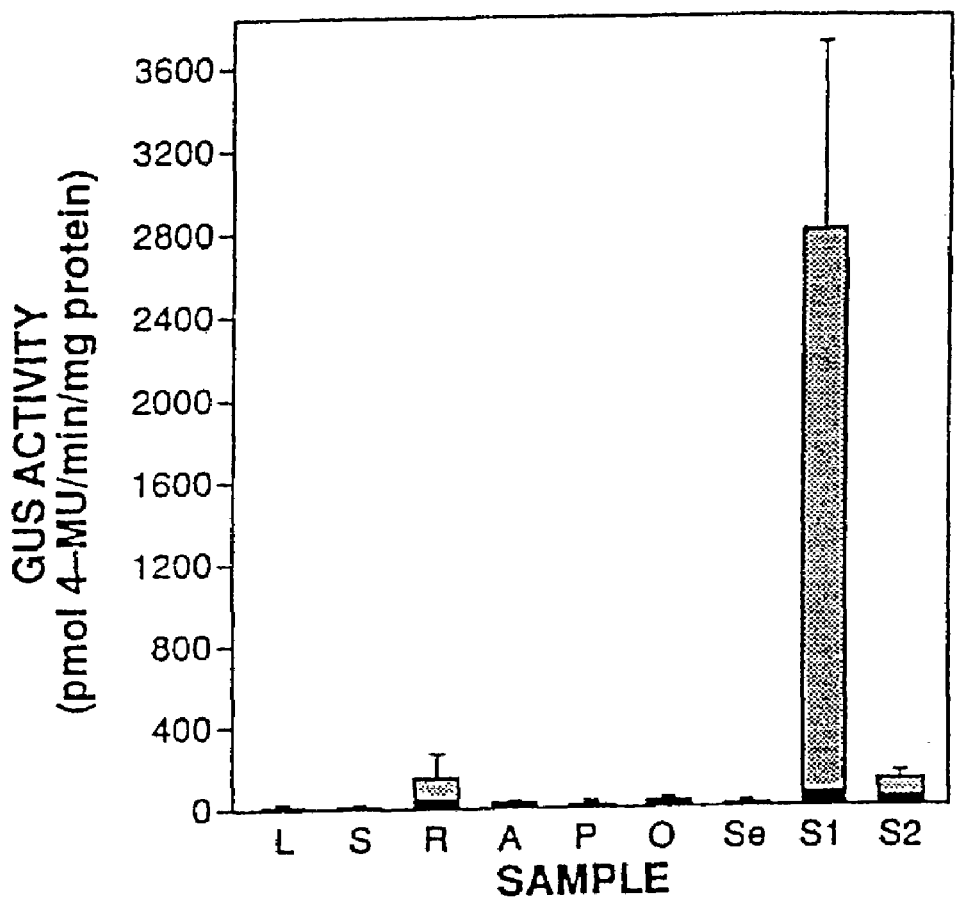
FIG. 1 depicts the fluorogenic analyses of GUS expression in the plant T218. Each bar represents the average±one standard deviation of three samples. Nine different tissues were analyzed: leaf (L), stem (S), root (R), anther (A), petal (P), ovary (O), sepal (Se), seeds 10 days post anthesis (S1) and seeds 20 days post-anthesis (S2). For all measurements of GUS activity, the fraction attributed to intrinsic fluorescence, as determined by analysis of untransformed tissues, is shaded black on the graph. Absence of a black area at the bottom of a histogram indicates that the relative contribution of the background fluorescence is too small to be apparent.

Tissue-specific patterns of GUS expression were only found in seeds. For instance, GUS activity in plant T218 (FIG. 1) was localized in seeds from 9 to 17 days postanthesis (dpa). GUS activity was not detected in seeds at other stages of development or in any other tissue analyzed which included leaf, stem, root, anther, ovary, petal and sepal (FIG. 1). Histological staining with X-Gluc revealed that GUS expression in seeds at 14 dpa was localized in seed coats but was absent from the embryo, endosperm, vegetative organs and floral organs (results not shown).

The seed coat-specificity of GUS expression was confirmed with the more sensitive fluorogenic assay of seeds derived from reciprocal crosses with untransformed plants. The seed coat differentiates from maternal tissues called the integuments which do not participate in double fertilization (Esau, 1977, *Anatomy of Seed Plants*. New York: John Wiley and Sons). If GUS activity is strictly regulated, it must originate from GUS fusions transmitted to seeds maternally and not by pollen. As shown in Table 1, this is indeed the case. As a control, GUS fusions expressed in embryo and endosperm, which are the products of double fertilization, should be transmitted through both gametes. This is illustrated in Table 1 for GUS expression driven by the napin promoter (BngNAPI, Baszczynki and Fallis, 1990, *Plant Mol. Biol*. 14, 633-635) which is active in both embryo and endosperm (data not shown).

TABLE 1

| GUS activity in seeds at 14 days post anthesis. | | |
|---|---|---|
| Cross | | GUS Activity |
| ♀ | ♂ | nmole MU/min/mg Protein |
| T218 | T218 | 1.09 ± 0.39 |
| T218 | WT[a] | 3.02 ± 0.19 |
| WT | T218 | 0.04 ± 0.005 |

TABLE 1-continued

| GUS activity in seeds at 14 days post anthesis. | | |
|---|---|---|
| Cross | | GUS Activity |
| ♀ | ♂ | nmole MU/min/mg Protein |
| WT | WT | 0.04 ± 0.005 |
| NAP-5[b] | NAP-5 | 14.6 ± 7.9 |
| NAP-5 | WT | 3.42 ± 1.60 |
| WT | NAP-5 | 2.91 ± 1.97 |

[a]WT, untransformed plants
[b]Transgenic tobacco plants with the GUS gene fused to the napin, Bng-NAP1, promoter (Baszczynski and Fallis, 1990, Plant Mol. Biol. 14, 633-635).

Cloning and Analysis of the Seed Coat-Specific GUS Fusion

Genomic DNA was isolated from freeze-dried leaves using the protocol of Sanders et al. (1987, *Nucleic Acid Res*. 15, 1543-1558). Ten micrograms of T218 DNA was digested for several hours with EcoRI using the appropriate manufacturer-supplied buffer supplemented with 2.5 mM spermidine. After electrophoresis through a 0.8% TAE agarose gel, the DNA size fraction around 4-6 kb was isolated, purified using the GeneClean kit (BIO 101 Inc., LaJolla, Calif.), ligated to phosphatase-treated EcoRI-digested Lambda GEM-2 arms (Promega) and packaged in vitro as suggested by the supplier. Approximately 125,000 plaques were transferred to nylon filters (Nytran, Schleicher and Schuell) and screened by plaque hybridization (Rutledge et al., 1991, *Mol. Gen. Genet*. 229, 31-40), using the 3' (termination signal) of the nos gene as probe (probe #1, FIG. 2). This sequence, contained in a 260 bp SstI/EcoRI restriction fragment from pPRF-101 (Fobert et al., 1991, *Plant Mol. Biol*. 17, 837-851), was labelled with [α-$^{32}$P]-dCTP (NEN) using random priming (Stratagene). After plaque purification, phage DNA was isolated (Sambrook et al., 1989, A Laboratory Manual. New York: Cold Spring Harbor Laboratory Press), mapped and subcloned into pGEM-4Z (Promega).

The GUS fusion in plant T218 was isolated as a 4.7 kb EcoRI fragment containing the 2.2 kb promoterless GUS-nos gene at the T-DNA border of pPRF120 and 2.5 kb of 5' flanking tobacco DNA (pT218, FIG. 2), using the nos 3' fragment as probe (probe #1, FIG. 2). To confirm the ability of the flanking DNA to activate the GUS coding region, the entire 4.7 kb fragment was inserted into the binary transformation vector pBIN19 (Bevan, 1984, *Nucl. Acid Res*. 12, 8711-8721), as shown in FIG. 2. Several transgenic plants were produced by *Agrobacterium*-mediated transformation of leaf discs. Plants were transformed with a derivative which contained the 5' end of the GUS gene distal to the left border repeat. This orientation is the same as that of the GUS gene in the binary vector pBI101 (Jefferson, 1987, *Plant Mol. Biol. Rep*. 5, 387-405). Southern blots indicated that each plant contained 1-4 T-DNA insertions at unique sites. The spatial patterns of GUS activity were identical to that of plant T218. Histologically, GUS staining was restricted to the seed coats of 14 dpa seeds and was absent in embryos and 20 dpa seeds (results not shown). Fluorogenic assays of GUS activity in developing seeds showed that expression was restricted to seeds between 10 and 17 dpa, reaching a maximum at 12 dpa (FIGS. 3(*a*) and 3(*b*)). The 4.7 kb fragment therefore contained all of the elements required for the tissue-specific and developmental regulation of GUS expression.

Figures 3A, 3B:
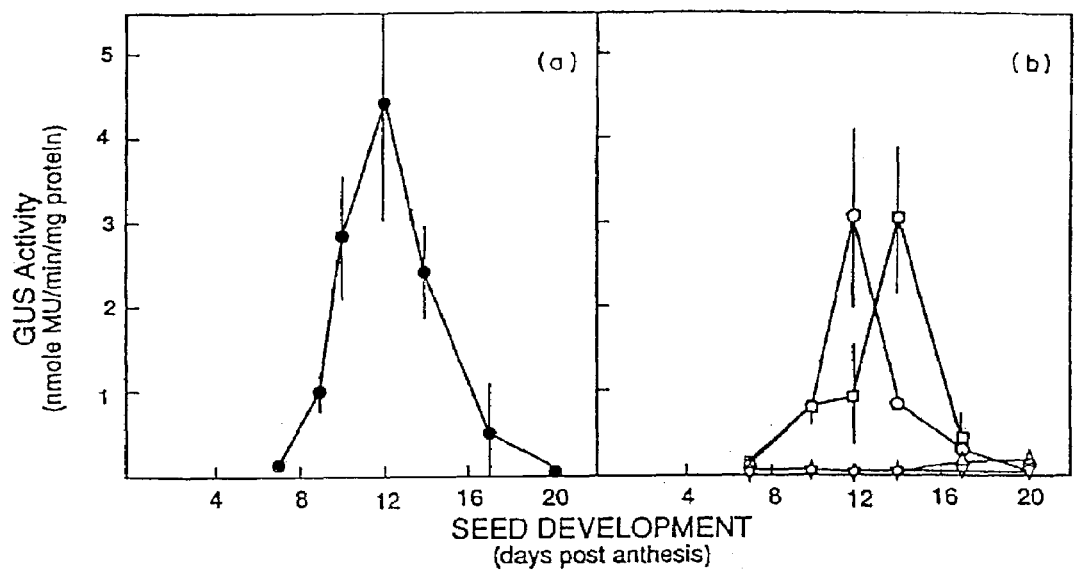
FIG. 3 shows the expression pattern of promoter fusions during seed development. GUS activity in developing seeds (4-20 days postanthesis (dpa)) of (FIG. 3a) plant T218 (●-●) and (FIG. 3b) plants transformed with vectors pT218-1 (○-○), pT218-2 (□-□), pT218-3 (∇-∇) and pT218-4 (Δ-Δ) which are illustrated in FIG. 2. The 2 day delay in the peak of GUS activity during seed development, seen with the pT218-2 transformant, likely reflects greenhouse variation conditions.
Figure 4:
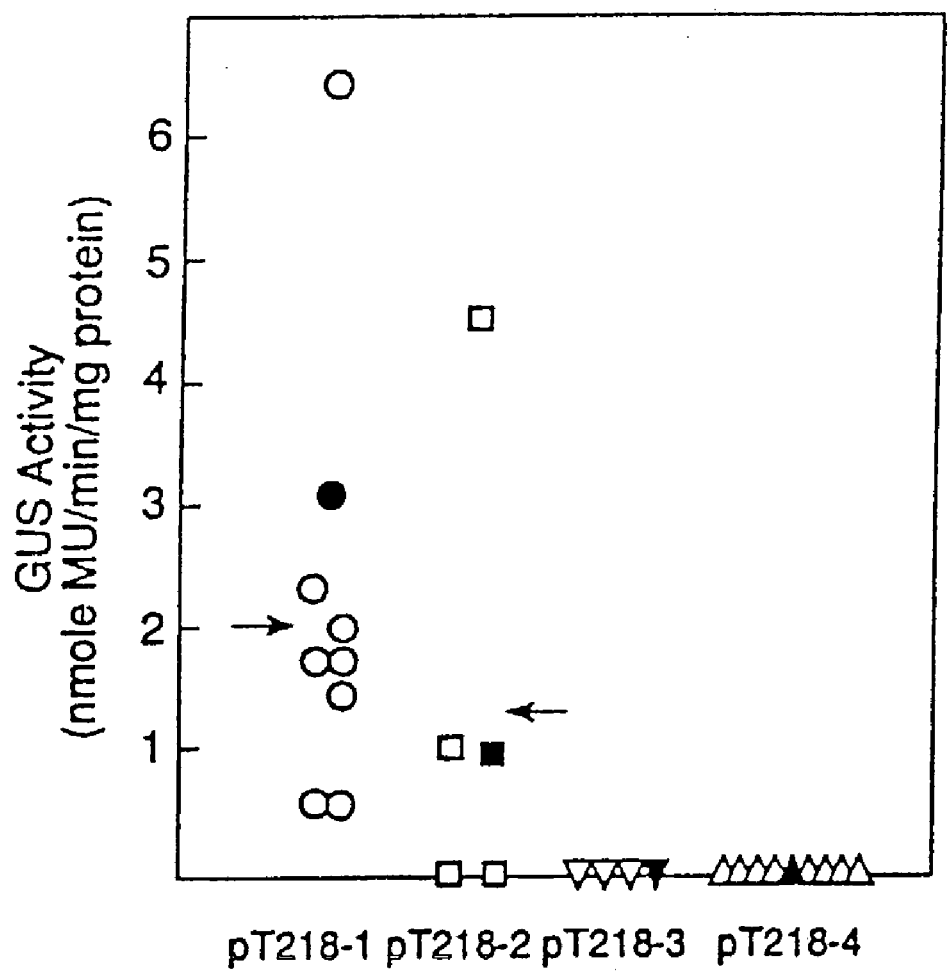
FIG. 4 shows GUS activity in 12 dpa seeds of independent transformants produced with vectors pT218-l (○), pT218-2 (□), pT218-3 (∇) and pT218-4 (Δ). The solid markers indicate the plants shown in FIG. 3(b) and the arrows indicate the average values for plants transformed with pT218-1 or pT218-2.

To locate regions within the flanking plant DNA responsible for seed coat-specificity, truncated derivatives of the GUS fusion were generated (FIG. 2) and introduced into tobacco plants. Deletion of the region approximately between 2.5 and 1.0 kb, 5' of the insertion site (pT218-2, FIG. 2) did not alter expression compared with the entire 4.7 kb GUS fusion (FIGS. 3b and 4). Further deletion of the DNA, to the SnaBI restriction site approximately 0.5 kb, 5' of the insertion site (pT218-3, FIG. 2), resulted in the complete loss of GUS activity in developing seeds (FIGS. 3b and 4). This suggests that the region approximately between 1.0 and 0.5 kb, 5' of the insertion site contains elements essential to gene activation. GUS activity in seeds remained absent with more extensive deletion of plant DNA (pT218-4, FIGS. 2, 3b and 4) and was not found in other organs including leaf, stem, root, anther, petal, ovary or sepal from plants transformed with any of the vectors (data not shown).

Figure 7:
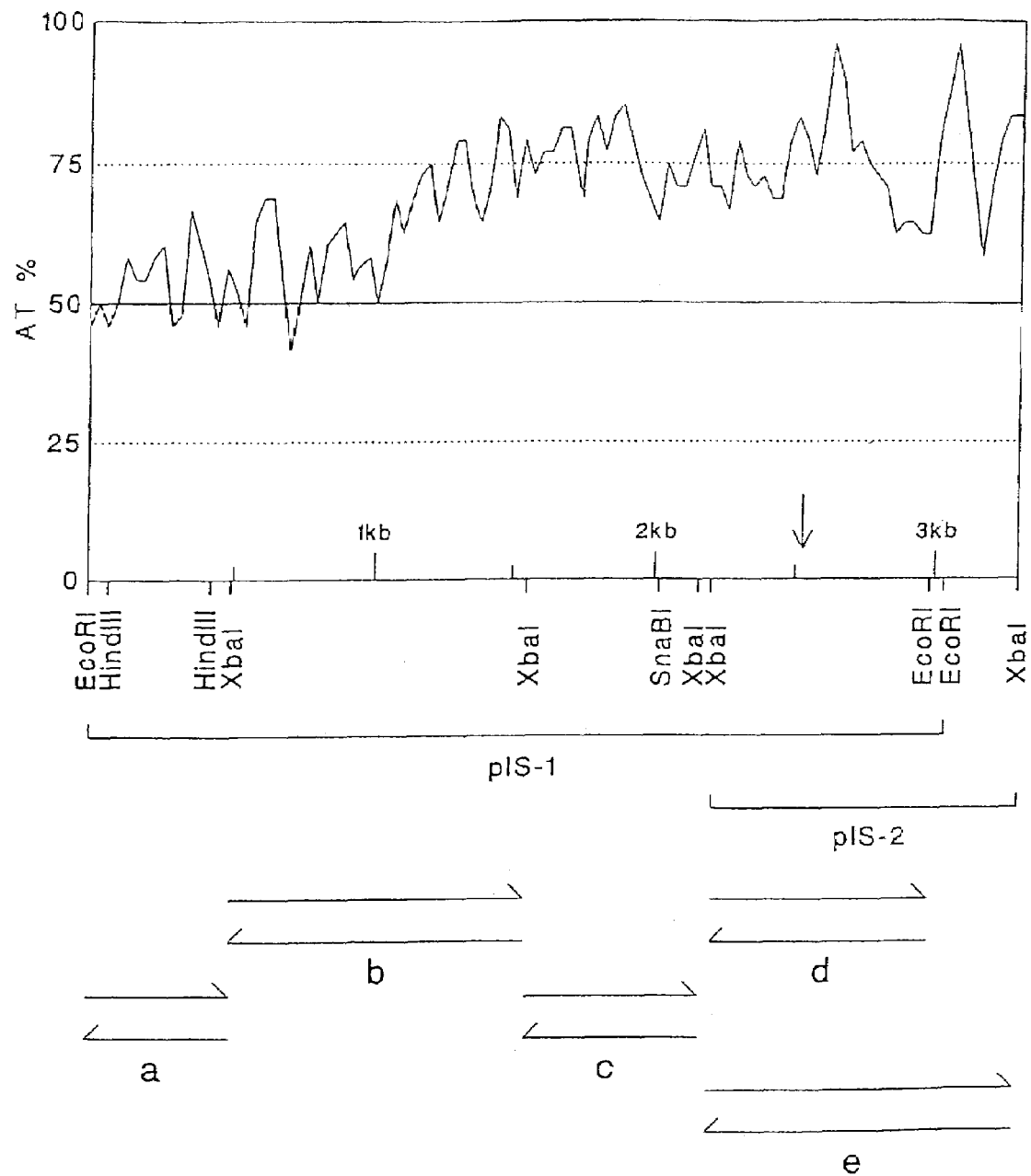
FIG. 7 shows the base composition of region surrounding the T218 insertion site cloned from untransformed plants. The site of T-DNA insertion in plant T218 is indicated by the vertical arrow. The position of the 2 genomic clones pIS-1 and pIS-2, and of the various RNA probes (a-e) used in RNase protection assays are indicated beneath the graph.

The transcriptional start site for the GUS gene in plant T218 was determined by RNase protection assays with RNA probe #4 (FIG. 2) which spans the T-DNA/plant DNA junction. For RNase protection assays, various restriction fragments from pIS-1, pIS-2 and pT218 were subcloned into the transcription vector pGEM-4Z as shown in FIGS. 7 and 2, respectively. A 440 bp HindIII fragment of the tobacco acetohydroxyacid synthase SURA gene was used to detect SURA and SURB mRNA. DNA templates were linearized and transcribed in vitro with either T7 or SP6 polymerases to generate strand-specific RNA probes using the Promega transcription kit and [$\alpha$-$^{32}$P]CTP as labelled nucleotide. RNA probes were further processed as described in Ouellet et al. (1992, Plant J 2, 321-330). RNase protection assays were performed as described in Ouellet et al., (1992, Plant J. 2, 321-330), using 10-30 µg of total RNA per assay. Probe digestion was done at 30° C. for 15 min using 30 µg ml$^{-1}$ RNase A (Boehringer Mannheim) and 100 units ml$^{-1}$ RNase T1 (Boehringer Mannheim). FIG. 5 shows that two termini were mapped in the plant DNA. The major 5' terminus is situated at an adenine residue, 122 bp upstream of the T-DNA insertion site (FIG. 6). The sequence at this transcriptional start site is similar to the consensus sequence for plant genes (C/TTCIATCA; Joshi, 1987 Nucleic Acids Res. 15, 6643-6653). A TATA box consensus sequence is present 37 bp upstream of this start site (FIG. 6). The second, minor terminus mapped 254 bp from the insertion site in an area where no obvious consensus motifs could be identified (FIG. 6).

The tobacco DNA upstream of the insertion site is very AT-rich (>75%, see FIG. 7). A search for promoter-like motifs and scaffold attachment regions (SAR), which are often associated with promoters (Brain et al., 1992, Plant Cell 4, 463-471; Gasser and Laemmli, 1986, Cell 46, 521-530), identified several putative regulatory elements in the first 1.0 kb of tobacco DNA flanking the promoterless GUS gene (data not shown). However, the functional significance of these sequences remains to be determined.

Cloning and Analysis of the Insertion Site from Untransformed Plants

A lambda DASH genomic library was prepared from DNA of untransformed N. tabacum SR1 plants by Stratagene for cloning of the insertion site corresponding to the gene fusion in plant T218. The screening of 500,000 plaques with probe #2 (FIG. 2) yielded a single lambda clone. The EcoRI and XbaI fragments were subcloned in pGEM-4Z to generate pIS-1 and pIS-2. FIG. 7 shows these two overlapping subclones, pIS-1 (3.0 kb) and pIS-2 (1.1 kb), which contain tobacco DNA spanning the insertion site (marked with a vertical arrow). DNA sequence analysis (using dideoxy nucleotides in both directions) revealed that the clones, pT218 and pIS-1, were identical over a length of more than 2.5 kb, from the insertion site to their 5' ends, except for a 12 bp filler DNA insert of unknown origin at the T-DNA border (FIG. 6 and data not shown). The presence of filler DNA is a common feature of TDNA/plant DNA junctions (Gheysen et al., 1991, Gene 94, 155-163). Gross rearrangements that sometimes accompany T-DNA insertions (Gheysen et al., 1990, Gene 94, 155-163; and 1991, Genes Dev. 5, 287-297) were not found (FIG. 6) and therefore could not account for the promoter activity associated with this region. The region of pIS-I and pIS-2, 3' of the insertion site is also very AT-rich (FIG. 7).

To determine whether there was a gene associated with the pT218 promoter, more than 3.3 kb of sequence contained with pIS-I and pIS-2 was analyzed for the presence of long open reading frames (ORFs). However, none were detected in this region (data not shown). To determine whether the region surrounding the insertion site was transcribed in untransformed plants, Northern blots were performed with RNA from leaf, stem, root, flower and seeds at 4, 8, 12, 14, 16, 20 and 24 dpa. Total RNA from leaves was isolated as described in Ouellet et al., (1992, Plant J 2, 321-330). To isolate total RNA from developing seeds, 0.5 g of frozen tissue was pulverized by grinding with dry ice using a mortar and pestle. The powder was homogenized in a 50 ml conical tube containing 5 ml of buffer (1 M Tris HCl, pH 9.0, 1% SDS) using a Polytron homogenizer. After two extractions with equal volumes of phenol:chloroform:isoamyl alcohol (25:24:1), nucleic acids were collected by ethanol precipitation and resuspended in water. The RNA was precipitated overnight in 2M LiCl at 0° C., collected by centrifugation, washed in 70% ethanol and resuspended in water. Northern blot hybridization was performed as described in Gottlob-McHugh et al. (1992, Plant Physiol 100, 820-825). Probe #3 (FIG. 2) which spans the entire region of pT2185' of the insertion did not detect hybridizing RNA bands (data not shown). To extend the sensitivity of RNA detection and to include the region 3' of the insertion site within the analysis, RNase protection assays were performed with 10 different RNA probes that spanned both strands of pIS-1 and pIS-2 (FIG. 7). Even after lengthy exposures, protected fragments could not be detected with RNA from 8, 10, 12 dpa seeds or leaves of untransformed plants (see FIG. 5 for examples with two of the probes tested). The specific conditions used allowed the resolution of protected RNA fragments as small as 10 bases (data not shown). Failure to detect protected fragments was not due to problems of RNA quality, as control experiments using the same samples detected acetohydroxyacid synthase (AHAS) SURA and SURB mRNA which are expressed at relatively low abundance (data not shown). Conditions used in the present work were estimated to be sensitive enough to detect low-abundance messages representing 0.001-0.01% of total mRNA levels (Ouellet et al., 1992, Plant J. 2, 321-330). Therefore, the region flanking the site of T-DNA insertion does not appear to be transcribed in untransformed plants.

Genomic Origins of the Insertion Site

Southern blots were performed to determine if the insertion site is conserved among Nicotiana species. Genomic DNA (5 µg) was isolated, digested and separated by agarose gel electrophoresis as described above. After capillary transfer on to nylon filters, DNA was hybridized, and probes were labelled, essentially as described in Rutledge et al. (1991, Mol. Gen. Genet. 229, 31-40). High-stringency washes were in 0.2×SSC at 65° C. while low-stringency washes were in 2×SSC at room temperature. In FIG. 8, DNA of the allotetraploid species *N. tabacum* and the presumptive progenitor diploid species *N. tomentosiformis* and *N. sylvestris* (Okamuro and Goldberg, 1985, *Mol. Gen. Genet.*, 198, 290-298) were hybridized with probe #2 (FIG. 2). Single hybridizing fragments of identical size were detected in *N. tabacum* and *N. tomentosiformis* DNA digested with HindIII, XbaI and EcoRI, but not in *N. sylvestris*. Hybridizations with pIS-2 (FIG. 8) which spans the same region but includes DNA 3' of the insertion site yielded the same results. They did not reveal hybridizing bands, even under conditions of reduced stringency, in additional *Nicotiana* species including *N. rustica*, *N. glutinosa*, *N. megalosiphon* and *N. debneyi* (data not shown). Probe #3 (FIG. 2) revealed the presence of moderately repetitive DNA specific to the *N. tomentosiformis* genome (data not shown). These results suggest that the region flanking the insertion site is unique to the *N. tomentosiformis* genome and is not conserved among related species as might be expected for regions that encode essential genes.

Characterization of a Constitutive GUS fusion—T1275

From the transgenic plants produced (see above), one of these, T1275, was chosen for detailed study because of its high level and constitutive expression of GUS (see also U.S. patent application Ser. No. 08/593,121 and PCT/CA97/00064, both of which are incorporated by reference).

Fluorogenic and histological GUS assays were performed as outlined above. For initial screening, leaves were harvested from in vitro grown plantlets. Later nine different tissues: leaf (L), stem (S), root (R), anther (A), petal (P), ovary (O), sepal (Se), seeds 10 days post anthesis (S1) and seeds 20 days post-anthesis (S2), were collected from plants grown in the greenhouse and analyzed.

GUS activity in plant T1275 was found in all tissues. FIG. 10 shows the constitutive expression of GUS by histochemical staining with X-Gluc of T1275, including leaf (a), stem (b), root (c), flower (d), ovary (e), embryos (f and g), and seed (h).

Constitutive GUS expression was confirmed with the more sensitive fluorogenic assay of plant tissue from transformed plant T1275. These results are shown in FIG. 11. GUS expression was evident in all tissue types including leaf (L), stem (S), root (R), anther (A), pistil (P), ovary (O), sepal (Se), seeds at 10 dpa (SI) and 20 dpa (S2). Furthermore, the level of GUS expression in leaves was comparable to the level of expression in transformed plants containing the constitutive promoter CaMV 35S in a GUS-nos fusion. As reported by Fobert et al. (1991, Plant Molecular Biology, 17: 837-851) GUS activity in transformed plants containing pBI121 (Clontech), which contains a CaMV 35S-GUS-nos chimeric gene, was as high as 18,770±2450 (pmole MU per minute per mg protein).

Cloning and Analysis of the Constitutive Promoter—GUS Fusion

Genomic DNA was isolated from leaves according to Hattori et al. (1987, *Anal. Biochem.* 165, 70-74). Ten μ g of T1275 total DNA was digested with EcoRI and XbaI according to the manufacturer's instructions. The digested DNA was size-fractionated on a 0.7% agarose gel. The DNA fragments of about 4 to 6 kb were isolated from the gel using the Elu-Quick kit (Schleicher and Schuell) and ligated to lambdaGEM-2 arms previously digested with EcoRI and XbaI and phosphatase-treated. About 40,000 plaques were transferred to a nylon membrane (Hybond, Amersham) and screened with the $^{32}$P-labelled 2 kb GUS insert isolated from pBI121, essentially as described in Rutledge et al. (1991, *Mol. Gen Genet*. 229, 31-40). The positive clones were isolated. The XbaI-EcoRI fragment (see restriction map FIG. 12) was isolated from the lambda phage and cloned into pTZ19R previously digested with XbaI and EcoRI and treated with intestinal calf phosphatase.

The plant DNA sequence within the clone, SEQ ID NO:2, has not been previously reported in sequence data bases. It is not observed among diverse species as Southern blots did not reveal bands hybridizing with the fragment in soybean, potato, sunflower, *Arabidopsis, B. napus, B. oleracea*, corn, wheat or black spruce (data not shown). In tobacco, Southern blots did not reveal evidence for gross rearrangements at or upstream of the T-DNA insertion site (data not shown).

The T1275 Regulatory Element is Cryptic

The 4.2 kb fragment containing about 2.2 kb of the T1275 promoter fused to the GUS gene and the nos 3' was isolated by digesting pTZ-T1275 with HindIII and EcoRI. The isolated fragment was ligated into the pRD400 vector (Datla et al., 1992, *Gene*, 211:383-384) previously digested with HindIII and EcoRI and treated with calf intestinal phosphatase. Transfer of the binary vector to *Agrobacterium tumefaciens* and leaf disc transformation of *N. tabacum* SRI were performed as described above. GUS activity was examined in several organs of many independent transgenic lines. GUS mRNA was also examined in the same organ by RNase protection assay (Melton et al, 1984, *Nucleic Acids Res*. 121: 7035-7056) using a probe that mapped the mRNA 5' end in both untransformed and transgenic tissues. RNA was isolated from frozen-ground tissues using the TRIZOL Reagent (Life Technologies) as described by the manufacturer. For each assay 10-30 ug of total RNA was hybridized to RNA probes described in FIG. 16(A). Assays were performed using the RPAII kit (Ambion CA) as described by the manufacturer. The protected fragments were separated on a 5% Long Ranger acrylamide (J.J. Baker, N.J.) denaturing gel which was dried and exposed to Kodak X-RP film.

RNase protection assays performed with RNA from leaves, stem, root, developing seeds and flowers of transgenic tobacco revealed a single protected fragment in all organs indicating a single transcription start site that was the same in each organ, whereas RNA from untransformed tobacco tissues did not reveal a protected fragment (FIG. 16(B)). The insertion site, including 1200 bp downstream, was cloned from untransformed tobacco as a PCR fragment and sequenced. A composite restriction map of the insertion site was assembled as shown in FIG. 16(A). RNA probes were prepared that spanned the entire region as shown in FIG. 16(A). RNase protection assays did not reveal transcripts from the sense strand as summarized in Table 2. These data suggest that the insertion site is transcriptionally silent in untransformed tobacco and is activated by T-DNA insertion. The region upstream of the insertion site is therefore another example of a plant cryptic regulatory element.

TABLE 2

Summary of the RNase Protection Assays of the insertion site in untransformed tobacco. See FIG. 16 (A) for probe positions.

| Probe | Rnase Protection Assay result |
|---|---|
| Looking for "sense" RNAs | (relative to the T1275 promoter) |
| C8-EcoRI | many bands, all in tRNA (negative control) |
| A10-HindIII | no bands |
| 2-21-HindIII | no bands |

TABLE 2-continued

Summary of the RNase Protection Assays of
the insertion site in untransformed tobacco.
See FIG. 16 (A) for probe positions.

| Probe | Rnase Protection Assay result |
|---|---|
| 1-4 SmaI | many bands, all in tRNA |
| 7-EcoRI | faint bands, all in tRNA |

Constitutive Activity of the T1275 Regulatory Element

For analysis of transient expression of GUS activity mediated by biolistics (Sandford et al, 1983, *Methods Enzymol*, 217: 483-509), the XbaI-EcoRI fragment was subcloned in pUC19 and GUS activity was detected by staining with X-Gluc as described above. Leaf tissue of greenhouse-grown plants or cell suspension cultures were examined for the number of blue spots that stained. As shown in Table 3, the T1275-GUS-nos gene was active in each of the diverse species examined and can direct expression of a gene of interest in all plant species tested. Leaf tissue of canola, tobacco, soybean, alfalfa, pea and *Arabidopsis*, potato, Ginseng, peach and cell suspensions of oat, corn, wheat and barley exhibited GUS-positive blue spots after transient bombardment-mediated assays and histochemical GUS activity staining. This suggests that the T1275 regulatory element may be useful for directing gene expression in both dicot and monocot plants.

TABLE 3

Transient Expression of GUS Activity
in Tissues of Diverse Plant Species

| Tissue Source | Species | GUS Activity* |
|---|---|---|
| Leaf | Soybean | +++ |
| | Alfalfa | ++ |
| | *Arabidopsis* | + |
| | Potato | ++ |
| | Ginseng | ++ |
| | Peach | + |
| Leaf disc | Tobacco | ++ |
| | *B. napus* | + |
| | Pea | + |
| Cell Cultures | Oat | + |
| | Corn | + |
| | Wheat | + |
| | Barley | ++ |
| | White spruce | ++ |

*Numbers of blue spots: 1-10 (+), 10-100 (++), 100-400 (+++)

For analysis of GUS expression in different organs, lines derived from progeny of the above transgenic tobacco lines were examined in detail. Table 4 shows the GUS specific activities in one of these plants. It is expressed in leaf, stem, root, developing seeds and the floral organs, sepals, petals, anthers, pistils and ovaries at varying levels, confirming constitutive expression. Introduction of the same vector into *B. napus*, *Arabidopsis*, and alfalfa also revealed expression of GUS activity in these organs (data not shown) indicating that constitutive expression was not specific to tobacco. Examination of GUS mRNA in the tobacco organs showed that the transcription start sites was the same in each (FIG. 16(B)) and the level of mRNA was similar except in flower buds where it was lower (Table 4).

TABLE 4

GUS Specific Activity and Relative RNA Levels in the
Organs of Progeny of Transgenic Line T64

| | Relative GUS RNA Levels in T64 | GUS Specific Activity (picomol/MU/min/mg protein) | |
|---|---|---|---|
| Organ | Progeny (grey scale units) | Transformed Tobacco T64 | Untransformed Tobacco |
| Leaf | 1774 | 988.32 | 3.02 |
| Stem | 1820 | 826.48 | 7.58 |
| Root | 1636 | 4078.45 | 22.18 |
| 14 day post anthesis Seeds | 1790 | 253.21 | 10.03 |
| Flower - buds | 715 | 2.59 | ND* |
| Petals | ND* | 28.24 | 1.29 |
| Anthers | ND* | 4.64 | 0.35 |
| Pistils | ND* | 9.76 | 1.72 |
| Sepals | ND* | 110.02 | 2.48 |
| Ovary | ND* | 4.42 | 2.71 |

*Not Done

Identification of Regulatory Elements within the Full Length T1275 Regulatory Element An array of deletions of the full length regulatory region of T1275 were prepared, as identified in FIGS. 13(B) and (C), for further analysis of the cryptic regulatory element.

5' deletions of the promoter (see FIGS. 13(B) and (C) and analysis by transient expression using biolistics showed that the promoter was active within a fragment 62 bp from the transcriptional start site indicating that the core promoter has a basal level of expression (see Table 5).

TABLE 5

Transient GUS activity detected in soybean leaves
by staining with X-gluc after particle bombardment.
Vectors illustrated in FIGS. 13 (B) and (C).

| Genes | GUS staining |
|---|---|
| 1. T1275-GUS-nos | + |
| 2. -1639-GUS-nos | + |
| 3. -1304-GUS-nos | + |
| 4. -684-GUS-nos | + |
| 5. -394-GUS-nos | + |
| 6. -197-GUS-nos | + |
| 7. -62-GUS-nos | + |
| 8. -62(-tsr)-GUS-nos | + |
| 9. -12-GUS-nos | − |
| 10. +30-GUS-nos | − |

Deletion of a fragment containing the transcriptional start site (see −62(-tsr)/GUS/nos in FIG. 14(B), Table 5) did not eliminate expression, however deletions to −12 bp and further (ie+30) did eliminate expression indicating that the region defined by bp β62 to −12 (nucleotides 1992-2042 of SEQ ID NO:2) contained the core promoter. DNA sequence searches did not reveal conventional core promoter motifs within this region as are typically found in plant genes, such as the TATA box.

A number of the 5' promoter deletion clones (FIGS. 13(B) and (C)) were transferred into tobacco by *Agrobacterium*-mediated transformation using the vector pRD400. Analysis of GUS specific activity in leaves of transgenic plants (see Table 6) confirmed the transient expression data down to the −197 fragment (i.e. nucleotide 1857 SEQ ID NO:2).

TABLE 6

GUS specific activities in leaves of greenhouse-grown transgenic tobacco, SR1, transformed with the T1275-GUS-nos gene fusion and 5' deletion clones (see FIG. 13 A). Mean ± SE(n)

| Genes | GUS specific activities pmoles MU/min/mg protein |
|---|---|
| 1. T1275-GUS-nos | 283 ± 171 (27) |
| 2. −1639-GUS-nos | 587 ± 188 (26) |
| 3. −1304-GUS-nos | 632 ± 217 (10) |
| 4. −684-GUS-nos | nd* |
| 5. −394-GUS-nos | 1627 ± 340 (13) |
| 6. −197-GUS-nos | 475 ± 74 (27) |

*nd = not determined

Histochemical analysis of organs sampled from the transgenic plants indicated GUS expression in leaf, seeds and flowers.

To determine if enhancer elements exist, fragments −394 to −62 (nucleotides 1660 to 1992 of SEQ Id NO:20) and −197 to −62 (nucleotides 1875 to 1992 of SEQ ID NO:2) were fused to the −46 35S core promoter. Both fragments raised the expression of the core promoter about 150 fold (FIG. 13 (D), constructs DRA1-35S and BST1-35S). Doubling of the −394 to −62 region (nucleotides 1660 to 1992 of SEQ ID NO:2) resulted in a 1.8 fold increase in GUS activity when fused to T1275 core promoter (BST1-GUS (−394-GUS) v. BST2-GUS; FIG. 13(D)), a similar effect is observed when the −394 to −62 region is double and fused to the 35S core promoter (BST1-35S v. BST2-35S). Doubling of the −197 to −62 fragment (nucleotides 1875 to 1992 of SEQ ID NO:2) also produced increased GUS activity when fused to the T1275 core promoter (DRA2-GUS).

The −197 to −62 fragment (nucleotides 1875 to 1992 of SEQ ID NO:2; DRA1-35S), the −197 to −62 fragment in reverse orientation, or inverted (DRA1R-35S), and a repeat of the −197 to −62 fragment (DRA2-35S) were also fused with the 35S minimal promoter (FIG. 13(E) and used to transform *Arabidopsis*.

*Arabidopsis* plants with immature floral buds and few silques were transformed with the above constructs by dipping the plant into a solution containing *Agrobacterium tumefaciens*, 2.3 g/L MS, 5% (w/v) sucrose and 0.03% Silwet L-77 (Lehle Seeds, Round Rock, Tex.) for 1-2 min, and allowing the plants to grow and set seed. Seeds from mature plants were collected, dried at 25° C., and sown on sterile media containing 40 μg/mL kanamycin to select transformants. Surviving plantlets were transferred to soil, grown and seed collected.

Constructs comprising the −197 to −62 fragment (nucleotides 1875 to 1992 of SEQ ID NO:2) in regular or inverted orientation exhibited increased transcriptional enhancer activity, over that of the minimal promoter (FIG. 13 (F). A further increase in activity was observed when plants were transformed with constructs comprising repeated regions of this regulatory element (FIG. 13(F). Tissue staining of transformed plants expressing DRA1-35S indicated that this construct was expressed constitutively as it was detected in all tested organs, including flower, silque and seedling (FIG. 13(G)).

Activity of the T1275 Regulatory Element

Analysis of leaves of randomly-selected, greenhouse-grown plants regenerated from culture revealed a wide range of GUS specific activities (FIG. 14(A); T plants). Plants transformed with pBI 121 (CLONETECH) which contains the 35S-GUS-nos gene yielded comparable specific activity levels (FIG. 14(A); S plants). Furthermore, the GUS protein levels detected by Western blotting were similar between plants transformed with either gene when the GUS specific activities were similar (FIG. 14(C)).

Generally, the level of GUS mRNA in the leaves as determined by RNase protection (FIG. 14(B)) correlated with the GUS specific activities, however, the level of GUS mRNA was about 60 fold (mean of 13 measurements) lower in plants transformed with the T1275-GUS-nos gene (FIG. 14(B)) when compared with plants transformed with 35S-GUS-nos.

Since the levels of protein and the activity of extractable protein were similar in plants transformed with T1275-GUS-nos or 35S-GUS-nos, yet the mRNA levels were dramatically different, these results suggested the existence of a regulatory element downstream of the transcriptional start site in the sequence of T1275-derived transcript.

Post-Transcriptional Regulatory Elements within T1275

An experiment was performed to determine the presence of a post-transcriptional regulatory element within the T1275 leader sequence. A portion of the sequence downstream from the transcriptional initiation site was deleted in order to examine whether this region may have an effect on translational efficiency (determined by GUS extractable activity), mRNA stability or transcription.

Deletion of the Nde1-Sma1 fragment ("N"; SEQ ID NO:3) from the T1275-GUS-nos gene (FIG. 15; T1275-N-GUS-nos; includes nucleotides 2084-2224 of SEQ ID NO:2) resulted in at least about 46-fold reduction in the amount of GUS specific activity that could be detected in leaves of transgenic tobacco cv Delgold (see Table 7). Similar results, of about at least a 40 fold reduction in GUS activity due to the deletion of the Nde1-Sma1 fragment, were observed in transgenic tobacco cv SR1 and transgenic alfalfa (Table 7). Addition of the same fragment (Nde1-Sma1) to a 355-GUS-nos gene (FIG. 15; 35S+N-GUS-nos) construct increased the amount of GUS specific activity by about 5-fold in tobacco, and by a much higher amount in alfalfa (see Table 7).

TABLE 7

GUS specific activity in leaves of greenhouse-grown transgenic tobacco cv Delgold transformed with vectors designed to assess the presence of cryptic regulatory sequences within the transcribed sequence derived from the T1275 GUS gene fusion (see FIG. 15). Mean ± SE(n).

| Construct | GUS specific activity pmoles MU/min/mg protein | | | |
|---|---|---|---|---|
| | Delgold (1) | Delgold (2) | SR1 | Alfalfa |
| 1. T1275-GUS-nos | 557 ± 183 (21) | 493 ± 157 (25) | 805 ± 253 (22) | 187 ± 64 (24) |
| 2. T1275-N-GUS-nos | 12 ± 3 (22) | 12 ± 3 (27) | 6 ± 2 (25) | 4 ± 0.5 (25) |

TABLE 7-continued

GUS specific activity in leaves of greenhouse-grown transgenic tobacco cv Delgold transformed with vectors designed to assess the presence of cryptic regulatory sequences within the transcribed sequence derived from the T1275 GUS gene fusion (see FIG. 15). Mean ± SE(n).

| | GUS specific activity pmoles MU/min/mg protein | | | |
|---|---|---|---|---|
| Construct | Delgold (1) | Delgold (2) | SR1 | Alfalfa |
| 3. 35S-GUS-nos | 1848 ± 692 (15) | 1347 ± 415 (26) | 1383 ± 263 (25) | 17 ± 11 (24) |
| 4. 35S + N-GUS-nos | 6990 ± 3148 (23) | 6624 ± 2791 (26) | 6192 ± 1923 (24) | 1428 ± 601 (24) |

A similar effect was noted in organs tested from transformed tobacco (Table 8) and alfalfa plants (Table 9)

TABLE 8

Expression of T1275-GUS-nos (+N) compared with T1275-(-N)-GUS-nos (-N) in organs of transgenic tobacco. Mean ± SE(n = 5).

| | GUS specific Activity (pmol MU/min/mg/protein) | | | |
|---|---|---|---|---|
| | Delgold | | SR1 | |
| Organ | +N | -N | +N | -N |
| Leaf | 1513 ± 222 | 35 ± 4 | 904 ± 138 | 4 ± 1 |
| Flower | 360 ± 47 | 38 ± 8 | 175 ± 44 | 28 ± 3 |
| Seed | 402 ± 65 | 69 ± 7 | 370 ± 87 | 33 ± 5 |

TABLE 9

Expression of T1275-GUS-nos, T1275-(-N)-GUS-nos, 35S-GUS-nos, 35S-GUS(+N)-GUS-nos in organs of transgenic alfalfa. Mean ± SE(n = 5).

| Construct | GUS Specific Activity (pmol Mu/min/mg protein) | | | |
|---|---|---|---|---|
| | Leaf | Petiole | Stem | Flower |
| T1275-GUS | 756 ± 73.6 | 1126 ± 72.7 | 1366.7 ± 260 | 456.1 ± 160.9 |
| T1275 (-N) GUS | 5.4 ± 1.4 | 7.6 ± 1.2 | 8.1 ± 2.0 | 7.25 ± 1.7 |
| 35S-GUS | 67.5 ± 50.3 | 48.9 ± 23.2 | 56.8 ± 28.7 | 23.2 ± 7.3 |
| 35S (+N) GUS | 5545 ± 2015 | 10791 ± 6194 | 9931 ± 5496 | 1039 ± 476.7 |
| Control | 3.7 | 13.2 | 11.8 | 18.7 |

In transient expression assays using particle bombardment of tobacco leaves, the NdeI-SmaI fragment fused to the minimal -46 35S promoter enhanced basal level of 35S promoter activity by about 80 fold (28.67±2.91 v. 0.33±0.33 relative units; No.blue units/leaf).

SEQ ID NO:3 comprises nucleotides 2084 to 2224 of SEQ ID NO:2. Nucleotides 1-141 of SEQ ID NO3: comprise nucleotides obtained from the plant portion of T1275 (nucleotides 2084 to 2224 of SEQ ID NO :2). Nucleotides 142-183 of SEQ ID NO:3 comprise vector sequence between the enhancer fragment and the GUS ATG. The GUS ATG is located at nucleotides 186-188 of SEQ ID NO:3.

A shortened fragment of the NdeI-SmaI fragment (see SEQ ID NO:4), referred to as "ΔN", "dN", or "deltaN" and lacking the out-of frame upstream ATG at nucleotide 2087-2089 of SEQ ID NO:2, was also constructed and tested in a variety of species. ΔN was created by replacing the NdeI site (FIG. 18(A)) within the leader sequence to a BglII site thereby eliminating the upstream ATG at position 2086 of SEQ ID NO:2. A Kozak consensus sequence was also constructed at the initiator MET codon and a NcoI site was added to facilitate construction with other coding regions (see FIG. 18(B)). Nucleotides 1-86 of SEQ ID NO:4 (i.e.ΔN with Kozack sequence) are derived from T1275 (nucleotides 2084-2170 of SEQ ID NO:2). ΔN also includes a Kozack sequence from nucleotides 87 to 97 of SEQ ID NO:4, and nucleotides 98 to 126 of SEQ ID NO:4 comprise the vector sequence between the enhancer fragment and the GUS ATG. The GUS ATG is located at nucleotides 127-129 of SEQ ID NO:4).

Constructs comprising ΔN, for example T1275(N)-GUS-nos, when introduced into tobacco yielded 5 fold greater levels of GUS activity in leaves of transgenic tobacco (5291±986 pmolMU/min/mg protein; (n=29) compared to plants expressing T1275-GUS-nos (1115±299 pmol MU/min/mg protein; n=29).

Activity of Ndei-Sma1, N, and ΔN in Other Species

In monocots, transient expression in corn callus indicated that the NdeI-SmaI fragment (SEQ ID NO:3), or a shortened NdeI-SmaI fragment, ΔN (SEQ ID NO:4), significantly increases GUS expression driven by the 35 S promoter, but not to the higher level of expression generated in the presence of the ADH1 intron ("i"; FIG. 19 and Table 10).

TABLE 10

Transient expression analysis of GUS activity in bombarded corn calli. Luciferase activity was used to normalize the data. Mean ± se (n = 5).

| Construct | Ratio GUS:Luciferase activity |
|---|---|
| 35S GUS-nos | 7.4 ± 4 |
| 35S(+N)-GUS-nos | 19 ± 5 |
| 35S (ΔN)-GUS-nos | 18 ± 10 |
| 35S-i-GUS-nos | 66 ± 27 |

The functionality of the NdeI-SmaI fragment (SEQ ID NO:3) was also determined in non-plant species. In conifers, for example white spruce, transient bombardment of cell culture exhibited an increase in expression (Table 11).

TABLE 11

Expression of T1275-GUS-nos, T1275(-N)-GUS-nos, 35S-GUS-nos, 35S (+N)-GUS-nos in white spruce embryonal masses following bombardment (n = 3).

| Construct | Average GUS expression per leaf (Number of blue spots) |
|---|---|
| T1275-GUS-nos | 72.67 ± 9.33 |
| T1275(-N)-GUS-nos | 21.33 ± 4.49 |
| 35S-GUS-nos | 113.67 ± 17.32 |
| 35S(+N)-GUS-nos | 126.33 ± 19.41* |

*average spot much greater in size and strength.

In yeast, the presence of the NdeI-SmaI fragment (SEQ ID NO:3) or ΔN (SEQ ID NO:4) exhibited strong increase in expression of the marker gene. A series of constructs comprising a galactose inducible promoter $P_{galP}$, various forms of the Nde1-Sma1 fragment, and GUS (UidA) were made within the yeast plasmid pYES2. A full length Nde1-Sma1 fragment N (pYENGUS), N (containing a Kozak consensus sequence; pYEdNGUS), and ΔN without a Kozak consensus sequence (pYEdN$^M$GUS; or ΔN$^M$) were prepared (see FIG. 20, and SEQ ID NO:5).

Nucleotides 1-86 of SEQ ID NO :5 (ΔN$^M$) comprise a portion of the enhancer regulatory region obtained from T1275 (nucleotide 2084-2170 of SEQ ID NO:2), while nucleotides 87-116 comprise a vector sequence between the enhancer fragment and the GUS ATG which is located at nucleotides 117-119 of SEQ ID NO:5.

These constructs were tested in yeast strain INVSC1 using known transformation protocols (Agatep R. et al. 1998, http://www.biomednet.com/db/tto). The yeast were grown in non-inducible medium comprising raffinose as a carbon source for 48 hr at 30° C. and then transferred onto inducible medium (galactose as a carbon source). Yeast cells were harvested after 4 hr post induction and GUS activity determined quantitatively. Up to about a 12 fold increase in activity was observed with constructs comprising ΔN. Constructs comprising ΔN$^M$ exhibited even higher levels of reporter activity. The results indicate that the Nde1-Sma1 fragment (SEQ ID NO:3), ΔN (SEQ ID NO:4) and ΔN$^M$ (SEQ ID NO:5) are functional in yeast (Table 12).

TABLE 12

Expression of pYEGUS, pYENGUS, pYEdNGUS, and pYEdN$^M$GUS (ΔN, without a Kozak consensus sequence) in transformed yeast (n = 5).

| Construct | Expt. 1 Activity | Expt. 2 Activity |
|---|---|---|
| pYES-GUS-nos | 93 ± 15 | 407 ± 8 |
| pYES(+N)-GUS-nos | 753 ± 86 | 1771 ± 191 |
| pYES(ΔN)-GUS-nos | 1119 ± 85 | 2129 ± 166 |
| PYES(ΔN$^M$)-GUS-nos | 1731 ± 45 | 6897 ± 536 |

Constructs containing ΔN$^M$ (i.e. ΔN lacking the Kozack sequence; SEQ ID NO:5) were also tested in insect cells. These constructs comprised the insect virus promoter ie2 (Theilmann D. A and Stewart S., 1992, Virology 187: pp. 84-96) in the present or absence of ΔN$^M$ and CAT (chloramphenicol acetyltransferase) as the reporter gene. The insect line, Ld652Y, derived from gypsy moth (*Lymantria dispar*) was transiently transformed with the above constructs using liposomes (Campbell M. J. 1995, Biotechniques 18: pp. 1027-1032; Forsythe I. J. et al 1998, Virology 252: pp. 65-81). Cells were harvested 48 hours after transformation and CAT activity quanitatively measured using tritiated acetyl-CoA (Leahy P. et al. 1995 Biotechniques 19: pp. 894-898). The presence of the translational enhancer was found to significantly modulate the activity of the insect promoter-reporter gene construct in insect cells.

Bacteria were transformed with either pBI221, comprising 35S promoter and GUS, or 35S–N-GUS, comprising the full length Nde1-Sma1 fragment (SEQ ID NO:3). Since uidA (GUS) is native to *E. coli*, two uidA mutants, uidA1 and uidA2, that do not express uidA, were used for these experiments (mutants obtained from *E. coli* Genetic Center 335 Osborn Memorial Laboratories, Department of Biology, Box 208104, Yale University, New Haven Conn. 06520-8104). These bacteria were transformed using standard protocols, and transformants were assessed by assaying GUS activity from a 50 µl aliquot of an overnight culture. The "N" fragment (35s–N-GUS) was observed to modulate the activity of the reporter gene in bacterial cells.

These data are consistent with the presence of a post-transcriptional regulatory sequence in the NdeI-SmaI fragment.

The NdeI-SmaI Fragment Functions as a Transcriptional Enhancer or mRNA Stability Determinant The levels of mRNA were determined in leaves obtained from tobacco plants transformed with either T1275-GUS-nos, T1275–N-GUS-nos, 35S-GUS-nos, or 35S+N-GUS-nos (FIGS. 17(A) and (B)). Relative RNA levels were determined by ribonuclease protection assay (Ambion RPAII Kit) in the presence of α-$^{32}$P-CTP labeled in vitro transcribed probe and autoradiographic quantification using Kodak Digital Science 1 D Image Analysis Software. Hybridization conditions used during RNase protection assay were overnight at 42-45 degrees in 80% formamide, 100 mM sodium citrate pH 6.4, 300 mM sodium acetate pH 6.4, 1 mM EDTA.

The levels of mRNA examined from transgenic tobacco plants transformed with either T1275-GUS-nos, T1275–N-GUS-nos, 35S-GUS-nos, or 35S+N-GUS-nos, were higher in transgenic plants comprising the NdeI-SmaI fragment under the control of the T1275 promoter but lower in those under the control of the 35S promoter, than in plants comprising constructs that lack this region (FIGS. 17(A) and (B)). This indicates that this region functions by either modulating transcriptional rates, or the stability of the transcript, or both.

The NdeI-SmaI Fragment Functions as a Translational Enhancer

Analyses were performed in order to determine whether the NdeI-SmaI region (SEQ ID NO:3) functions post-transcriptionally. The GUS specific activity:relative RNA level was determined from the GUS specific activity measurements, and relative RNA levels in greenhouse grown transgenic plants (FIG. 17(C)). The ratio of GUS specific activity to relative RNA level in individual transgenic tobacco plants comprising the NdeI-SmaI fragment is higher than in plants that do not comprise this region (FIG. 17(C)). Similar results are obtained when the data are averaged, indicating an eight fold reduction in GUS activity per RNA. Similarly, an increase, by an average of six fold, in GUS specific activity is observed when the NdeI-SmaI region is added within the 35S untranslated region (FIG. 17(C)). The GUS specific activity:relative RNA levels are similar in constructs containing the NdeI-SmaI fragment (T1275-GUS-nos and 35S+N-GUS-nos). These results indicate that the NdeI-SmaI fragment (SEQ ID NO:3) modulates gene expression post-transcriptionally.

Further experiments, involving in vitro translation, suggest that this region is a novel translational enhancer. For these experiments, fragments, from approximately 3' of the transcriptional start site to the end of the terminator, were excised from the constructs depicted in FIG. 15 using appropriate restriction endonucleases and ligated to pGEM4Z at an approximately similar distance from the transcriptional start site used by the prokaryotic T7 RNA polymerase. Another construct containing the AMV enhancer in the 5' UTR of a GUS-nos fusion was similarly prepared. This AMV-GUS-nos construct was created by restriction endonuclease digestion of an AMV-GUS-nos fusion, with BglII and EcoRI, from pBI525 (Datla et al., 1993, Plant Science 94: 139-149) and ligation with pGEM4Z (Promega) digested with BamHI and EcoRI. Transcripts were prepared in vitro in the presence of m$^7$G(5')ppp(5')G Cap Analog (Ambion). Transcripts were translated in vitro in Wheat Germ Extract (Promega) in the presence of 35S-Methionine and fold enhancement calculated from TCA precipitable cpms.

Translation of transcripts in vitro demonstrate an increase in translational efficiency of RNA containing the NdeI to SmaI fragment (see Table 13).

TABLE 13

In vitro translation of mRNA obtained from transgenic tobacco plants transformed with vectors with or without a NdeI-SmaI fragment obtained from the T1275 GUS gene fusion (see FIG. 15) using wheat germ extract.

| in vitro transcript | in vitro translation fold enhancement |
| --- | --- |
| T1275-GUS-nos | 3.7 |
| T127S-N-GUS-nos | 1.0 |
| AMV-GUS-nos | 1.9 |

The levels of protein produced using mRNAs comprising the NdeI-SmaI fragment are also greater than those produced using the known translational enhancer of Alfalfa Mosaic Virus RNA4 (Jobling S. A. and Gehrke L. 1987, Nature, vol 325 pp. 622-625; Datla R. S. S. et al 1993 Plant Sci. vol 94, pp. 139-149). These results indicate that this region functions post-transcriptionally, as a translational enhancer.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

We claim:

1. An isolated nucleic acid comprising nucleotides 1875-1992 of SEQ ID NO:2, or comprising a nucleotide sequence that hybridizes to the nucleotide sequence of nucleotides 1875-1992 of SEQ ID NO:2, or its complement, under the following hybridization conditions: hybridization at 4×SSC at 65° C., followed by washing in 0.1×SSC at 65° C. for an hour, wherein the nucleic acid exhibits a property of modulating constitutive expression of a nucleotide sequence in operative association therewith.

2. A vector comprising the nucleic acid of claim 1, operatively linked with a nucleic acid sequence encoding a protein.

3. A transgenic plant, plant seed or plant cell comprising the vector of claim 2.

4. The transgenic plant of claim 3, wherein the plant is a tree.

5. The nucleic acid of claim 1, comprising nucleotides 1660-1992 of SEQ ID NO:2.

6. A transgenic plant, plant seed or plant cell comprising the nucleic acid of claim 5, operatively linked to a nucleic acid encoding a protein.

7. The nucleic acid of claim 5, wherein nucleotides 1660-1992 of SEQ ID NO:2 are repeated.

8. A transgenic plant, plant seed or plant cell comprising the nucleic acid of claim 7, operatively linked to a nucleic acid encoding a protein.

9. The nucleic acid of claim 1, wherein nucleotides 1875-1992 of SEQ ID NO:2 are repeated.

10. A transgenic plant, plant seed or plant cell comprising the nucleic acid of claim 9, operatively linked to a nucleic acid encoding a protein.

11. The nucleic acid of claim 1, comprising nucleotides 1-2224 of SEQ ID NO:2.

12. A transgenic plant, plant seed or plant cell comprising the nucleic acid of claim 11, operatively linked to a nucleic acid encoding a protein.

13. The nucleic acid of claim 1, comprising a nucleotide sequence selected from the group consisting of:
   i) 415-2224, of SEQ ID NO:2;
   ii) 750-2224, of SEQ ID NO:2;
   iii) 1370-2224, of SEQ ID NO:2;
   iv) 1660-2224, of SEQ ID NO:2;
   v) 1875-2224, of SEQ ID NO:2.

14. A vector comprising the nucleic acid of claim 13, operatively associated with a nucleic acid sequence encoding a protein.

15. A transgenic plant, plant seed or plant cell comprising the vector of claim 14.

16. The transgenic plant of claim 15, wherein the plant is a tree.

17. A vector comprising the nucleic acid of claim 5, operatively associated with a nucleic acid sequence encoding a protein.

18. A transgenic plant, plant seed or plant cell comprising the vector of claim 17.

19. A vector comprising the nucleic acid of claim 11, operatively associated with a nucleic acid sequence encoding a protein.

20. A transgenic plant, plant seed or plant cell comprising the vector of claim 19.

* * * * *

UNITED STATES PATENT AND TRADEMARK OFFICE
CERTIFICATE OF CORRECTION

PATENT NO. : 7,303,873 B2  Page 1 of 1
APPLICATION NO. : 10/437261
DATED : December 4, 2007
INVENTOR(S) : Miki et al.

It is certified that error appears in the above-identified patent and that said Letters Patent is hereby corrected as shown below:

In The Claims:

Claim 13, Col. 42, Line 29: Delete "2." at end of line and insert -- 2; --

Claim 13, Col. 42, Line 29: Insert -- vi) 1875-2084 of SEQ ID NO:2. -- after line "iv) 1875-2224, of SEQ ID NO:2;"

Signed and Sealed this

Tenth Day of June, 2008

JON W. DUDAS
*Director of the United States Patent and Trademark Office*